(12) United States Patent
Burgard et al.

(10) Patent No.: US 7,041,704 B2
(45) Date of Patent: May 9, 2006

(54) METHODS OF TREATING GASTROINTESTINAL TRACT DISORDERS USING SODIUM CHANNEL MODULATORS

(75) Inventors: Edward C. Burgard, Chapel Hill, NC (US); Steven B. Landau, Wellesley, MA (US); Matthew Oliver Fraser, Apex, NC (US)

(73) Assignee: Dynogen Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 11/057,024

(22) Filed: Feb. 11, 2005

(65) Prior Publication Data

US 2005/0203190 A1     Sep. 15, 2005

Related U.S. Application Data

(62) Division of application No. 10/769,071, filed on Jan. 30, 2004.

(60) Provisional application No. 60/495,958, filed on Aug. 18, 2003, provisional application No. 60/480,598, filed on Jun. 20, 2003, provisional application No. 60/480,565, filed on Jun. 20, 2003, provisional application No. 60/443,731, filed on Jan. 30, 2003, provisional application No. 60/443,730, filed on Jan. 30, 2003.

(51) Int. Cl.
*A61K 33/18* (2006.01)
*A61K 31/45* (2006.01)
*A61K 31/04* (2006.01)

(52) U.S. Cl. .................. 514/727; 514/729; 514/741
(58) Field of Classification Search ............... 514/727, 514/730, 741
See application file for complete search history.

(56) References Cited

U.S. PATENT DOCUMENTS

| 5,331,013 | A | 7/1994 | Ahlman et al. |
| 6,124,308 | A | 9/2000 | Nobbs et al. |
| 6,265,405 | B1 | 7/2001 | Cox et al. |
| 6,355,637 | B1 | 3/2002 | Axt et al. |
| 6,576,669 | B1 * | 6/2003 | Anderskewitz et al. ..... 514/637 |
| 6,821,739 | B1 * | 11/2004 | Braun et al. ............... 435/7.1 |
| 2003/0036070 | A1 * | 2/2003 | Chakravarti .................. 435/6 |

FOREIGN PATENT DOCUMENTS

| EP | 0 400 495 A1 | 5/1990 |
| WO | WO 98/38174 | 9/1998 |
| WO | WO 01/45684 A2 | 6/2001 |

OTHER PUBLICATIONS

Cintron, L.M., et al., "Neuropathic Agents for Treating Chronic Visceral Pain," *Society for neuroscience Abstracts*, 2001, p. 927 vol. 27(1).

Holzer, P., "Gastrointestinal Afferents as Targets of Novel Drugs for the Treatment of Functional Bowel Disorders and Visceral Pain," *European Journal of Pharmacology*, 2001, pp. 177-193, vol. 429(1-3).

Pevarello, P., et al., "synthesis and Anticonvulsant Activity of a New Class of 2-[(Arylalkyl)amino] alkanamide Derivatives," *Journal of Medicinal Chemistry*, 1998, pp. 579-590, vol. 41(4).

Scholz, A., et al., "Complex Blockade of TTX-Resistant Na+ Currents by Lodocaine and Bupivacaine Reduce Firing Frequence in DRG Neurons," *Journal of Neurophysiology*, 1998, pp. 1746-1754, vol. 79(4).

* cited by examiner

*Primary Examiner*—Vickie Kim
(74) *Attorney, Agent, or Firm*—Alston & Bird LLP

(57) ABSTRACT

The invention relates to methods of using sodium channel modulators, particularly TTX-R sodium channel modulators and/or activity dependent sodium channel modulators to treat a gastrointestinal tract disorders, particularly inflammatory bowel disorders and irritable bowel syndrome.

9 Claims, 2 Drawing Sheets

A.

B.

A.

B.

METHODS OF TREATING GASTROINTESTINAL TRACT DISORDERS USING SODIUM CHANNEL MODULATORS

CROSS-REFERENCE TO RELATED APPLICATIONS

This application is a divisional of copending U.S. application Ser. No. 10/769,071, filed Jan. 30, 2004; which claims the benefit of U.S. Provisional Application No. 60/443,731, filed Jan. 30, 2003, U.S. Provisional Application No. 60/443,730, filed Jan. 30, 2003, U.S. Provisional Application No. 60/480,565, filed Jun. 20, 2003, U.S. Provisional Application No. 60/480,598, filed Jun. 20, 2003, and U.S. Provisional Application No. 60/495,958, filed Aug. 18, 2003; the contents of which are herein incorporated by reference in their entirety.

FIELD OF THE INVENTION

The invention relates to methods of using sodium channel modulators, particularly TTX-R sodium channel modulators and/or activity dependent sodium channel modulators, to treat gastrointestinal tract disorders, particularly inflammatory bowel disorders and irritable bowel syndrome.

BACKGROUND OF THE INVENTION

Gastrointestinal (GI) tract disorders affect the quality of life of millions of men and women in the United States every year. GI tract disorders may involve disturbances of the GI smooth muscle, epithelium, sensory afferent neurons, or central nervous system pathways. In spite of the uncertainty regarding whether central or peripheral mechanisms, or both, are involved in GI tract disorders, many proposed mechanisms implicate neurons and pathways that mediate visceral sensation. Viscerosensory information from the GI tract is relayed by sensory fibers that enter the spinal cord via the dorsal root ganglion (DRG) or project to the nodose ganglion via vagal afferents (*Physiology*, ed. R. M Berne and M. N. Levy, 1983, CV Mosby Co. St. Louis). A number of different subtypes of sensory afferent neurons may be involved in neurotransmission from the GI tract. These may be classified as, but not limited to, small diameter, medium diameter, large diameter, myelinated, unmyelinated, sacral, lumbar, DRG, vagal, nodose, peptidergic, non-peptidergic, IB4 positive, IB4 negative, C fiber, Aδ fiber, Aβ fiber, high threshold or low threshold neurons.

GI tract disorders have been characterized as structural (or mucosal) GI tract disorders and non-structural (or non-mucosal) GI tract disorders. Structural disorders include inflammatory bowel disorders and non-inflammatory structural GI tract disorders. Non-structural disorders include a variety of disorders classified as functional GI tract disorders.

Inflammatory bowel disorders include a group of disorders that can cause inflammation or ulceration of the GI tract. Ulcerative colitis and Crohn's disease are the most common types of inflammatory bowel disorders, although collagenous colitis, lymphocytic (microscopic) colitis, and other disorders have also been described.

Ulcerative colitis is a chronic inflammatory disorder of unknown etiology afflicting the large intestine and, except when very severe, is limited to the bowel mucosa. The course of this disorder may be continuous or relapsing and may be mild or severe. Medical treatment primarily includes the use of salicylate derivatives, glucocorticosteroids such as prednisone or prednisone acetate and anti-metabolites dependent on the clinical state of the patient. Salicylate derivatives, such as sulphazine or mesalamine, are efficacious in patients with mild cases of the disorder. Glucocorticosteroids and anti-metabolites are efficacious in patients with moderate or severe disease but are associated with a number of side effects. Patients who need chronic doses of glucocorticosteroids or anti-metabolites for control of their disorder eventually undergo removal of the colon surgically to eliminate the disease.

Like ulcerative colitis, Crohn's disease (also known as regional enteritis, ileitis, or granulomatous ileocolitis) is a chronic inflammatory disorder of unknown etiology; however the location and pathology of the disease differ. Crohn's disease typically presents in either the small intestine, large intestine or the combination of the two locations and can cause inflammation deeper into the muscle and serosa located within the intestinal wall. The course of the disorder may be continuous or relapsing and may be mild or severe. Medical treatment includes the continuous use of salicylate derivatives, glucocorticosteroids, anti-metabolites, and administration of an anti-TNF antibody. Many Crohn's disease patients require intestinal surgery for a problem related to the disease, but unlike ulcerative colitis subsequent relapse is common.

Collagenous colitis and lymphocytic colitis are idiopathic inflammatory disorders of the colon that cause watery diarrhea typically in middle-aged or older individuals. Lymphocytic colitis is distinguished from collagenous colitis by the absence of a thickened subepithelial collagenous layer. Bismuth in the form of Pepto-Bismol may be an effective treatment in some patients, although more severe cases may require the use of salicylate derivatives, antibiotics such as metronidazole, and glucocorticosteroids.

Functional GI tract disorders are characterized by presentation of abdominal-type symptoms without evidence of changes in metabolism or structural abnormalities. Disorders that are typically considered under functional disorders include dysphagia, non-ulcer dyspepsia, irritable bowel syndrome, slow-transit constipation, and evacuation disorders (Camilleri (2002) Gastrointestinal Motility Disorders, In *WebMD Scientific American Medicine*, edited by David C. Dale and Daniel D. Federman, New York, N.Y., WebMD). A prominent example of a functional GI tract disorder is irritable bowel syndrome (IBS), also known by a variety of synonyms, including functional bowel, pylorospasm, nervous indigestion, spastic colon, spastic colitis, spastic bowel, intestinal neurosis, functional colitis, irritable colon, mucous colitis, laxative colitis, and functional dyspepsia. IBS generally leads to abdominal pain and/or discomfort and an alteration in bowel habit with no clear etiology. Diagnosis relies on Rome criteria taking into account all symptoms related to patient presentation. (See, e.g., Drossman et al. (1997) *Gastroenterology*, 112: 2120). Patients typically present with symptoms consistent with hyperalgesia and allodynia.

At present, treatments for IBS have been largely ineffective, and have included stress management, diet, and drugs. Psychoactive drugs, such as anxiolytics and antidepressants, have been utilized but have limited utility because of the side effect profile. Antispasmodics and various antidiarrheal preparations have also been used but these remain as unsatisfactory remedies to patients with IBS.

Non-ulcer dyspepsia (NUD) is another prominent example of a functional GI tract disorder with no established etiology. Symptoms related to NUD include nausea, vomiting, pain, early satiety, bloating and loss of appetite.

Altered gastric emptying and increased gastric sensitivity and distress may contribute to NUD but do not completely explain its presentation. Treatments include behavioral therapy, psychotherapy, or administration of antidepressants, motility regulatory agents, antacids, $H_2$-receptor antagonists, and, prokinetics. However, many of these treatments have shown limited efficacy in many patients.

In addition to the structural/non-structural classification described above, GI tract disorders may also be sub-classified based upon anatomical, physiological, and other characteristics of different portions of the GI tract as described in Sleisenger and Fordtran's Gastrointestinal and Liver Disease, 6$^{th}$ Ed. (W.B. Saunders Co. 1998); K. M. Sanders (1996) *Gastroenterology*, 111: 492–515; P. Holzer (1998) *Gastroenterology*, 114: 823–839; and R. K. Montgomery et al. (1999) *Gastroenterology*, 116: 702–731. For example, acid peptic disorders are generally thought to arise from damage due to acidic and/or peptic activity of gastric secretions and may affect the esophagus, stomach, and duodenum. Acid peptic disorders include gastroesophageal reflux disease, peptic ulcers (both gastric and duodenal), erosive esophagitis and esophageal stricture. Zollinger-Ellison Syndrome may be considered an acid peptic disorder since it typically presents with multiple ulcers due to excessive acid secretion caused by a endocrine tumor. Treatments typically include gastric acid suppressive therapies, antibiotics, and surgery. In some patients, however, these therapies have proven ineffective.

Another sub-classification for GI tract disorders may be drawn between gastroesophageal and intestinal disorders based upon characteristics between different portions of the GI tract as disclosed in Sleisenger and Fordtran's Gastrointestinal and Liver Disease, 6$^{th}$ Ed. (W.B. Saunders Co. 1998); K. M. Sanders (1996) *Gastroenterology*, 111: 492–515; P. Holzer (1998) *Gastroenterology*, 114: 823–839; and R. K. Montgomery et al. (1999) *Gastroenterology*, 116: 702–731. Structural gastroesophageal disorders include disorders of the stomach and/or esophagus where there is no evidence of structural perturbations (including those observed in the mucosa) distal to the pylorus. Dyspepsia (chronic pain or discomfort centered in the upper abdomen) is a prominent feature of most structural gastroesophageal disorders but can also be observed in non-structural perturbations, and has been estimated to account for 2 to 5 percent of all general practice consultations. Structural gastroesophageal disorders include gastritis and gastric cancer. By contrast, Structural intestinal tract disorders occur in both the small intestine (the duodenum, jejunum, and ileum) and in the large intestine. Structural intestinal tract disorders are characterized by structural changes in the mucosa or in the muscle layers of the intestine, and include non-peptic ulcers of the small intestine, malignancies, and diverticulosis. Non-peptic ulcers in the small intestine are typically related to administration of non-steroidal anti-inflammatory drugs. Diverticulosis is a disorder that rarely occurs in the small intestine and most commonly appears in the colon.

Because existing therapies and treatments for GI tract disorders are associated with limitations as described above, new therapies and treatments are therefore desirable.

SUMMARY OF THE INVENTION

Compositions and methods for treating GI tract disorders, particularly inflammatory bowel disorders and irritable bowel syndrome, are provided. Compositions of the invention comprise sodium channel modulators, particularly tetrodotoxin-resistant (TTX-R) sodium channel modulators and/or activity-dependent sodium channel modulators as well as pharmaceutically acceptable, pharmacologically active salts, esters, amides, prodrugs, active metabolites, and other derivatives thereof. TTX-R sodium channel modulators for use in the present invention include but are not limited to compounds that modulate or interact with Nav1.8 and/or Nav1.9 channels.

The compositions are administered in therapeutically effective amounts to a patient in need thereof for treating GI tract disorders, particularly inflammatory bowel disorders and irritable bowel syndrome, in mammals, particularly humans. It is recognized that the compositions may be administered by any means of administration as long as an effective amount for the treatment of GI tract disorders is delivered. The compositions may be formulated, for example, for sustained, continuous, or as-needed administration.

BRIEF DESCRIPTION OF THE DRAWINGS

FIG. 1A depicts a typical response of a GI tract afferent neuron to lamotrigine under both slow and fast stimulation protocols. FIG. 1B shows summary data obtained from three neurons under control conditions and during application of 100 µM lamotrigine. Response amplitudes were normalized and mean±SEM are displayed.

FIG. 2A depicts a typical inward TTX-R sodium current recorded from a labeled GI tract afferent neuron before and during bath application of Ambroxol. FIG. 2B depicts a summary bar chart showing the combined effects of Ambroxol on GI tract afferent neurons. Peak inward current amplitudes were measured when the responses had reached a steady-state in the presence of drug. Response amplitudes were normalized and mean±SEM are displayed.

DETAILED DESCRIPTION OF THE INVENTION

Overview and Definitions

Figure 1:
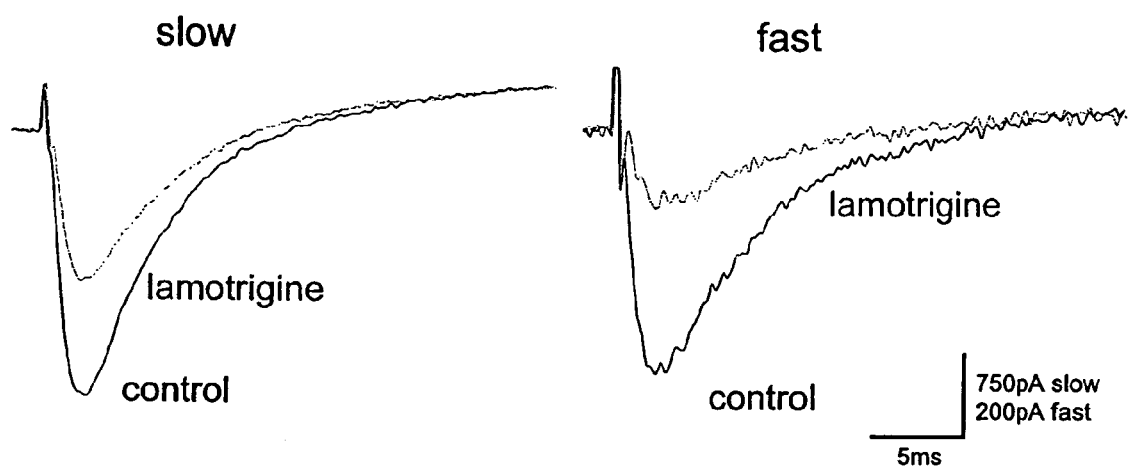
FIG. 1.
Figure 1:
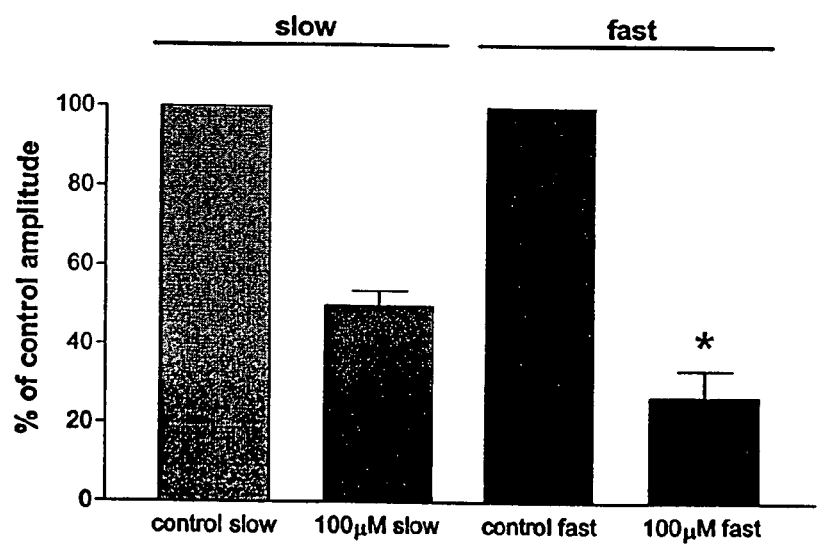

The present invention provides compositions and methods for treating GI tract disorders, including structural disorders (including inflammatory bowel disorders and structural intestinal disorders), and non-structural disorders (including functional GI tract disorders), but not acid-peptic disorders or gastroesophageal disorders. The compositions comprise a therapeutically effective dose of sodium channel modulators, particularly tetrodotoxin-resistant (TTX-R) sodium channel modulators and/or activity-dependent sodium channel modulators. The methods are accomplished by administering, for example, various compositions and formulations that contain quantities of a sodium channel modulator, particularly a tetrodotoxin-resistant (TTX-R) sodium channel modulator and/or activity-dependent sodium channel modulator.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

It must be noted that as used in this specification and the appended embodiments, the singular forms "a," an" and "the" include plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

The term "structural GI tract disorder" or "mucosal GI tract disorder" refers to any GI tract disorder related to structural or mucosal abnormalities of the GI tract or where there is evidence of a related metabolic disturbance, including but not limited to inflammatory bowel disorders, structural gastroesophageal disorders, and structural intestinal disorders.

By "inflammatory bowel disorder" is intended any disorder primarily associated with inflammation of the small and/or large intestine, including but not limited to ulcerative colitis, Crohn's disease, ileitis, proctitis, celiac disease (or non-tropical sprue), enteropathy associated with seronegative arthropathies, microscopic or collagenous colitis, eosinophilic gastroenteritis, or pouchitis resulting after proctocolectomy, and post ileoanal anastomosis.

"Crohn's disease" is used in its conventional sense to refer to gastrointestinal inflammation primarily of the small and large intestine, including disorders with fistulas or with extraintestinal manifestations, and encompasses all synonyms including regional enteritis, ileitis, and granulomatous ileocolitis.

"Proctitis" is used in its conventional sense to refer to inflammation of the rectal lining.

"Celiac disease" is used in its conventional sense to refer to any disorder primarily associated with altered sensitivity to gluten or gluten byproducts, with or without alterations in small bowel morphology (typically villus blunting) and encompasses all synonyms including celiac sprue and non-tropical sprue. Patients diagnosed with celiac disease may have symptomatic gluten intolerance with prominent diarrhea and abdominal pain or with minimal symptoms such as abdominal discomfort and associated dermatitis herpetiformis.

"Colitis" is used in its conventional sense to refer to inflammation of the large intestine.

"Ulcerative colitis" is used in its conventional sense to refer to inflammation and ulcers in the top layers of the lining of the large intestine and can be of any extent, including proctitis, proctosigmoiditis, left-sided colitis, or pan-colitis.

"Collagenous colitis" or "microscopic colitis" is used in its conventional sense to refer to an inflammatory disorder of unknown etiology with watery diarrhea as the leading symptom. A biopsy of the intestine typically demonstrates a thicker-than-normal layer of collagen (connective tissue) just beneath the inner surface of the colon (the epithelium) and/or inflammation of the epithelium and of the layer of connective tissue that lies beneath the epithelium. There is an association of arthritis with this disorder.

"Eosinophilic gastroenteritis" is used in its conventional sense to refer to a condition where a biopsy of the GI tract demonstrates infiltration with a type of white blood cell called eosinophils. There is no single cause of eosinophilic gastroenteritis and in many cases there is no known cause. Symptoms may include feeling full before finishing a meal, diarrhea, abdominal cramping or pain, nausea and vomiting. Asthma and allergies are sometimes related to the disorder.

"Pouchitis" is used in its conventional sense to refer to inflammation in a distal location of the intestine after a surgery on the intestine.

"Lymphocytic colitis" is used in its conventional sense to refer to inflammation of the large intestine without ulceration, and encompasses all synonyms including microscopic colitis.

The term "non-structural GI tract disorder" or "non-mucosal GI tract disorder" refers to any GI tract disorder not related to structural or mucosal abnormalities of the GI tract, nor where there is evidence of a related metabolic disturbance, including but not limited to functional GI tract disorders.

By "functional GI tract disorder" is intended any GI tract disorder associated with a disturbance of motor or sensory function in the absence of mucosal or structural damage or in the absence of a metabolic disorder. Functional GI tract disorders include functional dysphagia, non-ulcer dyspepsia, irritable bowel syndrome (IBS), slow-transit constipation and evacuation disorders.

By "non-ulcer dyspepsia" is intended any disorder associated with any abdominal symptom after eating including nausea, vomiting, pain, early satiety, bloating and loss of appetite where no ulceration in present in the esophagus, stomach or duodenum. Altered gastric emptying, increased gastric sensitivity and distress are considered as factors in the development of non-ulcer dyspepsia.

By "irritable bowel syndrome" or "IBS" is intended any disorder associated with abdominal pain and/or abdominal discomfort and an alteration in bowel habit, and encompasses all synonyms including functional bowel, pylorospasm, nervous indigestion, spastic colon, spastic colitis, spastic bowel, intestinal neurosis, functional colitis, irritable colon, mucous colitis, laxative colitis, and functional dyspepsia.

By "slow-transit constipation" is intended as a disorder with slowing of motility in the large intestine with a prolonged transit time through the organ.

By "evacuation disorders" is intended as any disorder where defecation occurs poorly and the patient is unable to expel stool.

By "acid peptic disorder" is intended any disorder associated with damage due to acidic and/or peptic activity of gastric secretions that affect the esophagus, stomach, and/or duodenum. Acid peptic disorders include gastroesophageal reflux disease, peptic ulcers (both gastric and duodenal), erosive esophagitis, esophageal strictures, and Zollinger-Ellison Syndrome.

GI tract disorders may divided between gastroesophageal and intestinal disorders based upon anatomical, physiological, and other characteristics of different portions of the GI tract as disclosed in Sleisenger and Fordtran's Gastrointestinal and Liver Disease, $6^{th}$ Ed. (W.B. Saunders Co. 1998); K. M. Sanders (1996) *Gastroenterology*, 111: 492–515; P. Holzer (1998) *Gastroenterology*, 114: 823–839; and R. K. Montgomery et al. (1999) *Gastroenterology*, 116: 702–731.

By "gastroesophageal" is intended all parts of the esophagus and stomach. By "gastroesophageal disorders" is intended any disorder involving the esophagus and/or duodenum. By "structural gastroesophageal disorder" is intended any disorder of the stomach and/or esophagus where there is no evidence of structural perturbations (including those observed in the mucosa) distal to the pylorus. Structural gastroesophageal disorders include gastric cancer and gastritis.

By "intestinal tract" is intended all parts of the duodenum, jejeunum, ileum and large intestine (or colon). By "intestinal tract disorder" is intended any disorder involving the duodenum, jejeunum, ileum, and large intestine (or colon). By "structural intestinal tract disorder" is intended any disorder involving the duodenum, jejeunum, ileum, and/or large intestine (or colon) where important mucosal and structural abnormalities are present or there is evidence of a related metabolic disturbance that is not an inflammatory bowel disorder or an acid peptic disorder. Structural intestinal disorders include ulcers typically related to medications such as non-steroidal anti-inflammatory drugs, malignancies, and diverticulosis.

By "small intestine" is intended all parts of the duodenum, jejunum, and ileum.

The term "duodenum" is used in its conventional sense to refer to that portion of the GI tract beginning at the pylorus and ending at the ligament of Treitz. The duodenum is divided into four parts. (See, e.g., Yamada (1999) Textbook of Gastroenterology 3d Ed., Lippincott Williams & Wilkins). The first part of the duodenum is also known as the superior portion of the duodenum, and begins at the pylorus, is about 5 cm long, and passes backward and upward beneath the liver to the neck of the gall bladder (the first 2–3 cm of which is the duodenal bulb). The second part of the duodenum is also known as the descending portion of the duodenum, and extends along the right margin of the head of the pancreas, and is approximately 7 to 10 cm in length. The third part of the duodenum is also known as the horizontal portion of the duodenum, and is where the duodenum passes from right to left across the spine, inclining upwards for about 5 to 8 cm. The fourth part of the duodenum is also known as the ascending portion of the duodenum and begins at the left of the vertebral column, ascends to the left of the aorta for 2 to 3 cm and ends at the ligament of Treitz.

The terms "active agent" and "pharmacologically active agent" are used interchangeably herein to refer to a chemical compound that induces a desired effect, i.e., in this case, treatment of GI tract disorders except for acid peptic disorders or structural gastroesophageal disorders. The primary active agents herein are compounds that interact with TTX-R sodium channels, including but not limited to sodium channel modulators, particularly tetrodotoxin-resistant (TTX-R) sodium channel modulators and/or activity-dependent sodium channel modulators, including compounds that modulate or interact with Nav1.8 and/or Nav1.9 channels. In addition, a combination therapy wherein a sodium channel modulator, particularly a tetrodotoxin-resistant (TTX-R) sodium channel modulator and/or activity-dependent sodium channel modulator compound that interacts with TTX-R sodium channels is administered with one or more additional active agents is also within the scope of the present invention. Such combination therapy may be carried out by administration of the different active agents in a single composition, by concurrent administration of the different active agents in different compositions, or by sequential administration of the different active agents. Included are and salts, enantiomers, analogs, esters, amides, prodrugs, active metabolites, and derivatives of those compounds or classes of compounds specifically mentioned that also induce the desired effect.

The term "sodium channel modulator" as used herein is intended to include agents that interact with the channel pore itself (e.g., a binding event), or that may act as an allosteric modulator of the channel by interacting with a site on the channel complex (e.g., a binding event), as well as salts, esters, amides, prodrugs, active metabolites, and other derivatives thereof. Further, it is understood that any salts, enantiomers, analogs, esters, amides, prodrugs, metabolites, or derivatives are pharmaceutically acceptable as well as pharmacologically active.

The term TTX-R sodium channel modulator as used herein is intended to include agents that interact with TTX-R sodium channels and/or any protein associated with a TTX-R sodium channels (e.g., a binding event) to produce a physiological effect, such as opening, closing, blocking, up-regulating expression, or down-regulating expression of the channel, but not antisense or knockout technologies. "Agents that interact with TTX-R sodium channels and/or any protein associated with a TTX-R sodium channel" include but are not limited to, amino acid compounds, peptide, nonpeptide, peptidomimetic, small molecular weight organic compounds, and other compounds that modulate or interact with TTX-R sodium channels (e.g., a binding event) or proteins associates with TTX-R sodium channels (e.g., a binding event) such as anchor proteins, as well as salts, esters, amides, prodrugs, active metabolites, and other derivatives thereof. "Agents that interact with TTX-R sodium channels and/or any protein associated with a TTX-R sodium channel" also include but are not limited to, amino acid compounds, peptide, nonpeptide, peptidomimetic, small molecular weight organic compounds, and other compounds that modulate or interact with Nav1.8 and/or Nav1.9 channels (e.g., a binding event) or proteins associated with Nav1.8 and/or Nav1.9 channels (e.g., a binding event), such as anchor proteins, as well as salts, esters, amides, prodrugs, active metabolites, and other derivatives thereof. Further, it is understood that any salts, enantiomers, analogs, esters, amides, prodrugs, metabolites, or derivatives are pharmaceutically acceptable as well as pharmacologically active.

The term "activity-dependent sodium channel modulator" or "use-dependent sodium channel modulator" as used herein is intended an agent that preferentially modulates the activity of a sodium channel that has been activated or opened, and exhibits its effect either by modifying the activity of the open channel, or by modifying the activity of the inactivated state of the channel as described in Hille B. (1992) Ionic Channels in Excitable Membranes. 2nd ed. Sinauer Associates, Sunderland, Mass., pp. 390–422. Unless otherwise indicated, the term "activity-dependent sodium channel modulator" is intended to include agents that interact with the channel pore itself (e.g., a binding event), or that may act as an allosteric modulator of the channel by interacting with a site on the channel complex (e.g., a binding event), as well as salts, esters, amides, prodrugs, active metabolites, and other derivatives thereof. Further, it is understood that any salts, enantiomers, analogs, esters, amides, prodrugs, metabolites, or derivatives are pharmaceutically acceptable as well as pharmacologically active.

The term "peptidomimetic" is used in its conventional sense to refer to a molecule that mimics the biological activity of a peptide but is no longer peptidic in chemical nature, including molecules that lack amide bonds between amino acids, as well as pseudo-peptides, semi-peptides and peptoids. Peptidomimetics according to this invention provide a spatial arrangement of reactive chemical moieties that closely resembles the three-dimensional arrangement of active groups in the peptide on which the peptidomimetic is based. As a result of this similar active-site geometry, the peptidomimetic has effects on biological systems that are similar to the biological activity of the peptide.

The term "anticholinergic agent" as used herein refers to any acetylcholine receptor antagonist, including antagonists of nicotinic and/or muscarinic acetylcholine receptors. The term "antinicotinic agent" as used herein is intended any nicotinic acytylcholine receptor antagonist. The term "antimuscarinic agent" as used herein is intended any muscarinic acetylcholine receptor antagonist. Unless otherwise indicated, the terms "anticholinergic agent," "antinicotinic agent," and "antimuscarinic agent" are intended to include anticholinergic, antinicotinic, and antimuscarinic agents as disclosed further herein, as well as salts, esters, amides, prodrugs, active metabolites, and other derivatives thereof. Further, it is understood that any salts, enantiomers, analogs, esters, amides, prodrugs, metabolites, or derivatives are pharmaceutically acceptable as well as pharmacologically active.

The term "β3 adrenergic agonist" is used in its conventional sense to refer to a compound that agonizes β3 adrenergic receptors. Unless otherwise indicated, the term "β3 adrenergic agonist" is intended to include β3 adrenergic agonist agents as disclosed further herein, as well as salts, esters, amides, prodrugs, active metabolites, and other derivatives thereof. Further, it is understood that any salts, enantiomers, analogs, esters, amides, prodrugs, metabolites, or derivatives are pharmaceutically acceptable as well as pharmacologically active.

The term "spasmolytic" (also known as "antispasmodic") is used in its conventional sense to refer to a compound that relieves or prevents muscle spasms, especially of smooth muscle. Unless otherwise indicated, the term "spasmolytic" is intended to include spasmolytic agents as disclosed further herein, as well as salts, esters, amides, prodrugs, active metabolites, and other derivatives thereof. Further, it is understood that any salts, enantiomers, analogs, esters, amides, prodrugs, metabolites, or derivatives are pharmaceutically acceptable as well as pharmacologically active.

The term "neurokinin receptor antagonist" is used in its conventional sense to refer to a compound that antagonizes neurokinin receptors. Unless otherwise indicated, the term "neurokinin receptor antagonist" is intended to include neurokinin receptor antagonist agents as disclosed further herein, as well as salts, esters, amides, prodrugs, active metabolites, and other derivatives thereof. Further, it is understood that any salts, enantiomers, analogs, esters, amides, prodrugs, metabolites, or derivatives are pharmaceutically acceptable as well as pharmacologically active.

The term "bradykinin receptor antagonist" is used in its conventional sense to refer to a compound that antagonizes bradykinin receptors. Unless otherwise indicated, the term "bradykinin receptor antagonist" is intended to include bradykinin receptor antagonist agents as disclosed further herein, as well as salts, esters, amides, prodrugs, active metabolites, and other derivatives thereof. Further, it is understood that any salts, enantiomers, analogs, esters, amides, prodrugs, metabolites, or derivatives are pharmaceutically acceptable as well as pharmacologically active.

The term "nitric oxide donor" is used in its conventional sense to refer to a compound that releases free nitric oxide when administered to a patient. Unless otherwise indicated, the term "nitric oxide donor" is intended to include nitric oxide donor agents as disclosed further herein, as well as salts, esters, amides, prodrugs, active metabolites, and other derivatives thereof. Further, it is understood that any salts, enantiomers, analogs, esters, amides, prodrugs, metabolites, or derivatives are pharmaceutically acceptable as well as pharmacologically active.

The terms "treating" and "treatment" as used herein refer to relieving the symptoms or lessening the discomfort associated with GI tract disorders except for acid peptic disorders or structural gastroesophageal disorders.

By an "effective" amount or a "therapeutically effective amount" of a drug or pharmacologically active agent is meant a nontoxic but sufficient amount of the drug or agent to provide the desired effect, i.e., relieving the symptoms or lessening the discomfort associated with GI tract disorders except for acid peptic disorders or structural gastroesophageal disorders.

By "pharmaceutically acceptable," such as in the recitation of a "pharmaceutically acceptable carrier," or a "pharmaceutically acceptable acid addition salt," is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. "Pharmacologically active" (or simply "active") as in a "pharmacologically active" derivative or metabolite, refers to a derivative or metabolite having the same type of pharmacological activity as the parent compound. When the term "pharmaceutically acceptable" is used to refer to a derivative (e.g., a salt or an analog) of an active agent, it is to be understood that the compound is pharmacologically active as well, i.e., therapeutically effective for treating GI tract disorders except for acid peptic disorders or structural gastroesophageal disorders, in mammals, particularly humans.

By "continuous" dosing is meant the chronic administration of a selected active agent. By "as-needed" dosing, also known as "pro re nata" "prn" dosing, and "on demand" dosing or administration is meant the administration of a single dose of the active agent at some time prior to commencement of an activity wherein suppression of the symptoms of a GI tract disorder except for acid peptic disorders or structural gastroesophageal disorders, would be desirable. Administration can be immediately prior to such an activity, including about 0 minutes, about 10 minutes, about 20 minutes, about 30 minutes, about 1 hour, about 2 hours, about 3 hours, about 4 hours, about 5 hours, about 6 hours, about 7 hours, about 8 hours, about 9 hours, or about 10 hours prior to such an activity, depending on the formulation.

By "short-term" is intended any period of time up to and including about 8 hours, about 7 hours, about 6 hours, about 5 hours, about 4 hours, about 3 hours, about 2 hours, about 1 hour, about 40 minutes, about 20 minutes, or about 10 minutes after drug administration.

By "rapid-offset" is intended any period of time up to and including about 8 hours, about 7 hours, about 6 hours, about 5 hours, about 4 hours, about 3 hours, about 2 hours, about 1 hour, about 40 minutes, about 20 minutes, or about 10 minutes after drug administration.

The term "controlled release" is intended to refer to any drug-containing formulation in which release of the drug is not immediate, i.e., with a "controlled release" formulation, oral administration does not result in immediate release of the drug into an absorption pool. The term is used interchangeably with "non-immediate release" as defined in Remington: The Science and Practice of Pharmacy, Twentieth Ed. (Philadelphia, Pa.: Lippincott Williams & Wilkins, 2000).

The "absorption pool" represents a solution of the drug administered at a particular absorption site, and $k_r$, $k_a$, and $k_e$ are first-order rate constants for: 1) release of the drug from the formulation; 2) absorption; and 3) elimination, respectively. For immediate release dosage forms, the rate constant for drug release $k_r$ is far greater than the absorption rate constant $k_a$. For controlled release formulations, the opposite is true, i.e., $k_r \lll k_a$, such that the rate of release of drug from the dosage form is the rate-limiting step in the delivery of the drug to the target area. The term "controlled release" as used herein includes any nonimmediate release formulation, including but not limited to sustained release, delayed release and pulsatile release formulations.

The term "sustained release" is used in its conventional sense to refer to a drug formulation that provides for gradual release of a drug over an extended period of time, and that preferably, although not necessarily, results in substantially constant blood levels of a drug over an extended time period such as up to about 72 hours, about 66 hours, about 60 hours, about 54 hours, about 48 hours, about 42 hours, about 36 hours, about 30 hours, about 24 hours, about 18 hours, about 12 hours, about 10 hours, about 8 hours, about 7 hours, about 6 hours, about 5 hours, about 4 hours, about 3 hours, about 2 hours, or about 1 hour after drug administration.

The term "delayed release" is used in its conventional sense to refer to a drug formulation that provides for an initial release of the drug after some delay following drug administration and that preferably, although not necessarily, includes a delay of up to about 10 minutes, about 20 minutes, about 30 minutes, about 1 hour, about 2 hours, about 3 hours, about 4 hours, about 5 hours, about 6 hours, about 7 hours, about 8 hours, about 9 hours, about 10 hours, about 11 hours, or about 12 hours.

The term "pulsatile release" is used in its conventional sense to refer to a drug formulation that provides release of the drug in such a way as to produce pulsed plasma profiles of the drug after drug administration. The term "immediate release" is used in its conventional sense to refer to a drug formulation that provides for release of the drug immediately after drug administration.

The term "immediate release" is used in its conventional sense to refer to a drug formulation that provides for release of the drug immediately after drug administration.

By the term "transdermal" drug delivery is meant delivery by passage of a drug through the skin or mucosal tissue and into the bloodstream.

The term "topical administration" is used in its conventional sense to mean delivery of a topical drug or pharmacologically active agent to the skin or mucosa.

The term "oral administration" is used in its conventional sense to mean delivery of a drug through the mouth and ingestion through the stomach and digestive tract.

The term "inhalation administration" is used in its conventional sense to mean delivery of an aerosolized form of the drug by passage through the nose or mouth during inhalation and passage of the drug through the walls of the lungs.

By the term "parenteral" drug delivery is meant delivery by passage of a drug into the blood stream without first having to pass through the alimentary canal, or digestive tract. Parenteral drug delivery may be "subcutaneous," referring to delivery of a drug by administration under the skin. Another form of parenteral drug delivery is "intramuscular," referring to delivery of a drug by administration into muscle tissue. Another form of parenteral drug delivery is "intradermal," referring to delivery of a drug by administration into the skin. An additional form of parenteral drug delivery is "intravenous," referring to delivery of a drug by administration into a vein. An additional form of parenteral drug delivery is "intra-arterial," referring to delivery of a drug by administration into an artery. Another form of parenteral drug delivery is "transdermal," referring to delivery of a drug by passage of the drug through the skin and into the bloodstream.

Still another form of parenteral drug delivery is "transmucosal," referring to administration of a drug to the mucosal surface of an individual so that the drug passes through the mucosal tissue and into the individual's blood stream. Transmucosal drug delivery may be "buccal" or "transbuccal," referring to delivery of a drug by passage through an individual's buccal mucosa and into the bloodstream. Another form of transmucosal drug delivery herein is "lingual" drug delivery, which refers to delivery of a drug by passage of a drug through an individual's lingual mucosa and into the bloodstream. Another form of transmucosal drug delivery herein is "sublingual" drug delivery, which refers to delivery of a drug by passage of a drug through an individual's sublingual mucosa and into the bloodstream. Another form of transmucosal drug delivery is "nasal" or "intranasal" drug delivery, referring to delivery of a drug through an individual's nasal mucosa and into the bloodstream. An additional form of transmucosal drug delivery herein is "rectal" or "transrectal" drug delivery, referring to delivery of a drug by passage of a drug through an individual's rectal mucosa and into the bloodstream. Another form of transmucosal drug delivery is "urethral" or "transurethral" delivery, referring to delivery of the drug into the urethra such that the drug contacts and passes through the wall of the urethra. An additional form of transmucosal drug delivery is "vaginal" or "transvaginal" delivery, referring to delivery of a drug by passage of a drug through an individual's vaginal mucosa and into the bloodstream. An additional form of transmucosal drug delivery is "perivaginal" delivery, referring to delivery of a drug through the vaginolabial tissue into the bloodstream.

In order to carry out the method of the invention, a selected active agent is administered to a patient suffering from a GI tract disorder except for acid peptic disorders or structural gastroesophageal disorders. A therapeutically effective amount of the active agent may be administered orally, intravenously, subcutaneously, transmucosally (including buccally, sublingually, transurethrally, and rectally), topically, transdermally, by inhalation, or using any other route of administration.

GI Tract Disorders

GI tract disorders affect the quality of life of millions of men and women in the United States every year. GI tract disorders may involve disturbances of the GI smooth muscle, epithelium, sensory afferent neurons, or central nervous system pathways. In spite of the uncertainty regarding whether central or peripheral mechanisms, or both, are involved in GI tract disorders, many proposed mechanisms implicate neurons and pathways that mediate visceral sensation. Viscerosensory information from the GI tract is relayed by sensory fibers that enter the spinal cord via the dorsal root ganglion (DRG) or project to the nodose ganglion via vagal afferents (*Physiology*, ed. R. M Berne and M. N. Levy, 1983, CV Mosby Co. St. Louis). A number of different subtypes of sensory afferent neurons may be involved in neurotransmission from the GI tract. These may be classified as, but not limited to, small diameter, medium diameter, large diameter, myelinated, unmyelinated, sacral, lumbar, DRG, vagal, nodose, peptidergic, non-peptidergic, IB4 positive, IB4 negative, C fiber, Aδ fiber, Aβ fiber, high threshold or low threshold neurons.

Structural and Non-Structural GI Tract Disorders

GI tract disorders have been characterized as structural (or mucosal) GI tract disorders and non-structural (or non-mucosal) GI tract disorders. Structural disorders include inflammatory bowel disorders and non-inflammatory structural GI tract disorders. Non-structural disorders include a variety of disorders classified as functional GI tract disorders.

Inflammatory bowel disorders include a group of disorders that can cause inflammation or ulceration of the GI tract. Ulcerative colitis and Crohn's disease are the most common types of inflammatory bowel disorders, although collagenous colitis, lymphocytic (microscopic) colitis, and other disorders have also been described.

The compounds of the present invention are useful in the treatment of ulcerative colitis. Ulcerative colitis is a chronic inflammatory disorder of unknown etiology afflicting the large intestine and, except when very severe, is limited to the bowel mucosa. The course of this disorder may be continuous or relapsing and may be mild or severe. Medical treatment primarily includes the use of salicylate derivatives, glucocorticosteroids such as prednisone or prednisone acetate and anti-metabolites dependent on the clinical state of the patient. Salicylate derivatives, such as sulphazine or mesalamine, are efficacious in patients with mild cases of the disorder. Glucocorticosteroids and anti-metabolites are efficacious in patients with moderate or severe disease but are associated with a number of side effects. Patients who need chronic doses of glucocorticosteroids or anti-metabolites for control of their disorder eventually undergo removal of the colon surgically to eliminate the disease. Therefore, the compounds of the present invention meet an existing need for new treatments for ulcerative colitis.

The compounds of the present invention are also useful for in the treatment of Chron's disease. Like ulcerative colitis, Crohn's disease (also known as regional enteritis, ileitis, or granulomatous ileocolitis) is a chronic inflammatory disorder of unknown etiology; however the location and pathology of the disease differ. Crohn's disease typically presents in either the small intestine, large intestine or the combination of the two locations and can cause inflammation deeper into the muscle and serosa located within the intestinal wall. The course of the disorder may be continuous or relapsing and may be mild or severe. Medical treatment includes the continuous use of salicylate derivatives, glucocorticosteroids, anti-metabolites, and administration of an anti-TNF antibody. Many Crohn's disease patients require intestinal surgery for a problem related to the disease, but unlike ulcerative colitis subsequent relapse is common. Therefore, the compounds of the present invention meet an existing need for new treatments for Chron's disease.

Compounds of the present invention are also useful in the treatment of collagenous colitis and lymphocytic colitis. Collagenous colitis and lymphocytic colitis are idiopathic inflammatory disorders of the colon that cause watery diarrhea typically in middle-aged or older individuals. Lymphocytic colitis is distinguished from collagenous colitis by the absence of a thickened subepithelial collagenous layer. Bismuth in the form of Pepto-Bismol may be an effective treatment in some patients, although more severe cases may require the use of salicylate derivatives, antibiotics such as metronidazole, and glucocorticosteroids. Therefore, the compounds of the present invention meet an existing need for new treatments for collagenous colitis and lymphocytic colitis.

Compounds of the present invention are also useful in the treatment of functional GI tract disorders. Functional GI tract disorders are characterized by presentation of abdominal-type symptoms without evidence of changes in metabolism or structural abnormalities. Disorders that are typically considered under functional disorders include dysphagia, non-ulcer dyspepsia, irritable bowel syndrome, slow-transit constipation, and evacuation disorders (Camilleri (2002) Gastrointestinal Motility Disorders, In *WebMD Scientific American Medicine*, edited by David C. Dale and Daniel D. Federman, New York, N.Y., WebMD). A prominent example of a functional GI tract disorder is irritable bowel syndrome (IBS), also known by a variety of synonyms, including functional bowel, pylorospasm, nervous indigestion, spastic colon, spastic colitis, spastic bowel, intestinal neurosis, functional colitis, irritable colon, mucous colitis, laxative colitis, and functional dyspepsia. IBS generally leads to abdominal pain and/or discomfort and an alteration in bowel habit with no clear etiology. Diagnosis relies on Rome criteria taking into account all symptoms related to patient presentation. (See, e.g., Drossman et al. (1997) *Gastroenterology*, 112: 2120). Patients typically present with symptoms consistent with hyperalgesia and allodynia.

Compounds of the present invention are also useful in the treatment of IBS. At present, treatments for IBS have been largely ineffective, and have included stress management, diet, and drugs. Psychoactive drugs, such as anxiolytics and antidepressants, have been utilized but have limited utility because of the side effect profile. Antispasmodics and various antidiarrheal preparations have also been used but these remain as unsatisfactory remedies to patients with IBS. Therefore, the compounds of the present invention meet an existing need for new treatments for IBS.

Compounds of the present invention are also useful in the treatment of non-ulcer dyspepsia. Non-ulcer dyspepsia (NUD) is another prominent example of a functional GI tract disorder with no established etiology. Symptoms related to NUD include nausea, vomiting, pain, early satiety, bloating and loss of appetite. Altered gastric emptying and increased gastric sensitivity and distress may contribute to NUD but do not completely explain its presentation. Treatments include behavioral therapy, psychotherapy, or administration of antidepressants, motility regulatory agents, antacids, $H_2$-receptor antagonists, and prokinetics. However, many of these treatments have shown limited efficacy in many patients. Therefore, the compounds of the present invention meet an existing need for new treatments for NUD.

Anatomical and Physiological Distinctions

In addition to the structural/non-structural classification described above, GI tract disorders may also be sub-classified based upon anatomical, physiological, and other characteristics of different portions of the GI tract as described in Sleisenger and Fordtran's Gastrointestinal and Liver Disease, 6$^{th}$ Ed. (W.B. Saunders Co. 1998); K. M. Sanders (1996) *Gastroenterology*, 111: 492–515; P. Holzer (1998) *Gastroenterology*, 114: 823–839; and R. K. Montgomery et al. (1999) *Gastroenterology*, 116: 702–731. For example, acid peptic disorders are generally thought to arise from damage due to acidic and/or peptic activity of gastric secretions and may affect the esophagus, stomach, and duodenum. Acid peptic disorders include gastroesophageal reflux disease, peptic ulcers (both gastric and duodenal), erosive esophagitis and esophageal stricture. Zollinger-Ellison Syndrome may be considered an acid peptic disorder since it typically presents with multiple ulcers due to excessive acid secretion caused by a endocrine tumor. Treatments typically include gastric acid suppressive therapies, antibiotics, and surgery. In some patients, however, these therapies have proven ineffective. Therefore, the compounds of the present invention meet an existing need for new treatments for acid peptic disorders.

Another sub-classification for GI tract disorders may be drawn between gastroesophageal and intestinal disorders based upon characteristics between different portions of the GI tract as disclosed in Sleisenger and Fordtran's Gastrointestinal and Liver Disease, 6$^{th}$ Ed. (W.B. Saunders Co. 1998); K. M. Sanders (1996) *Gastroenterology*, 111:

492–515; P. Holzer (1998) *Gastroenterology*, 114: 823–839; and R. K. Montgomery et al. (1999) *Gastroenterology*, 116: 702–731. Structural gastroesophageal disorders include disorders of the stomach and/or esophagus where there is no evidence of structural perturbations (including those observed in the mucosa) distal to the pylorus. Dyspepsia (chronic pain or discomfort centered in the upper abdomen) is a prominent feature of most structural gastroesophageal disorders but can also be observed in non-structural perturbations, and has been estimated to account for 2 to 5 percent of all general practice consultations. Structural gastroesophageal disorders include gastritis and gastric cancer. By contrast, structural intestinal tract disorders occur in both the small intestine (the duodenum, jejunum, and ileum) and in the large intestine. Structural intestinal tract disorders are characterized by structural changes in the mucosa or in the muscle layers of the intestine, and include non-peptic ulcers of the small intestine, malignancies, and diverticulosis. Non-peptic ulcers in the small intestine are typically related to administration of non-steroidal anti-inflammatory drugs. Diverticulosis is a disorder that rarely occurs in the small intestine and most commonly appears in the colon.

The compounds of the present invention are useful in the treatment of both gastroesophageal and intestinal disorders.

Non-Inflammatory GI Tract Disorders

The compounds of the present invention are useful in the treatment of non-inflammatory GI disorders. Non-inflammatory GI tract disorders include non-inflammatory structural GI tract disorders and non-structural GI tract disorders. Non-inflammatory structural GI tract disorders include, but are not limited to, hiatal hernias, strictures, esophageal webs, Schatzki's ring, esophageal diverticula, and esophageal scleroderma. Non-structural GI tract disorders include motor disorders of the esophagus such as achalasia and diffuse esophageal spasm, and functional GI tract disorders such as irritable bowel syndrome.

Hiatal (also called hiatus) hernias may be divided into two types: sliding and paraesophageal. (*First Principles of Gastroenterology, The basis of disease and an approach to management* (2000), 4$^{th}$ edition, Thompson A B R and Shaffer E A, eds., Canadian Association of Gastroenterology and AstraZeneca). A sliding hiatal hernia is relatively common and occurs where a circumferential cuff of cardia and proximal stomach migrates into the thorax through the diaphragmatic hiatus. (See, e.g., Thompson and Shaffer, *First Principles of Gastroenterology*, supra). The etiology of sliding hiatal hernias is unclear, and they often reduce and reform spontaneously, although surgical correction may be performed in extreme cases. (See, e.g., Thompson and Shaffer, *First Principles of Gastroenterology*, supra). By contrast, paraesophageal hiatal hernias are relatively uncommon and occur where the fundus of the stomach migrates through the hiatus alongside the esophagus without any displacement of the gastroesophageal junction. (See, e.g., Thompson and Shaffer, *First Principles of Gastroenterology*, supra). The etiology of paraesophageal hiatal hernias is also unclear. Paraesophageal hiatal hernias are often asymptomatic, but many are treated surgically because the herniated portion may become strangulated and infarcted. (See, e.g., Thompson and Shaffer, *First Principles of Gastroenterology*, supra). The compounds of the present invention are useful in the treatment of hiatal hernias.

The compounds of the present invention are useful in the treatment of strictures. A stricture is a narrowing of the GI tract. An esophageal stricture is a narrowing of the esophagus.

The compounds of the present invention are also useful in the treatment of esophageal webs. Esophageal webs are thin, membrane-like structures that project into the esophageal lumen, are covered on both sides with squamous epithelium, and are most commonly found in the cervical esophagus. (See, e.g., Thompson and Shaffer, *First Principles of Gastroenterology*, supra). Esophageal webs rarely occlude enough of the esophageal lumen to cause dysphagia and are usually detected incidentally during barium x-rays. (See, e.g., Thompson and Shaffer, *First Principles of Gastroenterology*, supra). Although some esophageal webs may be congenital in origin, others may form after esophageal injury. (See, e.g., Thompson and Shaffer, *First Principles of Gastroenterology*, supra). The precise etiology of esophageal webs is unclear. (See, e.g., Thompson and Shaffer, *First Principles of Gastroenterology*, supra).

The compounds of the present invention are also useful in the treatment of Schatzki's ring. Like esophageal webs, Schatzki's ring is also a membrane-like structure. (See, e.g., Thompson and Shaffer, *First Principles of Gastroenterology*, supra). Unlike webs, however, Schatzki's ring is lined by squamous epithelium on its superior aspect and columnar epithelium inferiorly. (See, e.g., Thompson and Shaffer, *First Principles of Gastroenterology*, supra). Schatzki's ring rarely occludes enough of the esophageal lumen to cause dysphagia, but are detected incidentally in up to 10% of all upper GI barium x-rays. (See, e.g., Thompson and Shaffer, *First Principles of Gastroenterology*, supra). Where dysphagia occurs, however, Schatzki's ring is a common cause. (See, e.g., Thompson and Shaffer, *First Principles of Gastroenterology*, supra). Treatment of symptomatic Schatzki's ring involves shattering the ring with a large-diameter bougie or a balloon dilator. (See, e.g., Thompson and Shaffer, *First Principles of Gastroenterology*, supra). Therefore, the compounds of the present invention meet an existing need for new treatments for Schatzki's ring.

The compounds of the present invention are useful in the treatment of esophageal diverticula. Esophageal diverticula are outpouchings of one or more layers of the esophageal wall, and include midesophageal and lower esophageal diverticula.

Midesophageal diverticula (also called "traction" diverticula) were once thought to arise secondary to old mediastinal inflammation, such as tuberculosis, that caused adherence of mediastinal structures to the outer esophageal wall. (See, e.g., Thompson and Shaffer, *First Principles of Gastroenterology*, supra). Recent evidence suggests that very few midesophageal diverticula arise this way, but are instead associated with a motility disorder. (See, e.g., Thompson and Shaffer, *First Principles of Gastroenterology*, supra). In fact, it is likely that midesophageal diverticula are actually "pulsion" diverticula formed when a peristaltic wave deteriorates into a simultaneous or spastic contraction in the smooth-muscle esophagus. (See, e.g., Thompson and Shaffer, *First Principles of Gastroenterology*, supra). Midesophageal diverticula rarely require specific therapy, although the associated motor disorder may require treatment if symptomatic. (See, e.g., Thompson and Shaffer, *First Principles of Gastroenterology*, supra). Therefore, the compounds of the present invention meet an existing need for new treatments for midesophageal diverticula.

Lower esophageal diverticula are also "pulsion" diverticula, and form just above the lower esophageal sphincter. (See, e.g., Thompson and Shaffer, *First Principles of Gastroenterology*, supra). Lower esophageal diverticula are invariably associated with an esophageal motor disorder, and patients usually present with dysphagia and/or anginalike chest pain. (See, e.g., Thompson and Shaffer, *First Principles of Gastroenterology*, supra). Patients may also complain of nocturnal regurgitation of large quantities of stagnant fluid. (See, e.g., Thompson and Shaffer, *First Principles of Gastroenterology*, supra). Current treatment options include the use of nitrates and some calcium channel blockers, although esophageal myotomy may be an option for patients with severe disease unresponsive to medical measures. (See, e.g., Thompson and Shaffer, *First Principles of Gastroenterology*, supra). Therefore, the compounds of the present invention meet an existing need for new treatments for lower esophageal diverticula.

The compounds of the present invention are also useful in the treatment of esophageal scleroderma. Esophageal scleroderma often occurs in patients with general scleroderma, and may be present even in the absence of obvious skin and joint involvement. (See, e.g., Thompson and Shaffer, *First Principles of Gastroenterology*, supra). Initial damage involves small blood vessels, which leads to intramural neuronal dysfunction and ultimately to actual muscle damage and fibrosis. (See, e.g., Thompson and Shaffer, *First Principles of Gastroenterology*, supra). These effects produce a very hypotensive lower esophageal sphincter and weak non-propulsive esophageal contractions. (See, e.g., Thompson and Shaffer, *First Principles of Gastroenterology*, supra). Scleroderma may also involve the stomach and cause delayed gastric emptying as well as gastroesophageal reflux. (See, e.g., Thompson and Shaffer, *First Principles of Gastroenterology*, supra). Patients may report dysphagia, which can be due to poor esophageal propulsion and/or reflux-induced stricture. (See, e.g., Thompson and Shaffer, *First Principles of Gastroenterology*, supra). Such patients need very aggressive treatment for gastroesophageal reflux, but because of very poor peristaltic function, anti-reflux surgery may markedly worsen the dysphagia by increasing the barrier at the lower esophageal sphincter. (See, e.g., Thompson and Shaffer, *First Principles of Gastroenterology*, supra). Therefore, the compounds of the present invention meet an existing need for new treatments for esophageal scleroderma.

The compounds of the present invention are also useful in the treatment of motor disorders of the esophagus. Motor disorders of the esophagus may be classified as primary or secondary. Primary motor disorders of the esophagus usually affect the esophagus alone and have no known etiology. (See, e.g., Thompson and Shaffer, *First Principles of Gastroenterology*, supra). By contrast, secondary motor disorders of the esophagus are motility disturbances caused by some other systemic or local condition, including acid-reflux-induced dysmotility and dysmotility related to diabetic neuropathy. (See, e.g., Thompson and Shaffer, *First Principles of Gastroenterology*, supra).

Primary motor disorders of the esophagus include diffuse esophageal spasm (DES) and achalasia. (See, e.g., Thompson and Shaffer, *First Principles of Gastroenterology*, supra). DES is characterized by normal peristalsis interrupted by frequent high-pressure non-propagated (or "tertiary") waves as well as multi-peaked waves, with patients often presenting with dysphagia and chest pain. (See, e.g., Thompson and Shaffer, *First Principles of Gastroenterology*, supra). In advanced DES, an x-ray examination shows a corkscrew pattern due to different portions of the esophagus vigorously and simultaneously contracting. (See, e.g., Thompson and Shaffer, *First Principles of Gastroenterology*, supra). Although unknown, the etiology of DES may relate to degenerative changes in the intrinsic and extrinsic esophageal nerves. (See, e.g., Thompson and Shaffer, *First Principles of Gastroenterology*, supra). Current treatment options include the use of nitrates and some calcium channel blockers, although long esophageal myotomy may be an option for patients with severe disease unresponsive to medical measures. (See, e.g., Thompson and Shaffer, *First Principles of Gastroenterology*, supra). Therefore, the compounds of the present invention meet an existing need for new treatments for DES.

Achalasia is a relatively uncommon primary motility disorder characterized by aperistalsis in the body of the esophagus, an elevated lower esophageal sphincter pressure, and absent or incomplete lower esophageal sphincter relaxation in response to swallowing. (See, e.g., Thompson and Shaffer, *First Principles of Gastroenterology*, supra). The absence of lower esophageal sphincter relaxation produces progressive proximal dilation of the esophagus and elevated resting intraesophageal pressure. (See, e.g., Thompson and Shaffer, *First Principles of Gastroenterology*, supra). The esophagus is dilated on x-ray examination and the distal esophagus narrows in a beak-like fashion. Achalasia is caused by degeneration of inhibitory neurons within the esophageal and lower esophageal sphincter myenteric plexus, as well as nerve damage in the vagal nerve trunks and the dorsal motor nuclei. (See, e.g., Thompson and Shaffer, *First Principles of Gastroenterology*, supra). The parasite *Trypanosoma cruzi* can cause achalasia by destroying myenteric neurons (Chagas' disease). (See, e.g., Thompson and Shaffer, *First Principles of Gastroenterology*, supra). Neoplastic disease can also cause "secondary" achalasia by interfering with esophageal and lower esophageal sphincter nerve function. (See, e.g., Thompson and Shaffer, *First Principles of Gastroenterology*, supra).

Patients with achalasia often present with dysphagia, and some patients may complain of chest pain and/or regurgitation of esophageal contents. (See, e.g., Thompson and Shaffer, *First Principles of Gastroenterology*, supra). Heartburn may also occur, although it is caused by lactic acid formed by fermentation of stagnant esophageal contents and not from gastroesophageal reflux. (See, e.g., Thompson and Shaffer, *First Principles of Gastroenterology*, supra). Current treatment options include the use of nitrates and some calcium channel blockers. (See, e.g., Thompson and Shaffer, *First Principles of Gastroenterology*, supra). Pneumatic balloon dilation of the lower esophageal sphincter may also be used, which consists of passing a balloon across the sphincter and inflating it rapidly so that the sphincter is forcefully dilated. (See, e.g., Thompson and Shaffer, *First Principles of Gastroenterology*, supra). For patients who do not respond to pneumatic dilation, a Heller myotomy may be used in which a longitudinal incision is made through the muscle of the lower esophageal sphincter. (See, e.g., Thompson and Shaffer, *First Principles of Gastroenterology*, supra). Some recent studies have also found that injection of botulinum toxin into the muscle of the lower esophageal sphincter can alleviate dysphagia in approximately two-thirds of patients with achalasia, but the average duration of relief is only one year. (See, e.g., Thompson and Shaffer, *First Principles of Gastroenterology*, supra). Therefore, the compounds of the present invention meet an existing need for new treatments for achalasia.

Peripheral vs. Central Effects

The mammalian nervous system comprises a central nervous system (CNS, comprising the brain and spinal cord) and a peripheral nervous system (PNS, comprising sympathetic, parasympathetic, sensory, motor, and enteric neurons outside of the brain and spinal cord). Where an active agent according to the present invention is intended to act centrally (i.e., exert its effects via action on neurons in the CNS), the active agent must either be administered directly into the CNS or be capable of bypassing or crossing the blood-brain barrier. The blood-brain barrier is a capillary wall structure that effectively screens out all but selected categories of substances present in the blood, preventing their passage into the CNS. The unique morphologic characteristics of the brain capillaries that make up the blood-brain barrier are: 1) epithelial-like high resistance tight junctions which literally cement all endothelia of brain capillaries together within the blood-brain barrier regions of the CNS; and 2) scanty pinocytosis or transendothelial channels, which are abundant in endothelia of peripheral organs. Due to the unique characteristics of the blood-brain barrier, many hydrophilic drugs and peptides that readily gain access to other tissues in the body are barred from entry into the brain or their rates of entry are very low.

The blood-brain barrier can be bypassed effectively by direct infusion of the active agent into the brain, or by intranasal administration or inhalation of formulations suitable for uptake and retrograde transport of the active agent by olfactory neurons. The most common procedure for administration directly into the CNS is the implantation of a catheter into the ventricular system or intrathecal space. Alternatively, the active agent can be modified to enhance its transport across the blood-brain barrier. This generally requires some solubility of the drug in lipids, or other appropriate modification known to one of skill in the art. For example, the active agent may be truncated, derivatized, latentiated (converted from a hydrophilic drug into a lipid-soluble drug), conjugated to a lipophilic moiety or to a substance that is actively transported across the blood-brain barrier, or modified using standard means known to those skilled in the art. See, for example, Pardridge, Endocrine Reviews 7: 314–330 (1986) and U.S. Pat. No. 4,801,575.

Where an active agent according to the present invention is intended to act exclusively peripherally (i.e., exert its effects via action either on neurons in the PNS or directly on target tissues), it may be desirable to modify the compounds of the present invention such that they will not pass the blood-brain barrier. The principle of blood-brain barrier permeability can therefore be used to design active agents with selective potency for peripheral targets. Generally, a lipid-insoluble drug will not cross the blood-brain barrier, and will not produce effects on the CNS. A basic drug that acts on the nervous system may be altered to produce a selective peripheral effect by quaternization of the drug, which decreases its lipid solubility and makes it virtually unavailable for transfer to the CNS. For example, the charged antimuscarinic drug methscopalamine bromide has peripheral effects while the uncharged antimuscarinic drug scopolamine acts centrally. One of skill in the art can select and modify active agents of the present invention using well-known standard chemical synthetic techniques to add a lipid impermeable functional group such a quaternary amine, sulfate, carboxylate, phosphate, or sulfonium to prevent transport across the blood-brain barrier. Such modifications are by no means the only way in which active agents of the present invention may be modified to be impermeable to the blood-brain barrier; other well known pharmaceutical techniques exist and would be considered to fall within the scope of the present invention.

Agents

Compounds useful in the present invention include any active agent as defined elsewhere herein. Such active agents include, for example, sodium channel modulators, including TTX-R sodium channel modulators and/or activity dependent sodium channel modulators. TTX-R sodium channel modulators for use in the present invention include but are not limited to compounds that modulate or interact with Nav1.8 and/or Nav1.9 channels.

Voltage gated sodium channels, also known as voltage dependent sodium channels, are membrane-spanning proteins which permit controlled sodium influx from an extracellular environment into the interior of a cell. Opening and closing (gating) of voltage gated sodium channels is controlled by a voltage sensitive region of the protein containing charged amino acids that move within an electric field. The movement of these charged groups leads to conformational changes in the structure of the channel resulting in conducting (open/activated) or non-conducting (closed/inactivated) states.

Voltage gated sodium channels are present in a variety of tissues and are implicated in several vital processes in animals. Changes in sodium influx into cells mediated through voltage dependent sodium channels have been implicated in various human disorders such as epilepsy, pain, anaesthesia, neuroprotection, arrhythmia, and migraine (See, e.g., U.S. Pat. No. 6,479,498).

At least nine distinct voltage gated sodium channels have been identified in mammals (A. I. Goldin (2001) *Annu. Rev. Physiol.*, 63: 871–94). Although most voltage gated sodium channels are tetrodotoxin-sensitive (TTX-S), tetrodotoxin-resistant (TTX-R) sodium channels have also been identified. Two of these TTX-R sodium channels, $Na_v1.8$ and $Na_v1.9$, are thought to be specific to sensory neurons, including neurons of the dorsal root ganglia (DRG). Antisense and knockout technologies have suggested a possible role for TTX-R sodium channels in painful bladder disorders (See e.g., N. Yoshimura et al. (2001) *J. Neurosci.* 21: 8690–6; N. Yoshimura et al. (2001) *Urology* 57: 116–7).

Compounds have been described that modulate sodium channels in an activity-dependent manner, meaning that these compounds preferentially modulate the activity of a sodium channel that has been activated or opened, and exhibit their effect either by modifying the activity of the open channel, or by modifying the activity of the inactivated state of the channel as described in Hille B. (1992) *Ionic Channels in Excitable Membranes.* 2nd ed. Sinauer Associates, Sunderland, Mass., pp. 390–422. Generally, this activity-dependent sodium channel modulation will alter the release of neurotransmitters under conditions that would normally cause sustained depolarization of neurons and/or repetitive firing of action potentials. Compounds that modulate sodium channels in an activity-dependent manner may include agents that interact with the sodium channel pore itself, as well as those that act as allosteric modulators of the channel by interacting with to a site on the channel complex.

Some sodium channel modulators may selectively modulate TTX-R sodium channels, while others may act non-selectively on sodium channels. Likewise, some activity dependent sodium channel modulators may selectively modulate TTX-R sodium channels, while others may act non-selectively on sodium channels, or on non-TTX-R sodium channels.

Agents useful in the practice of the invention include, but are not limited to propionamides such as Ralfinamide (NW-1029) (as disclosed in U.S. Pat. Nos. 5,236,957 and 5,391, 577), which is also known as (+)-2(S)-[4-(2-Fluorobenzyloxy)benzylamino]propionamide and is represented by the following structure:

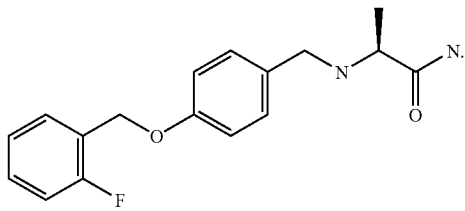

It is understood that the present invention also encompasses any salts, enantiomers, analogs, esters, amides, and derivatives of Ralfinamide, including:

a. Safinamide (as disclosed in U.S. Pat. Nos. 5,236,957 and 5,391,577), which is also known as 2(S)-[4-(3-Fluorobenzyloxy)benzylamino]propionamide methanesulfonate and is represented by the following structure:

·CH$_3$SO$_3$H b. Other N-phenylalkyl substituted α-amino carboxamide derivatives in addition to Ralfinamide and Safinamide as disclosed in U.S. Pat. No. 5,236,957, including 2-(4-benzylthiobenzyl)aminopropionamide; 2-[4-(2-chlorobenzyloxy)benzyl]amino-N-methylpropionamide; and as disclosed in U.S. Pat. No. 5,391,577, including 2-(4-benzyloxybenzyl)amino-3-phenyl-N-methylpropionamide; 1-[(4-benzyloxybenzyl)amino]cyclopropane-1-carboxamide; 2-(4-benzyloxybenzyl)aminopropionamide; 2-(4-benzyloxybenzyl)amino-3-hydroxy-N-methyl-butanamide;

c. Alpha-aminoamide derivatives as disclosed in U.S. Pat. No. 6,306,903, including 2-[N-4-benzyloxybenzyl-N-methyl-amino]-propanamide;

d. Substituted 2-benzylamino-2-phenyl-acetamide compounds as disclosed in U.S. Pat. No. 6,303,819, including agents with the following structural structure:

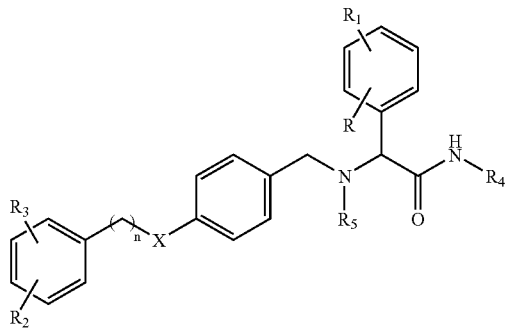

wherein:
n is zero, 1, 2, or 3;
X is —O—, —S—, —CH$_2$—, or —NH—;
each of R, R$_1$, R$_2$, and R$_3$, independently, is hydrogen, C$_1$–C$_6$ alkyl, halogen, hydroxyl, C$_1$–C$_6$ alkyl, halogen, hydroxyl, C$_1$–C$_6$ alkoxy, or trifluoromethyl;
each of R$_4$ and R$_5$, independently, is hydrogen, C$_1$–C$_6$ alkyl or C$_3$–C$_7$ cycloalkyl; or a pharmaceutically acceptable salt thereof; and e. 2-(4-Substituted)-benzylamino-2-methyl-propanamide derivatives as disclosed in U.S. Pat. No. 5,945,454, including agents with the following structural structure:

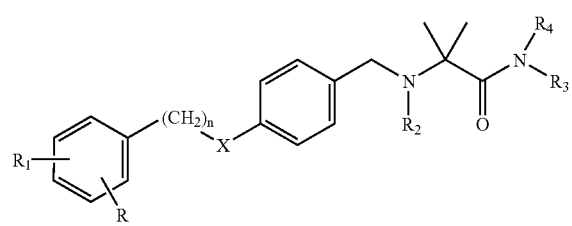

wherein:
n is zero, 1, 2, or 3;
X is —O—, —S—, —CH$_2$—, or —NH—;
each or R and R$_1$ independently is hydrogen, C$_1$–C$_6$ alkyl, halogen, hydroxyl, C$_1$–C$_4$ alkoxy, or trifluoromethyl;
each of R$_2$, R$_3$, and R$_4$ independently is hydrogen, C$_1$–C$_6$ alkyl, or C$_3$–C$_7$ cycloalkyl; or
a pharmaceutically acceptable salt thereof with a proviso that when X is —S— and R, R$_1$, R$_2$, R$_3$, and R$_4$ are hydrogen, n is not zero.

It is further understood that the present invention also encompasses any salts, enantiomers, analogs, esters, amides, and derivatives of any of the aforementioned compounds.

Additional agents useful in the practice of the invention include, but are not limited to, aryldiazines and aryltriazines such as:

a. Sipatrigine (BW-619C; as disclosed in U.S. Pat. No. 5,684,005), which is also known as 4-Amino-2-(4-methylpiperazin-1-yl)-5-(2,3,5-trichlorophenyl)pyrimidine; 2-(4-Methylpiperazin-1-yl)-5-(2,3,5-trichlorophenyl)pyrimidine-4-amine and is represented by the following structure:

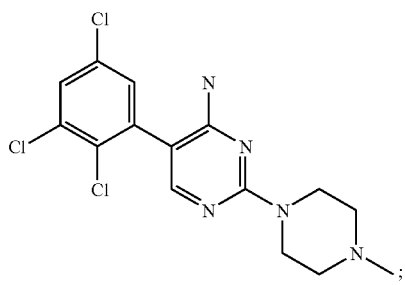

b. Lamotrigine (as disclosed in U.S. Pat. No. 4,602,017), which is also known as 6-(2,3-Dichlorophenyl)-1,2,4-triazine-3,5-diamine and is represented by the following structure:

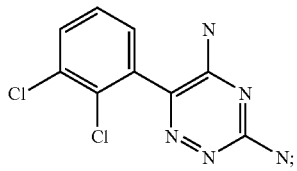

c. GW-273293 (as disclosed in U.S. Pat. No. 6,599,905), which is also known as 3-(2,3,5-Trichlorophenyl)pyrazine-2,6-diamine and is represented by the following structure:

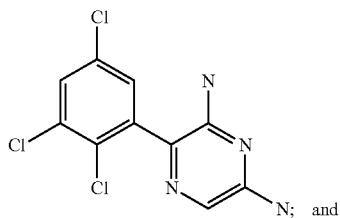

d. 4030W92 (as disclosed in U.S. Pat. No. 6,124,308), which is also known as 5-(2,3-Dichlorophenyl)-6-(fluoromethyl)pyrimidine-2,4-diamine and is represented by the following structure:

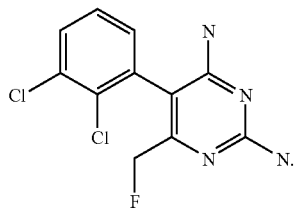

It is understood that the present invention also encompasses any salts, enantiomers, analogs, esters, amides, and derivatives of the aforementioned agents.

Additional agents useful in the practice of the invention include, but are not limited to, dibenzazepines such as:

a. Carbamazepine (as disclosed in U.S. Pat. No. 2,948,718), which is also known as 5H-Dibenz[d,f]azepine-5-carboxamide and is represented by the following structure:

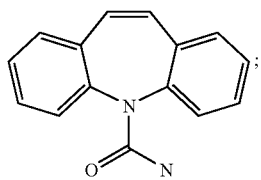

b. Oxcarbazepine (as disclosed in U.S. Pat. No. 3,642,775), which is also known as 10-Oxo-10,11-dihydro-5H-dibenz[b,f]azepine-5-carboxamide and is represented by the following structure:

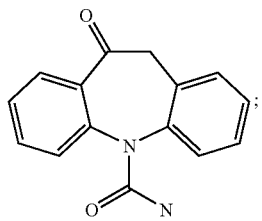

c. Licarbazepine (as disclosed in DE 2011045), which is also known as (±)-10-Hydroxy-10,11-dihydro-5H-dibenz[b,f]azepine-5-carboxamide and is represented by the following structure:

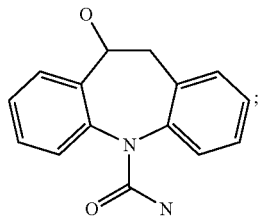

d. BIA-2-093 (as disclosed in U.S. Pat. No. 5,753,646), which is also known as Acetic acid 5-carbamoyl-10,11-dihydro-5H-dibenzo[b,f]azepin-10(S)-yl ester and is represented by the following structure:

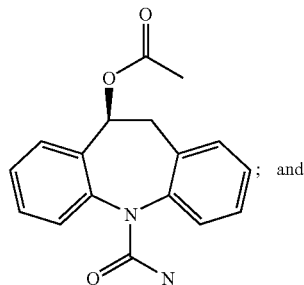

e. ADCI (as disclosed in U.S. Pat. No. 5,196,415), which is also known as (±)-5,10-Imino-10,11-dihydro-5H-dibenzo[a,d]cycloheptene-5-carboxamide and is represented by the following structure:

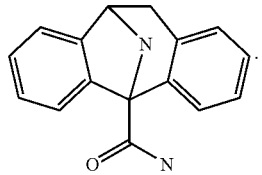

It is understood that the present invention also encompasses any salts, enantiomers, analogs, esters, amides, and derivatives of the aforementioned agents.

Additional agents useful in the practice of the invention include, but are not limited to, hydantoins such as:

a. Phenyloin sodium (as disclosed in U.S. Pat. No. 2,409,754) and OROS®-Phenyloin (as disclosed in U.S. Pat.

No. 4,260,769), which are also known as 5,5-Diphenylhydantoin sodium salt and 5,5-Diphenyl-2,4-imidazolidinedione salt, respectively, and represented by the following structure:

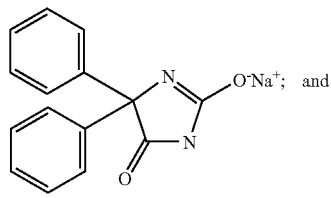

b. Fosphenyloin sodium (as disclosed in U.S. Pat. No. 4,260,769) and phosphenyloin sodium, which are also known as 3-(Hydroxymethyl)-5,5-diphenylhydantoin phosphate ester disodium salt and 5,5-Diphenyl-3-[(phosphonooxy)methyl]-2,4-imidazolidinedione disodium salt and are represented by the following structure:

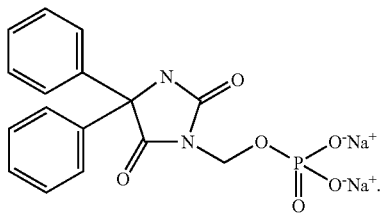

It is understood that the present invention also encompasses any salts, enantiomers, analogs, esters, amides, and derivatives of the aforementioned agents.

Additional agents useful in the practice of the invention include, but are not limited to, 3 and 4 atom spaced phenyl amines such as:

a. Pilsicainide hydrochloride (as disclosed in U.S. Pat. No. 4,564,624), which is also known as N-(2,6-Dimethylphenyl)-8-pyrrolizidineacetamide hydrochloride; N-(2,6-Dimethylphenyl)-1-azabicyclo[3.3.0]octane-5-acetamide hydrochloride and is represented by the following structure:

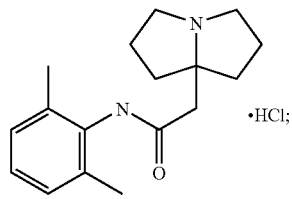

b. Tocainide (as disclosed in DE 2235745), which is also known as 2-Amino-N-(2,6-dimethylphenyl)propanamide hydrochloride and is represented by the following structure:

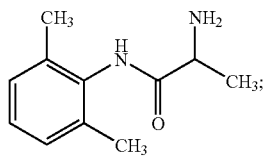

c. Flecainide (as disclosed in U.S. Pat. No. 3,900,481), which is also known as N-(2-Piperidylmethyl)-2,5-bis(2,2,2-trifluoroethoxy)benzamide monoacetate and is represented by the following structure:

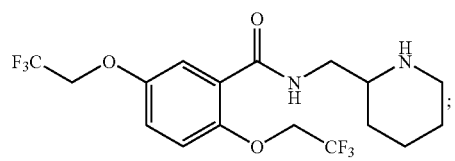

d. Mexiletine hydrochloride (as disclosed in U.S. Pat. No. 3,954,872), which is also known as 1-(2,6-Dimethylphenoxy)-2-propanamine hydrochloride and is represented by the following structure:

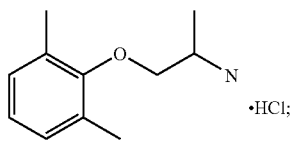

e. Ropivacaine hydrochloride (as disclosed in PCT Publication No. WO 85/00599), which is also known as (−)-(S)-N-(n-Propyl)piperidine-2-carboxylic acid 2,6-xylidide hydrochloride monohydrate; (−)-(S)-N-(2,6-Dimethylphenyl)-1-propylpiperidine-2-carboxamide hydrochloride monohydrate; (−)-(S)-1-Propyl-2',6'-pipecoloxylidide hydrochloride monohydrate and is represented by the following structure:

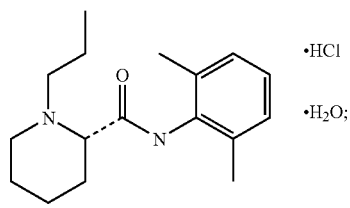

f. Lidocaine (as disclosed in U.S. Pat. No. 2,441,498), which is also known as 2-(diethylamino)-N-(2,6-dimethylphenyl)acetamide and is represented by the following structure:

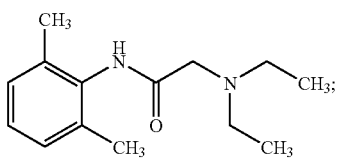

g. Mepivacaine (as disclosed in U.S. Pat. No. 2,799,679), which is also known as N-(2,6-dimethylphenyl)-1-methyl-2-piperidinecarboxamide and is represented by the following structure:

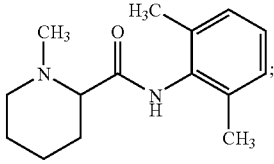

h. Bupivacaine (as disclosed in U.S. Pat. No. 2,955,111), which is also known as 1-butyl-N-(2,6-dimethylphenyl)-2-piperidinecarboxamide and is represented by the following structure:

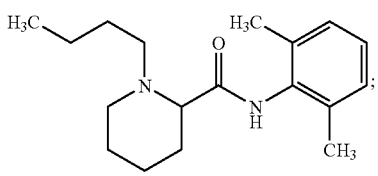

i. Prilocaine (as disclosed in U.S. Pat. No. 3,160,662), also known as N-(2-methylphenyl)-2-(propylamino)propanamide and is represented by the following structure:

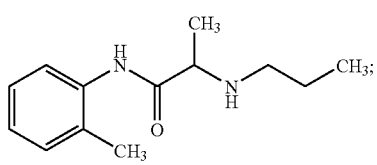

j. Etidocaine (as disclosed in U.S. Pat. No. 3,812,147), which is also known as N-(2,6-dimethylphenyl)-1-methyl-2-piperidinecarboxamide and is represented by the following structure:

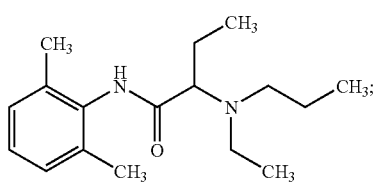

k. Tetracaine (as disclosed in U.S. Pat. No. 1,889,645), which is also known as 4-(butylamino)benzoic acid 2-(diethylamino)ethyl ester and is represented by the following structure:

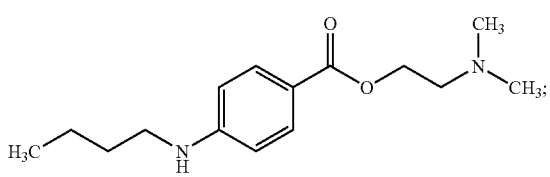

l. Dibucaine (as disclosed in U.S. Pat. No. 1,825,623), which is also known as 2-butoxy-N-[2-(diethylamino)-ethyl]-4-quinolinecarboxamide and is represented by the following structure:

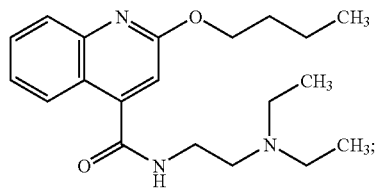

m. Soretolide, which is also known as 2,6-Dimethyl-N-(5-methylisozaxol-3-yl)benzamide and is represented by the following structure:

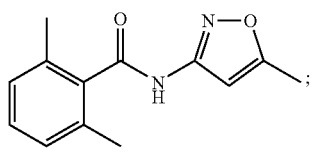

n. RS-132943 (as disclosed in U.S. Pat. No. 6,110,937), which is also known as 3(S)-(4-Bromo-2,6-dimethylphenoxymethyl)-1-methylpiperidine hydrochloride and is represented by the following structure:

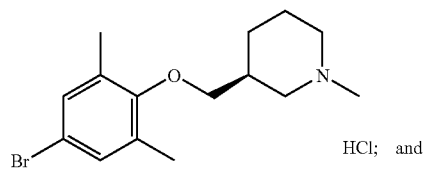

o. Tolperisone (as disclosed in HU 144997), which is also known as 2-Methyl-1-(4-methylphenyl)-3-(1-piperidinyl)propan-1-one and is represented by the following structure:

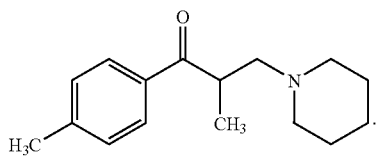

It is understood that the present invention also encompasses any salts, enantiomers, analogs, esters, amides, and derivatives of the aforementioned agents.

Additional agents useful in the practice of the invention include, but are not limited to, anticonvulsants such as:

a. Losigamone (as disclosed in U.S. Pat. No. 4,855,320), which is also known as (5R*)-5-[(alphaS*)-o-Chloro-alpha-hydroxybenzyl]-4-methoxy-2(5H)-furanone and is represented by the following structure:

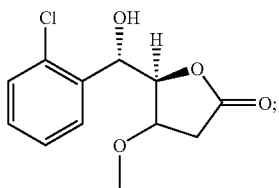

b. Zonisamide (as disclosed in U.S. Pat. No. 4,172,896), which is also known as 3-(Sulfamoylmethyl)-1,2-benzisoxazole; 1,2-Benzisoxazole-3-methanesulfonamide and is represented by the following structure:

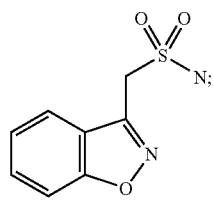

c. Topiramate (as disclosed in U.S. Pat. No. 4,513,006), which is also known as 2,3:4,5-Bis-O-(1-methylethylidene)-1-O-sulfamoyl-beta-D-fructopyranose; 2,3:4,5-Bis-O-(1-methylethylidene)-beta-D-fructopyranose sulfamate and is represented by the following structure:

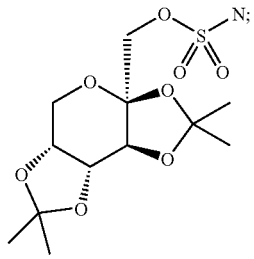

d. Rufinamide (as disclosed in U.S. Pat. No. 4,789,680), which is also known as 1-(2,6-Difluorobenzyl)-1H-1,2,3-triazole-4-carboxamide and is represented by the following structure:

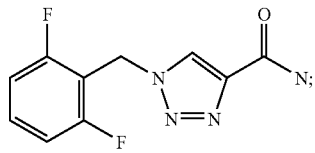

e. BW-534U87 (as disclosed in U.S. Pat. No. 5,166,209), which is also known as 4-Amino-1-(2,6-difluorobenzyl)-1H-1,2,3-triazolo[4,5-c]pyridine hydrochloride and is represented by the following structure:

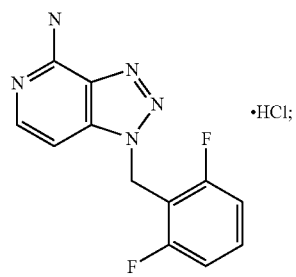

f. AWD-140–190 (as disclosed in U.S. Pat. No. 5,502,051), which is also known as 4-(4-Bromophenyl)-3-(morpholin-4-yl)pyrrole-2-carboxylic acid methyl ester and is represented by the following structure:

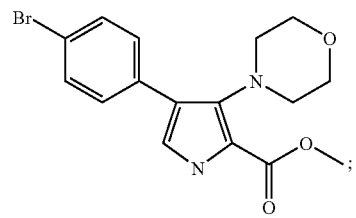

g. Harkoseride (as disclosed in U.S. Pat. No. 5,773,475), which is also known as erlosamide and 2(R)-Acetamido-N-benzyl-3-methoxypropionamide and is represented by the following structure:

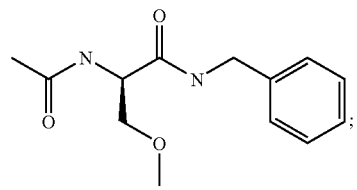

h. Memantine hydrochloride (as disclosed in U.S. Pat. No. 3,391,142) which is also known as 3,5-Dimethyl-1-adamantanamine hydrochloride and is represented by the following structure:

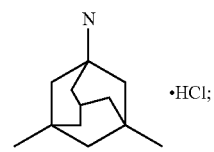

i. Felbamate (as disclosed in U.S. Pat. No. 2,884,444), which is also known as 2-Phenyl-1,3-propanediol dicarbamate and is represented by the following structure:

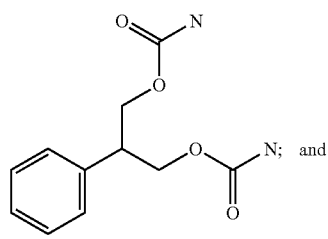

j. Valproate, which is also known as 2-Propylpentanoic acid sodium salt and is represented by the following structure:

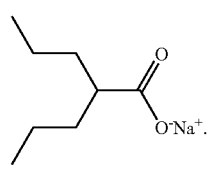

It is understood that the present invention also encompasses any salts, enantiomers, analogs, esters, amides, and derivatives of the aforementioned agents.

Additional agents useful in the practice of the invention include, but are not limited to, peptide toxins and/or insecticides such as:

a. μ-conotoxin SmIIIA from *Conus stercusmuscarum* as disclosed in West et al. (2002) *Biochemistry* 41:15388–15393;
b. Toxins as disclosed in Tan et al. (2001) *Neuropharmacology* 40:352–357;
c. Tarantula venom toxins ProTx-I and ProTx-II as disclosed in Middleton et al. (2002) *Biochemistry* 41:14734–14747;
d. Scorpion neurotoxin BmK IT2;
e. Pacific Ciguatoxin-1 (P-CTX-1);
f. Indoxacarb (as disclosed in WO 9211249), which is also known as methyl (S)-N-[7-chloro-2,3,4a,5-tetrahydro-4a-(methoxycarbonyl)indeno[1,2-e][1,3,4]oxadiazin-2-ylcarbonyl-4'-(trifluoromethoxy)carbanilate and is represented by the following structure:

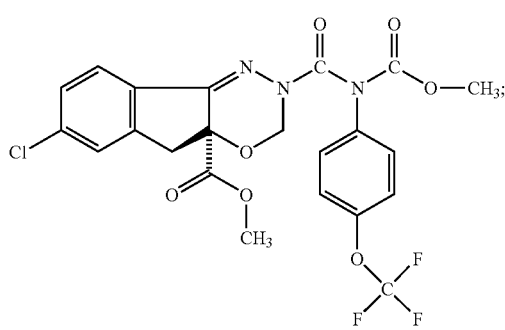

g. The DCJW metabolite of indoxacarb;
h. RH-3421 (as disclosed in Tsurubuchi et al., *Neurotoxicology* 22:443–453, 2001), which is also known as methyl 3-(4-chlorophenyl)-1-[N-(4-trifluoromethylphenyl)carbamoyl]-4-methyl-2-pyrazole-4-carboxylate and is represented by the following structure:

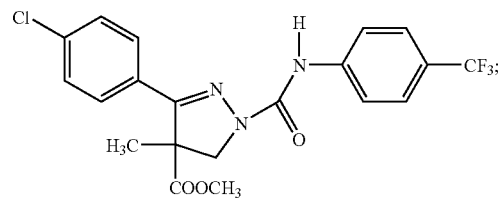

i. Deltamethrin (as disclosed in DE 2439177), which is also known as (S)-α-cyano-3-phenoxybenzyl (1R,3R)-3-(2,2-dibromovinyl)-2,2-dimethylcyclopropanecarboxylate and is represented by the following structure:

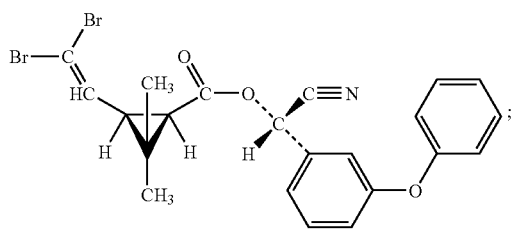

j. Tetramethrin (as disclosed in U.S. Pat. No. 3,268,398), which is also known as cyclonex-1-ene-1,2-dicarboximidomethyl (1RS,3RS; 1RS,3SR)-2,2-dimethyl-3-(2-methylprop-1-enyl)cyclopropanecarboxylate and is represented by the following structure:

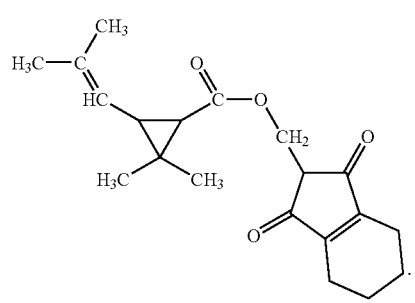

It is understood that the present invention also encompasses any salts, enantiomers, analogs, esters, amides, and derivatives of the aforementioned agents.

Additional agents useful in the practice of the invention include, but are not limited to:

a. Tetrodotoxin, which is also known as (4R,4aR,5R,7S,9S,10S,10aR, 11S,12S)-Octahydro-12-(hydroxymethyl)-2-imino-5,9:7,10a-dimethano-10aH-[1,3]dioxocino[6,5-d]pyrimidine-4,7,10,11,12-pentol and is represented by the following structure:

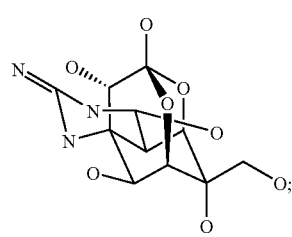

b. Ambroxol (as disclosed in U.S. Pat. No. 3,536,713), which is also known as 4-[[2-amino-3,5-dibromophenyl)methyl]amino]cyclohexanol and is represented by the following structure:

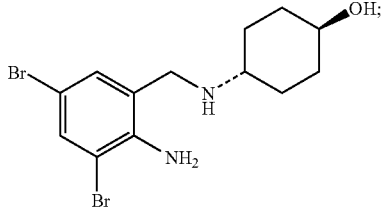

c. Enecadin hydrochloride (as disclosed in U.S. Pat. No. 6,191,149), which is also known as 4-(4-Fluorophenyl)-2-methyl-6-[5-(1 -piperidinyl)pentyloxy]pyrimidine hydrochloride and is represented by the following structure:

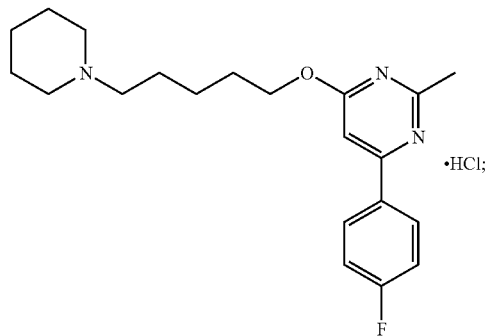

d. Fluphenazine hydrochloride (as disclosed in U.S. Pat. No. 3,058,979), which is also known as 4-[3-[2-(Trifluoromethyl)phenothiazin-10-yl]propyl]-1-piperazineethanol dihydrochloride and is represented by the following structure:

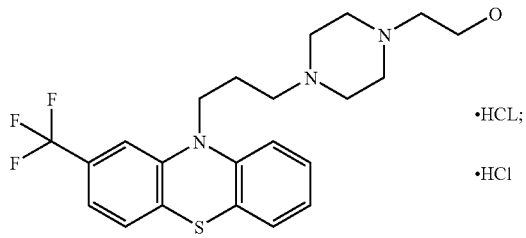

e. Trimebutine maleate (as disclosed in FR 1344455), which is also known as 3,4,5-Trimethoxybenzoic acid 2-(dimethylamino)-2-phenylbutyl ester maleate and is represented by the following structure:

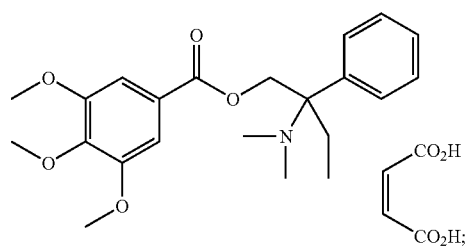

f. Riluzole (as disclosed in EP 0050551), which is also known as 2-Amino-6-(trifluoromethoxy)benzothiazole; 6-(Trifluoromethoxy)benzothiazol-2-amine and is represented by the following structure:

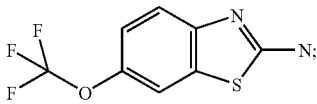

g. Silperisone hydrochloride and analogs thereof (as disclosed in U.S. Pat. No. 5,198,446), which is also known as 1-(4-Fluorophenyl)-2,2-dimethyl-3-piperidino-2-silapropane hydrochloride; 1-[(4-Fluorobenzyl)dimethylsilylmethyl]piperidine hydrochloride and is represented by the following structure:

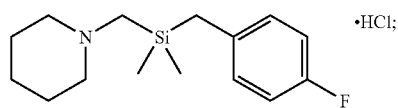

h. RSD-921 and analogs thereof (as disclosed in U.S. Pat. No. 5,506,257), which is also known as (+)-(1R,2R)-N-Methyl-N-[2-(1-pyrrolidinyl)cyclohexyl]benzo[b]thiophene-4-acetamide and is represented by the following structure:

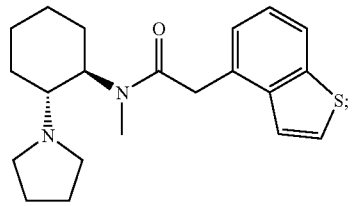

i. Crobenetine hydrochloride and analogs thereof (as disclosed in U.S. Pat. No. 6,455,538), which is also known as (2R,6S)-3-[2(S)-Benzyloxypropyl]-6,11,11-trimethyl-1,2,3,4,5,6-hexahydro-2,6-methano-3-benzazocin-10-ol hydrochloride and is represented by the following structure:

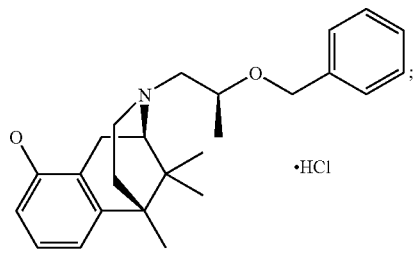

j. DL-017 and analogs thereof (as disclosed in U.S. Pat. No. 5,340,814), which is also known as 3-[4-(2-Methoxyphenyl)piperazin-1-ylmethyl]-5-(methylsulfanyl)-2,3-dihydroimidazo[1,2-c]quinazoline and is represented by the following structure:

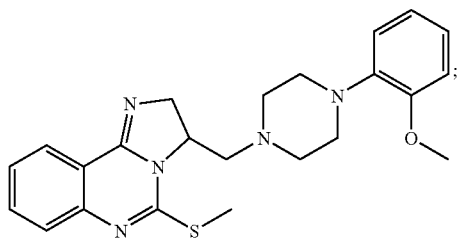

k. SUN-N8075 and analogs thereof (as disclosed in U.S. Pat. No. 6,407,099), which is also known as 1-(4-Amino-2,3,5-trimethylphenoxy)-3-[4-[4-(4-fluorobenzyl)phenyl]piperazin-1-yl]propan-2(S)-ol dimethanesulfonate and is represented by the following structure:

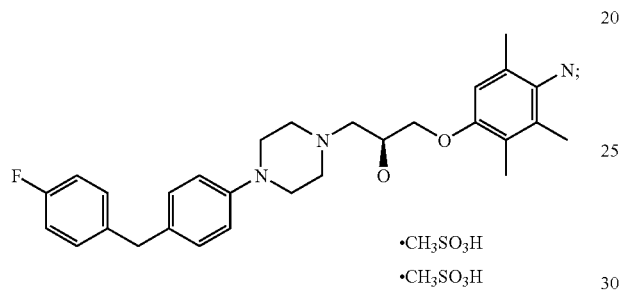

l. Amitriptyline (as disclosed in U.S. Pat. No. 3,205,264), which is also known as 3-(10,11-dihydro-5H-dibenzo[a,d]-cyclohepten-5-ylidene)-N,N-dimethyl-1-propanamine and is represented by the following structure:

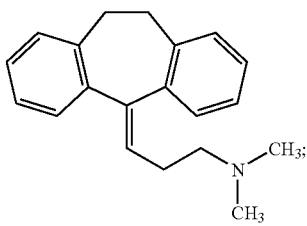

m. Compounds as disclosed in Oda et al. (2000) *Anesth. Analg.* 91:1213–1220;

n. Benzocaine, which is also known as 4-aminobenzoic acid ethyl ester, and is represented by the following structure:

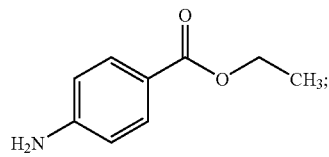

o. Compounds that inhibit the binding of Annexin II light chain or FHF1B to TTX-R sodium channels as disclosed in Liu et al., (2001) *J. Biol. Chem.* 276:18925–18933;

p. Thimerosal (as disclosed in U.S. Pat. No. 1,672,615), which is also known as ethyl[2-mercaptobenzoato(2-)-O,S]mercurate(1-) sodium and is represented by the following structure:

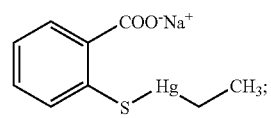

q. Vinpocetine, which is also known as (3alpha,16alpha)-Ebumamenine-14-carboxylic acid ethyl ester and represented by the following structure:

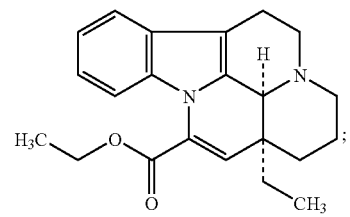

r. Vincamine, which is also known as (3α,14β,16α)-14,15-dihydro-14-hydroxyeburnamenine-14-carboxylic acid methyl ester and represented by the following structure:

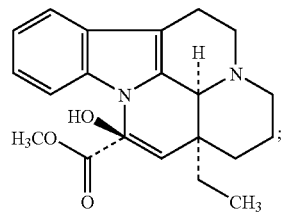

s. Quinidine, which is also known as 1(R)-(6-Methoxy-4-quinolinyl)-1-[(2R,4S,5R)-5-vinyl-1-azabicyclo[2.2.2]oct-2-yl]methanol and is represented by the following structure:

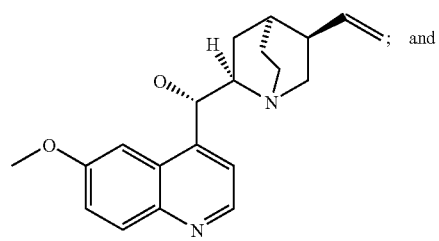

t. Co-102862 (as disclosed in U.S. Pat. No. 6,613,803), which is also known as 4-[4-fluorophenoxy]benzaldehyde semicarbazone and represented by the following structure:

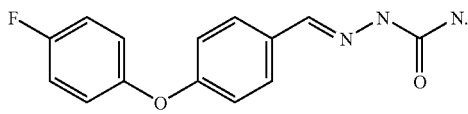

It is understood that the present invention also encompasses any salts, enantiomers, analogs, esters, amides, and derivatives of the aforementioned agents.

Other agents useful in the present invention include, but are not limited to, other compounds that interact with or modulate sodium channels, including synthetic peptides, peptidomimetics, or members of the same series or toxins from the same or related species as those compounds specifically listed above.

The identification of other agents that have affinity for TTX-R sodium channels or proteins associated with TTX-R sodium channels and would be useful in the present invention can be determined by methods that measure functional TTX-R channel activity such as sodium flux as disclosed in Stallcup, W B (1979) *J. Physiol.* 286: 525–40 or electrophysiological approaches as disclosed in Weiser and Wilson (2002) *Mol. Pharmacol.* 62: 433–438. The identification of other agents that exhibit activity-dependent modulation of sodium channels and would be useful in the present invention can be determined by methods as disclosed in Li et al., (1999) Molecular Pharmacology 55:134–141.

One or more additional active agents can be administered with a sodium channel modulator, particularly a tetrodotoxin-resistant (TTX-R) sodium channel modulator and/or activity-dependent sodium channel modulator, either simultaneously or sequentially. The additional active agent will generally, although not necessarily, be one that is effective in treating GI tract disorders except for acid peptic disorders or structural gastroesophageal disorders, and/or an agent that augments the effect of the sodium channel modulator, particularly a tetrodotoxin-resistant (TTX-R) sodium channel modulator and/or activity-dependent sodium channel modulator. Suitable secondary agents include but are not limited to, for example, antispasmodics, tricyclic antidepressants, duloxetine, venlafaxine, monoamine reuptake inhibitors (including selective serotonin reuptake inhibitors (SSRI's) and serotonin/norepinephrine reuptake inhibitors (SNRI's)), spasmolytics, anticholinergics (particularly antimuscarinics), gabapentin, pregabalin, substituted aminomethyl-phenyl-cyclohexane derivatives including tramadol, 5-$HT_3$ antagonists, 5-$HT_4$ antagonists, β3 adrenergic agonists, neurokinin receptor antagonists, bradykinin receptor antagonists, nitric oxide donors and/or any agent that does not inhibit the action of the sodium channel modulator, particularly a tetrodotoxin-resistant (TTX-R) sodium channel modulator and/or activity-dependent sodium channel modulator.

Antispasmodic drugs that may be employed as additional active agents may include, for example, Alibendol, Ambucetamide, Aminopromazine, Apoatropine, Bevonium Methyl Sulfate, Bietamiverine, Butaverine, Butropium Bromide, N-Butylscopolammonium Bromide, Caroverine, Cimetropium Bromide, Cinnamedrine, Clebopride, Coniine Hydrobromide, Coniine Hydrochloride, Cyclonium Iodide, Difemerine, Diisopromine, Dioxaphetyl Butyrate, Diponium Bromide, Drofenine, Emepronium Bromide, Ethaverine, Feclemine, Fenalamide, Fenoverine, Fenpiprane, Fenpiverinium Bromide, Fentonium Bromide, Flavoxate, Flopropione, Gluconic Acid, Guaiactamine, Hydramitrazine, Hymecromone, Leiopyrrole, Mebeverine, Moxaverine, Nafiverine, Octamylamine, Octaverine, Pentapiperide, Phenamacide Hydrochloride, Phloroglucinol, Pinaverium Bromide, Piperilate, PipoxolanHydrochloride, Pramiverin, Prifinium Bromide, Properidine, Propivane, Propyromazine, Prozapine, Racefemine, Rociverine, Spasmolytol, Stilonium Iodide, Sultroponium, Tiemonium Iodide, Tiquizium Bromide, Tiropramide, Trepibutone, Tricromyl, Trifolium, Trimebutine, N,N-1Trimethyl-3,3-diphenyl-propylamine, Tropenzile, Trospium Chloride, and Xenytropium Bromide.

Spasmolytics are compounds that relieve, prevent, or lessen muscle spasms, especially of smooth muscle. In general, spasmolytics have been implicated as having efficacy in the treatment of visceral disorders (See e.g., Takeda et al. (2000) *J. Pharmacol. Exp. Ther.* 293: 939–45).

Any spasmolytic agent is also useful as an additional active agent in the present invention. Compounds that have been identified as spasmolytic agents and are useful as an additional active agent in the present invention include, but are not limited to:

a. α-α-diphenylacetic acid-4-(N-methyl-piperidyl) esters as disclosed in U.S. Pat. No. 5,897,875;
b. Human and porcine spasmolytic polypeptides in glycosylated form and variants thereof as disclosed in U.S. Pat. No. 5,783,416;
c. Dioxazocine derivatives as disclosed in U.S. Pat. No. 4,965,259;
d. Quaternary 6,11-dihydro-dibenzo-[b,e]-thiepine-11-N-alkylnorscopine ethers as disclosed in U.S. Pat. No. 4,608,377;
e. Quaternary salts of dibenzo[1,4]diazepinones, pyrido-[1,4]benzodiazepinones, pyrido[1,5]benzodiazepinones as disclosed in U.S. Pat. No. 4,594,190;
f. Endo-8,8-dialkyl-8-azoniabicyclo (3.2.1) octane-6,7-exo-epoxy-3-alkyl-carboxylate salts as disclosed in U.S. Pat. No. 4,558,054;
g. Pancreatic spasmolytic polypeptides as disclosed in U.S. Pat. No. 4,370,317;
h. Triazinones as disclosed in U.S. Pat. No. 4,203,983;
i. 2-(4-Biphenylyl)-N-(2-diethylamino alkyl)propionamide as disclosed in U.S. Pat. No. 4,185,124;
j. piperazino-pyrimidines as disclosed in U.S. Pat. No. 4,166,852;
k. Aralkylamino carboxylic acids as disclosed in U.S. Pat. No. 4,163,060;
l. Aralkylamino sulfones as disclosed in U.S. Pat. No. 4,034,103;
m. Smooth muscle spasmolytic agents as disclosed in U.S. Pat. No. 6,207,852; and
n. papaverine.

The identification of further compounds that have spasmolytic activity and would therefore be useful as an additional active agent in the present invention can be determined by performing bladder strip contractility studies as described in U.S. Pat. No. 6,207,852; Noronha-Blob et al. (1991) *J. Pharmacol. Exp. Ther.* 256: 562–567; and/or Kachur et al. (1988) *J. Pharmacol. Exp. Ther.* 247: 867–872.

Acetylcholine is a chemical neurotransmitter in the nervous systems of all animals. "Cholinergic neurotransmission" refers to neurotransmission that involves acetylcholine, and has been implicated in the control of functions as diverse as locomotion, digestion, cardiac rate, "fight or flight" responses, and learning and memory (Salvaterra (February 2000) Acetylcholine. In *Encyclopedia of Life Sciences*. London: Nature Publishing Group, http:/www.els.net). Receptors for acetylcholine are classified into two general categories based on the plant alkaloids that preferentially bind to them: 1) nicotinic (nicotine binding); or 2) antimuscarinic (muscarine binding) (See, e.g., Salvaterra, Acetylcholine, supra).

The two general categories of acetylcholine receptors may be further divided into subclasses based upon differences in their pharmacological and electrophysiological properties. Nicotinic receptors are ligand gated ion channels composed of a variety of subunits that are used to identify the following subclasses: 1) muscle nicotinic acetylcholine receptors; 2) neuronal nicotinic acetylcholine receptors that do not bind the snake venom α-bungarotoxin; and 3) neuronal nicotinic acetylcholine receptors that do bind the snake venom α-bungarotoxin (Dani et al. (July 1999) Nicotinic Acetylcholine Receptors in Neurons. In *Encyclopedia of Life Sciences*. London: Nature Publishing Group, http:/www.els.net; Lindstrom (October 2001) Nicotinic Acetylcholine Receptors. In *Encyclopedia of Life Sciences*. London: Nature Publishing Group, http:/www.els.net). By contrast, muscarinic receptors may be divided into five subclasses, labeled $M_1$–$M_5$, and preferentially couple with specific G-proteins ($M_1$, $M_3$, and $M_5$ with $G_q$; $M_2$ and $M_4$ with $G_i$/$G_o$) (Nathanson (July 1999) Muscarinic Acetylcholine Receptors. In *Encyclopedia of Life Sciences*. London: Nature Publishing Group, http:/www.els.net). In general, muscarinic receptors have been implicated in smooth muscle function (See, e.g., Appell (2002) *Cleve. Clin. J. Med.* 69: 761–9; Diouf et al. (2002) *Bioorg. Med. Chem. Lett.* 12: 2535–9; Crandall (2001) *J. Womens Health Gend. Based Med.* 10: 735–43; Chapple (2000) *Urology* 55: 33–46).

Any anticholinergic agent, specifically, any antimuscarinic agent, is useful as an additional active agent in the present invention. Compounds that have been identified as antimuscarinic agents and are useful as an additional active agent in the present invention include, but are not limited to:

a. Darifenacin (Daryon®);
  b. YM-905 (solifenacin succinate);
  c. Oxybutynin (Ditropan®);
  d. S-Oxybutynin;
  e. N-desethyl-oxybutynin;
  f. Tolterodine (Detrol®);
  g. Trospium (Uraplex®, Spasmex®);
  h. Propiverine (Detrunorm®);
  i. Propantheline bromide (Pro-Banthine®);
  j. Hyoscyamine sulfate (Levsin®, Cystospaz®);
  k. Dicyclomine hydrochloride (Bentyl®);
  l. Flavoxate hydrochloride (Urispas®);
  m. d,l (racemic) 4-diethylamino-2-butynyl phenylcyclohexylglycolate;
  n. (R)-N,N-diisopropyl-3-(2-hydroxy-5-methylphenyl)-3-phenylpropanamine L-hydrogen tartrate;
  o. (+)-(1S,3'R)-quinuclidin-3'-yl 1-phenyl-1,2,3,4-tetrahydroisoquinoline-2-carboxylate monosuccinate;
  p. alpha(+)-4-(Dimethylamino)-3-methyl-1,2-diphenyl-2-butanol proprionate;
  q. 1-methyl-4-piperidyl diphenylpropoxyacetate;
  r. 3"-hydroxyspiro[1"H,5"H-nortropane-8,1'-pyrrolidinium benzilate;
  s. 4 amino-piperidine containing compounds as disclosed in Diouf et al. (2002) *Bioorg. Med. Chem. Lett.* 12: 2535–9;
  t. pirenzipine;
  u. methoctramine;
  v. 4-diphenylacetoxy-N-methyl piperidine methiodide;
  w. tropicamide;
  x. (2R)-N-[1-(6-aminopyridin-2-ylmethyl)piperidin-4-yl]-2-[(1R)-3,3-difluorocyclopentyl]-2-hydroxy-2-phenylacetamide;
  y. PNU-200577 ((R)-N,N-diisopropyl-3-(2-hydroxy-5-hydroxymethylphenyl)-3-phenylpropanamine); and
  z. NS-21.

The identification of further compounds that have antimuscarinic activity and would therefore be useful as an additional active agent in the present invention can be determined by performing muscarinic receptor binding specificity studies as described by Nilvebrant (2002) *Pharmacol. Toxicol.* 90: 260–7 or cystometry studies as described by Modiri et al. (2002) *Urology* 59: 963–8.

Adrenergic receptors are cell-surface receptors for two major catecholamine hormones and neurotransmitters: noradrenaline and adrenaline. (Malbon et al. (February 2000) Adrenergic Receptors. In *Encyclopedia of Life Sciences*. London: Nature Publishing Group, http:/www.els.net). Adrenergic receptors have been implicated in critical physiological processes, including blood pressure control, myocardial and smooth muscle contractility, pulmonary function, metabolism, and central nervous system activity (See, e.g., Malbon et al., Adrenergic Receptors, supra). Two classes of adrenergic receptors have been identified, α and β, that may be further subdivided into three major families (α1, α2, and β3), each with at least three subtypes (α1A, B, and, D; α2A, B, and C; and β1, β2, and β3) based upon their binding characteristics to different agonists and molecular cloning techniques. (See, e.g., Malbon et al., Adrenergic Receptors, supra). It has been shown that β3 adrenergic receptors are expressed in the detrusor muscle, and that the detrusor muscle relaxes with a β3-agonist (Takeda, M. et al. (1999) *J. Pharmacol. Exp. Ther.* 288: 1367–1373), and in general, β3 adrenergic receptors have been implicated in bladder function (See, e.g., Takeda et al. (2002) *Neurol. Urodyn.* 21: 558–65; Takeda et al. (2000) *J. Pharmacol. Exp. Ther.* 293: 939–45.

Other agents useful in the present invention include any β3 adrenergic agonist agent. Compounds that have been identified as β3 adrenergic agonist agents and are useful in the present invention include, but are not limited to:

a. TT-138 and phenylethanolamine compounds as disclosed in U.S. Pat. No. 6,069,176, PCT Publication No. WO 97/15549 and available from Mitsubishi Pharma Corp.;
  b. FR-149174 and propanolamine derivatives as disclosed in U.S. Pat. Nos. 6,495,546 and 6,391,915 and available from Fujisawa Pharmaceutical Co.;
  c. KUC-7483, available from Kissei Pharmaceutical Co.,
  d. 4'-hydroxynorephedrine derivatives such as 2–2-chloro-4-(2-(((1S,2R)-2-hydroxy-2-(4-hydroxyphenyl)-1-methylethylamino)ethyl)phenoxy acetic acid as disclosed in Tanaka et al. (2003) *J. Med. Chem.* 46: 105–12;
  e. 2-amino-1-phenylethanol compounds, such as BRL35135 ((R*R*)-(.+−.)-[4-[2-[2-(3-chlorophenyl)-2-ydroxyethylamino]propyl]phenoxy]acetic acid methyl ester hydrobromide salt as disclosed in Japanese Patent Publication No. 26744 of 1988 and European Patent Publication No. 23385), and SR58611A ((RS)—N-(7-ethoxycarbonylmethoxy-1,2,3,4-tetrahydronaphth-2-yl)-2-(3-chlorophenyl)-2-hydroxyethanamine hydrochloride as disclosed in Japanese Laid-open Patent Publication No. 66152 of 1989 and European Laid-open Patent Publication No. 255415);

f. GS 332 (Sodium (2R)-[3-[3-[2-(3 Chlorophenyl)-2-hydroxyethylamino]cyclohexyl]phenoxy]acetate) as disclosed in Iizuka et al. (1998) *J. Smooth Muscle Res.* 34: 139–49;

g. BRL-37,344 (4-[-[(2-hydroxy-(3-chlorophenyl) ethyl) amino]propyl]phenoxyacetate) as disclosed in Tsujii et al. (1998) *Physiol. Behav.* 63: 723–8 and available from Glaxosmithkline;

h. BRL-26830A as disclosed in Takahashi et al. (1992) *Jpn Circ. J.* 56: 936–42 and available from Glaxosmithkline;

i. CGP 12177 (4-[3-t-butylamino-2-hydroxypropoxy]benzimidazol-2-one) (a β1/β2 adrenergic antagonist reported to act as an agonist for the β3 adrenergic receptor) as described in Tavernier et al. (1992) *J. Pharmacol. Exp. Ther.* 263: 1083–90 and available from Ciba-Geigy;

j. CL 316243 (R,R-5-[2-[[2-(3-chlorophenyl)-2-hydroxyethyl]amino]propyl]-1,3-benzodioxole-2,2-dicarboxylate) as disclosed in Berlan et al. (1994) *J. Pharmacol. Exp. Ther.* 268: 1444–51;

k. Compounds having β3 adrenergic agonist activity as disclosed in U.S. Patent Application 20030018061;

l. ICI 215,001 HCl ((S)-4-[2-Hydroxy-3-phenoxypropylaminoethoxy]phenoxyacetic acid hydrochloride) as disclosed in Howe (1993) *Drugs Future* 18: 529 and available from AstraZeneca/ICI Labs;

m. ZD 7114 HCl (ICI D7114; (S)-4-[2-Hydroxy-3-phenoxypropylaminoethoxy]-N-(2 methoxyethyl)phenoxyacetamide HCl) as disclosed in Howe (1993) *Drugs Future* 18: 529 and available from AstraZeneca/ICI Labs;

n. Pindolol (1-(1H-Indol-4-yloxy)-3-[(1-methylethyl)amino]-2-propanol) as disclosed in Blin et al (1994) *Mol. Pharmacol.* 44: 1094;

o. (S)-(–)-Pindolol ((S)-1-(1H-indol-4-yloxy)-3-[(1-methylethyl)amino]-2-propanol) as disclosed in Walter et al (1984) *Naunyn-Schmied. Arch. Pharmacol.* 327: 159 and Kalkman (1989) *Eur. J. Pharmacol.* 173: 121;

p. SR 59230A HCl (1-(2-Ethylphenoxy)-3-[[(1S)-1,2,3,4-tetrahydro-1-naphthalenyl]amino]-(2S)-2-propanol hydrochloride) as disclosed in Manara et al. (1995) *Pharmacol. Comm.* 6: 253 and Manara et al. (1996) *Br. J. Pharmacol.* 117: 435 and available from Sanofi-Midy; and q. SR 58611 (N[2s]7-carb-ethoxymethoxy-1,2,3,4-tetrahydronaphth]-(2r)-2-hydroxy-2(3-chlorophenyl) ethamine hydrochloride as disclosed in Gauthier et al. (1999) *J. Pharmacol. Exp. Ther.* 290: 687–693 and available from Sanofi Research.

The identification of further compounds that have β3 adrenergic agonist activity and would therefore be useful in the present invention can be determined by performing radioligand binding assays and/or contractility studies as described by Zilberfarb et al. (1997) *J. Cell Sci.* 110: 801–807; Takeda et al. (1999) *J. Pharmacol. Exp. Ther.* 288: 1367–1373; and Gauthier et al. (1999) *J. Pharmacol. Exp. Ther.* 290: 687–693.

Tachykinins (TKs) are a family of structurally related peptides that include substance P, neurokinin A (NKA) and neurokinin B (NKB). Neurons are the major source of TKs in the periphery. An important general effect of TKs is neuronal stimulation, but other effects include endothelium-dependent vasodilation, plasma protein extravasation, mast cell recruitment and degranulation and stimulation of inflammatory cells (See Maggi, C. A. (1991) *Gen. Pharmacol.*, 22: 1–24). In general, tachykinin receptors have been implicated in bladder function (See, e.g., Kamo et al. (2000) *Eur. J. Pharmacol.* 401: 235–40 and Omhura et al. (1997) *Urol. Int.* 59: 221–5).

Substance P activates the neurokinin receptor subtype referred to as $NK_1$. Substance P is an undecapeptide that is present in sensory nerve terminals. Substance P is known to have multiple actions that produce inflammation and pain in the periphery after C-fiber activation, including vasodilation, plasma extravasation and degranulation of mast cells (Levine, J. D. et. al. (1993) *J. Neurosci.* 13: 2273).

Neurokinin A is a peptide which is colocalized in sensory neurons with substance P and which also promotes inflammation and pain. Neurokinin A activates the specific neurokinin receptor referred to as $NK_2$ (Edmonds-Alt, S., et. al. (1992) *Life Sci.* 50: PL101). In the urinary tract, TKs are powerful spasmogens acting through only the $NK_2$ receptor in the human bladder, as well as the human urethra and ureter (Maggi, C. A. (1991) *Gen. Pharmacol.*, 22: 1–24).

Other agents useful in the present invention include any neurokinin receptor antagonist agent. Suitable neurokinin receptor antagonists for use in the present invention that act on the $NK_1$ receptor include, but are not limited to: 1-imino-2-(2-methoxy-phenyl)-ethyl)-7,7-diphenyl-4-perhydroisoindolone(3aR,7aR) ("RP 67580"); 2S,3 S-cis-3-(2-methoxybenzylamino)-2-benzhydrylquinuclidine ("CP 96,345"); and (aR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthyridine-6, 13-dione)("TAK-637"). Suitable neurokinin receptor antagonists for use in the present invention that act on the $NK_2$ receptor include but are not limited to: ((S)-N-methyl-N-4-(4-acetylamino-4-phenylpiperidino)-2-(3,4-dichlorophenyl)butylbenzamide ("SR 48968"); Met-Asp-Trp-Phe-Dap-Leu ("MEN 10,627"); and cyc(Gln-Trp-Phe-Gly-Leu-Met) ("L 659,877"). The identification of further compounds that have neurokinin receptor antagonist activity and would therefore be useful in the present invention can be determined by performing binding assay studies as described in Hopkins et al. (11991) *Biochem. Biophys. Res. Comm.* 180: 1110–1117; and Aharony et al. (1994) *Mol. Pharmacol.* 45: 9–19.

Bradykinin receptors generally are divided into $bradykinin_1$ ($B_1$) and $bradykinin_2$ ($B_2$) subtypes. Studies have shown that acute peripheral pain and inflammation produced by bradykinin are mediated by the $B_2$ subtype whereas bradykinin-induced pain in the setting of chronic inflammation is mediated via the $B_1$ subtype (Perkins, M. N., et. al. (1993) *Pain* 53: 191–97); Dray, A., et. al. (1993) *Trends Neurosci.* 16: 99–104). In general, bradykinin receptors have been implicated in bladder function (See, e.g., Meini et al. (2000) *Eur. J. Pharmacol.* 388: 177–82 and Belichard et al. (1999) *Br. J. Pharmacol.* 128: 213–9).

Other agents useful in the present invention include any bradykinin receptor antagonist agent. Suitable bradykinin receptor antagonists for use in the present invention that act on the $B_1$ receptor include but are not limited to: des-arg$^{10}$HOE 140 (available from Hoechst Pharmaceuticals) and des-Arg$^9$bradykinin (DABK). Suitable bradykinin receptor antagonists for use in the present invention that act on the $B_2$ receptor include but are not limited to: D-Phe$^7$-BK; D-Arg-(Hyp$^3$-Thi$^{5,8}$-D-Phe$^7$)-BK ("NPC 349"); D-Arg-(Hyp$^3$-D-Phe$^7$)-BK ("NPC 567"); D-Arg-(Hyp$^3$-Thi$^5$-D-Tic$^7$-Oic$^8$)-BK ("HOE 140"); H-DArg-Arg-Pro-Hyp-Gly-Thi-c(Dab-DTic-Oic-Arg)c(7gamma-1 Oalpha) ("MEN11270"); H-DArg-Arg-Pro-Hyp-Gly-Thi-Ser-DTic-Oic-Arg-OH("Icatibant"); (E)-3-(6-acetamido-3-pyridyl)-

N-[N-[2,4-dichloro-3-[(2-methyl-8-quinolinyl)oxymethyl]phenyl]-N-methylaminocarbonylmethyl]acrylamide ("FR173567"); and WIN 64338. These compounds are more fully described in Perkins, M. N., et. al., *Pain*, supra; Dray, A., et. al., *Trends Neurosci.*, supra; and Meini et al. (2000) *Eur. J. Pharmacol.* 388: 177–82. The identification of further compounds that have bradykinin receptor antagonist activity and would therefore be useful in the present invention can be determined by performing binding assay studies as described in Manning et al. (1986) *J. Pharmacol. Exp. Ther.* 237: 504 and U.S. Pat. No. 5,686,565.

Nitric oxide donors may be included in the present invention particularly for their anti-spasm activity. Nitric oxide (NO) plays a critical role as a molecular mediator of many physiological processes, including vasodilation and regulation of normal vascular tone. The action of NO is implicated in intrinsic local vasodilation mechanisms. NO is the smallest biologically active molecule known and is the mediator of an extraordinary range of physiological processes (Nathan (1994) *Cell* 78: 915–918; Thomas (1997) *Neurosurg. Focus* 3: Article 3). NO is also a known physiologic antagonist of endothelin-1, which is the most potent known mammalian vasoconstrictor, having at least ten times the vasoconstrictor potency of angiotensin II (Yanagisawa et al. (1988) *Nature* 332: 411–415; Kasuya et al. (1993) *J. Neurosurg.* 79: 892–898; Kobayashi et al., (1991) *Neurosurgery* 28: 673–679). The biological half-life of NO is extremely short (Morris et al. (1994) *Am. J. Physiol.* 266: E829–E839; Nathan (1994) *Cell* 78: 915–918). NO accounts entirely for the biological effects of endothelium-derived relaxing factor (EDRF) and is an extremely potent vasodilator that is believed to work through the action of cGMP-dependent protein kinases to effect vasodilation (Henry et al. (1993) *FASEB J.* 7: 1124–1134; Nathan (1992) *FASEB J.* 6: 3051–3064; Palmer et al., (1987) *Nature* 327: 524–526; Snyder et al. (1992) *Scientific American* 266: 68–77).

Within endothelial cells, an enzyme known as NO synthase (NOS) catalyzes the conversion of L-arginine to NO which acts as a diffusible second messenger and mediates responses in adjacent smooth muscle cells. NO is continuously formed and released by the vascular endothelium under basal conditions which inhibits contractions and controls basal coronary tone and is produced in the endothelium in response to various agonists (such as acetylcholine) and other endothelium dependent vasodilators. Thus, regulation of NOS activity and the resultant levels of NO are key molecular targets controlling vascular tone (Muramatsu et. al. (1994) *Coron. Artery Dis.* 5: 815–820).

Other agents useful in the present invention include any nitric oxide donor agent. Suitable nitric oxide donors for the practice of the present invention include but are not limited to:
a. Nitroglycerin;
b. Sodium nitroprusside;
c. FK 409 (NOR-3);
d. FR 144420 (NOR-4);
e. 3-morpholinosydnonimine;
f. Linsidomine chlorohydrate ("SIN-1");
g. S-nitroso-N-acetylpenicillamine ("SNAP");
h. AZD3582 (CINOD lead compound, available from NicOx S.A.);
i. NCX 4016 (available from NicOx S.A.);
j. NCX 701 (available from NicOx S.A.);
k. NCX 1022 (available from NicOx S.A.);
l. HCT 1026 (available from NicOx S.A.);
m. NCX 1015 (available from NicOx S.A.);
n. NCX 950 (available from NicOx S.A.);
o. NCX 1000 (available from NicOx S.A.);
p. NCX 1020 (available from NicOx S.A.);
q. AZD 4717 (available from NicOx S.A.);
r. NCX 1510/NCX 1512 (available from NicOx S.A.);
S. NCX 2216 (available from NicOx S.A.);
t. NCX 4040 (available from NicOx S.A.);
u. Nitric oxide donors as disclosed in U.S. Pat. No. 5,155,137;
v. Nitric oxide donors as disclosed in U.S. Pat. No. 5,366,997;
w. Nitric oxide donors as disclosed in U.S. Pat. No. 5,405,919;
x. Nitric oxide donors as disclosed in U.S. Pat. No. 5,650,442;
y. Nitric oxide donors as disclosed in U.S. Pat. No. 5,700,830;
z. Nitric oxide donors as disclosed in U.S. Pat. No. 5,632,981;
aa. Nitric oxide donors as disclosed in U.S. Pat. No. 6,290,981;
bb. Nitric oxide donors as disclosed in U.S. Pat. No. 5,691,423;
cc. Nitric oxide donors as disclosed in U.S. Pat. No. 5,721,365;
dd. Nitric oxide donors as disclosed in U.S. Pat. No. 5,714,511;
ee. Nitric oxide donors as disclosed in U.S. Pat. No. 6,511,911; and
ff. Nitric oxide donors as disclosed in U.S. Pat. No. 5,814,666.

The identification of further compounds that have nitric oxide donor activity and would therefore be useful in the present invention can be determined by release profile and/or induced vasospasm studies as described in U.S. Pat. Nos. 6,451,337 and 6,358,536, as well as Moon (2002) *IBJU Int.* 89: 942–9 and Fathian-Sabet et al. (2001) *J. Urol.* 165: 1724–9.

Gabapentin (Neurontin, or 1-(aminomethyl) cyclohexaneacetic acid) is an anticonvulsant drug with a high binding affinity for some calcium channel subunits, and is represented by the following structure:

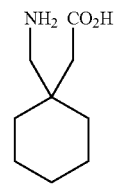

Gabapentin is one of a series of compounds of formula:

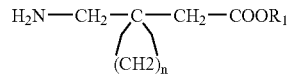

in which $R_1$ is hydrogen or a lower alkyl radical and n is 4, 5, or 6. Although gabapentin was originally developed as a GABA-mimetic compound to treat spasticity, gabapentin has no direct GABAergic action and does not block GABA uptake or metabolism. (For review, see Rose et al. (2002) *Analgesia* 57:451–462). Gabapentin has been found, however, to be an effective treatment for the prevention of partial seizures in patients who are refractory to other anticonvulsant agents (Chadwick (1991) *Gabapentin*, In Pedley T A, Meldrum B S (eds.), *Recent Advances in Epilepsy*, Churchill Livingstone, New York, pp. 211–222). Gabapentin and the related drug pregabalin interact with the □₂□ subunit of calcium channels (Gee et al. (1996) *J. Biol. Chem.* 271: 5768–5776).

In addition to its known anticonvulsant effects, gabapentin has been shown to block the tonic phase of nociception induced by formalin and carrageenan, and exerts an inhibitory effect in neuropathic pain models of mechanical hyperalgesia and mechanical/thermal allodynia (Rose et al. (2002) *Analgesia* 57: 451–462). Double-blind, placebo-controlled trials have indicated that gabapentin is an effective treatment for painful symptoms associated with diabetic peripheral neuropathy, post-herpetic neuralgia, and neuropathic pain (see, e.g., Backonja et al. (1998) *JAMA* 280: 1831–1836; Mellegers et al. (2001) *Clin. J. Pain* 17:284–95).

Pregabalin, (S)-(3-aminomethyl)-5-methylhexanoic acid or (S)-isobutyl GABA, is another GABA analog whose use as an anticonvulsant has been explored (Bryans et al. (1998) *J. Med. Chem.* 41:1838–1845). Pregabalin has been shown to possess even higher binding affinity for the □₂□ subunit of calcium channels than gabapentin (Bryans et al. (1999) *Med. Res. Rev.* 19:149–177).

The substituted aminomethyl-phenyl-cyclohexane derivatives suitable for use in the invention are represented by structural Formula I:

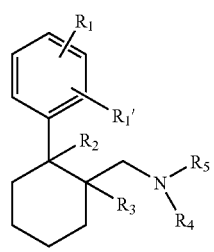

and enantiomers and mixtures thereof wherein:
$R_1$ and $R_1'$ are independently hydrogen, an aliphatic group, an aryl group, an arylalkyl group, a halogen, —CN, —OR$_6$, —SR$_6$, —NR$_6$R$_6$, —OC(O)R$_6$, —C(O)OR$_6$, —C(O)R$_6$ or —C(O)NR$_6$R$_6$;
$R_2$ is hydrogen, halogen, —OR$_7$ or —OC(O)R$_7$;
$R_3$ is hydrogen or an aliphatic group;
or $R_2$ and $R_3$ together form a double bond;
$R_4$ and $R_5$ are independently hydrogen, an aliphatic group, an aryl group, or an arylalkyl group;
$R_6$ is hydrogen, an aliphatic group, an aryl group or an arylalkyl group;
$R_7$ is hydrogen, an aliphatic group, an aryl group or an arylalkyl group;
or pharmaceutically acceptable salts, solvates or hydrates thereof.

In a particular embodiment of Formula I, $R_2$ is —OH. When $R_2$ is —OH, it is preferred that $R_1'$ is hydrogen and $R_1$ is OCH$_3$, preferably substituted at the meta position of the phenyl ring.

In a further embodiment of Formula I, $R_2$ is —OH, $R_1'$ is hydrogen and $R_1$ is —OR$_6$, substituted at the meta position of the phenyl ring and R$_6$ is an aliphatic group, for example, and alkyl group. In a particular embodiment, wherein $R_2$ is —OH, $R_1'$ is hydrogen and $R_1$ is —OR$_6$, substituted at the meta position of the phenyl ring and $R_6$ is an alkyl group, $R_3$, $R_4$ and $R_5$ can be hydrogen or an alkyl group.

In one embodiment, the substituted aminomethyl-phenyl-cyclohexane derivative suitable for use in the invention is represented by structural Formula II:

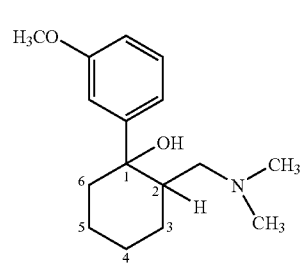

and enantiomers and mixtures thereof or pharmaceutically acceptable salts, solvates or hydrates thereof.

In a particular embodiment, the compound of Formula II is a mixture of the (+)cis and (−)cis enantiomers, wherein the C-1 and C-2 carbons of the cyclohexyl ring are (1R,2R) and (1S,2S), respectively, and the substituents on C-1 and C-2 are in the cis orientation.

In a specific embodiment, the mixture of the (+)cis and (−)cis enantiomers is a racemic mixture. That is, the compound of Formula II is a 50:50 mixture of (+)cis and (−)cis enantiomers as shown below:

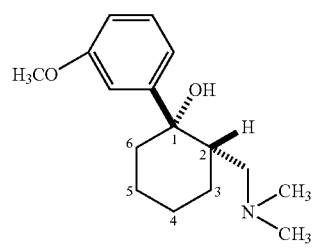

(−)cis (1S, 2S)

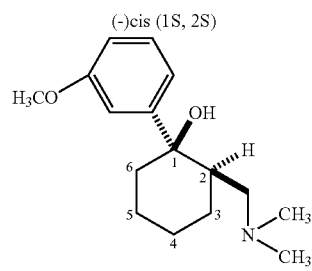

(+)cis (1R, 2R)

In other words, the compound of Formula II is the 50:50 mixture of (+/−)cis-2-[(dimethylamino)methyl]-1-(3-methoxyphenyl) cyclohexanol, commonly referred to as tramadol. The compound can be in the form of a pharmaceutically acceptable salt. Typically, tramadol is administered in the form of the hydrochloride salt. The tramadol hydrochloride is also known, for example, by the tradename ULTRAM®.

Tramadol in the form of the hydrochloride salt, is widely used as an analgesic. Tramadol is a centrally acting analgesic with a low affinity for opioid receptors. In contrast to other opioids, the analgesic action of tramadol is only partially inhibited by the opioid antagonist naloxone, which suggests the existence of an additional non-opioid mechanism of action. It has been found that monoaminergic activity, wherein noradrenaline and serotonin (5-HT) reuptake are inhibited, contributes significantly to the analgesic action of tramadol by blocking nociceptive impulses at the spinal level.

In a further embodiment, the administered compound is the (+)cis enantiomer of tramadol, set forth above.

In another embodiment, the substituted aminomethyl-phenyl-cyclohexane derivative is represented by the following structural Formula III in which the nitrogen of the aminomethyl group is in the form of the N-oxide:

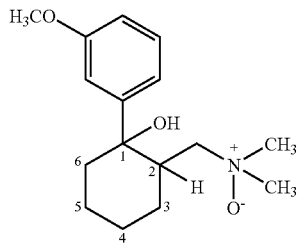

III and enantiomers and mixtures thereof or pharmaceutically acceptable salts, solvates and hydrates thereof.

In a particular embodiment, the compound of Formula III is a mixture of the (+)cis and (−)cis enantiomers, wherein the C-1 and C-2 carbons of the cyclohexyl ring are (1R,2R) and (1S,2S), respectively, and the substituents on C-1 and C-2 are in the cis orientation.

In a specific embodiment, the mixture of the (+)cis and (−)cis enantiomers is a racemic mixture. That is, the compound of Formula III is a 50:50 mixture of (+)cis and (−)cis enantiomers as shown below:

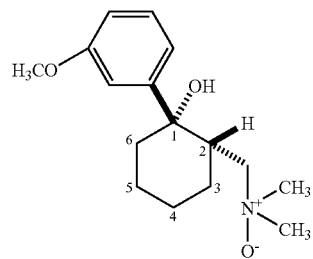

(−)cis (1S, 2S)

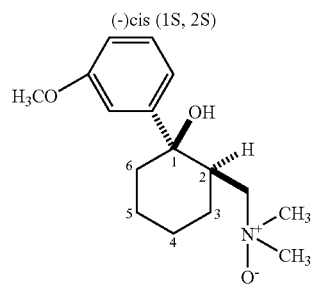

(+)cis (1R, 2R)

In other words, the compound of Formula III is the 50:50 mixture of the N-oxide of (+/−)cis-2-[(dimethylamino)methyl]-1-(3-methoxyphenyl) cyclohexanol.

In a further embodiment, the N-oxide is predominantly the (+)cis enantiomer, as set forth above.

In one embodiment, the substituted aminomethyl-phenyl-cyclohexane derivative suitable for use in the invention is represented by structural Formula IV:

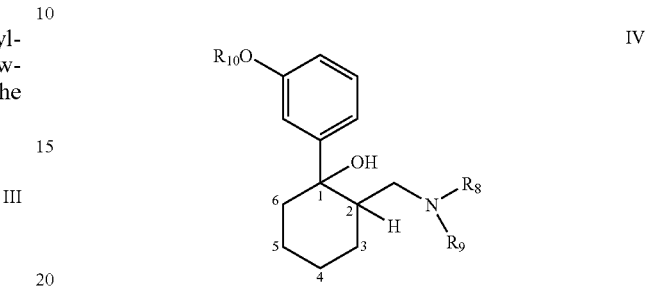

IV and enantiomers and mixtures thereof wherein:
$R_8$, $R_9$ and $R_{10}$ are independently hydrogen or an alkyl group;
or pharmaceutically acceptable salts, solvates or hydrates thereof.

In a particular embodiment, the compound of Formula IV is a mixture of the (+)cis and (−)cis enantiomers, wherein the C-1 and C-2 carbons of the cyclohexyl ring are (1R,2R) and (1S,2S), respectively, and the substituents on C-1 and C-2 are in the cis orientation.

In a specific embodiment, the mixture of the (+)cis and (−)cis enantiomers is a racemic mixture. That is, the compound of Formula IV is a 50:50 mixture of (+)cis and (−)cis enantiomers as shown below:

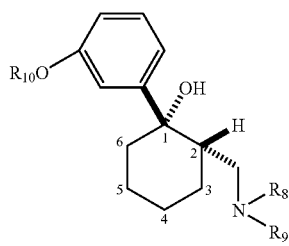

(−)cis (1S, 2S)

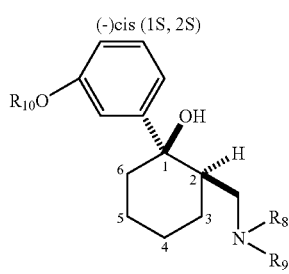

(+)cis (1R, 2R)

In a further embodiment, the compounds of Formula IV are predominantly the (+)cis enantiomer, as set forth above.

In a particular embodiment $R_{10}$ is hydrogen. In a further embodiment wherein $R_{10}$ is hydrogen, $R_8$ and $R_9$ are independently hydrogen or an alkyl group, for example, a methyl group. When $R_{10}$ is hydrogen and $R_8$ and $R_9$ are methyl groups, and Formula IV is the racemic mixture of the (+)cis and (−)cis enantiomers, the compound can be referred to as O-desmethyltramadol. The specific (+) and (−) enantiomers set forth above, can be referred to as (+)O-desmethyltramadol and (−)O-desmethyltramadol.

In yet another embodiment, $R_{10}$ is hydrogen, $R_8$ is hydrogen and $R_9$ is a methyl group. When $R_{10}$ is hydrogen, $R_8$ is hydrogen and $R_9$ is a methyl group, and Formula IV is the racemic mixture of the (+)cis and (−)cis enantiomers, the compound can be referred to as O-desmethyl-N-mono-desmethyl-tramadol. The specific (+)cis and (−)cis enantiomers as set forth above can be referred to as (+)O-desmethyl-N-mono-desmethyl-tramadol and (−)O-desmethyl-N-mono-desmethyl-tramadol.

In yet another embodiment, the substituted aminomethyl-phenyl-cyclohexane derivative is represented by structural Formula V:

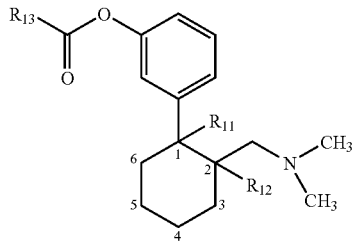

V and enantiomers and mixtures thereof wherein:
$R_1$ is —OH;
$R_{12}$ is hydrogen or $R_{11}$ and $R_{12}$ together form a double bond;
$R_{13}$ is an aryl group selected from the group consisting of:

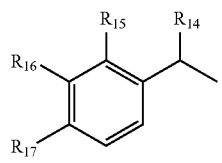

A

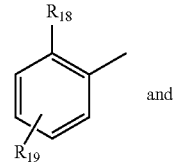

and

B

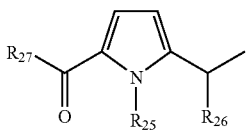

C wherein:
$R_{14}$ is hydrogen or an alkyl group;
$R_{15}$ is hydrogen, —NH$_2$, —NHR$_{20}$ or —OR$_{20}$;
$R_{16}$ is hydrogen, —COR$_{20}$, —OR$_{20}$ or halogen;
$R_{17}$ is hydrogen, an alkyl group, —O-alkenyl, a phenyl group or $R_{16}$ and $R_{17}$ are —CH═CR$_2$—, —CR$_{22}$+CH—, forming an aromatic ring;

$R_{18}$ is hydrogen, —COR$_{23}$, —OR$_{24}$ or a halogen;
$R_{19}$ is hydrogen, halogen, an alkyl group, —O-alkyl, —NO$_2$ or an aryl group;
$R_{20}$ is a phenyl group optionally substituted by one or more of the following: halogen, —NO$_2$, an alkyl group, an alkenyl group, —OH or —NH$_2$;
$R_2$, and $R_{22}$ are independently hydrogen or —O-alkyl;
$R_{23}$ is a phenyl group optionally substituted by one or more of the following: halogen, —NO$_2$, an alkyl group, and alkenyl group, —OH or —NH$_2$;
$R_{24}$ is hydrogen, —CO-alkyl (preferably methyl) or a phenyl group optionally substituted by one or more of the following: halogen, —NO$_2$, an alkyl group, and alkenyl group, —OH or —NH$_2$;
$R_{25}$ and $R_{26}$ are independently hydrogen, an alkyl group or form a —CH$_2$—CH$_2$— group;
$R_{27}$ is a phenyl group optionally substituted by one or more of the following: halogen, —NO$_2$, an alkyl group, an alkenyl group, —OH or —NH$_2$;
or pharmaceutically acceptable salts, solvates or hydrates thereof.

In a particular embodiment of Formula V, $R_{11}$ is —OH, $R_{12}$ is H and $R_{13}$ is:

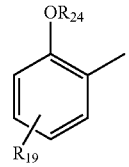

wherein:
$R_{24}$ is hydrogen or —COCH$_3$;
$R_{19}$ is halogen, an alkyl group, —O-alkyl or —NO$_2$.

It is preferred that when $R_{19}$ is —O-alkyl, the alkyl group is a methyl group.

It is preferred that when $R_{19}$ is an alkyl group, the alkyl group is substituted with one or more halogens. For example the substituted alkyl group is —CF$_3$.

Substituted aminomethyl-phenyl-cyclohexane derivatives in accordance with Formula V are further described in U.S. Pat. No. 6,455,585 and published PCT Application WO01/49650, which are incorporated herein by reference.

5-HT$_3$ antagonists that may be employed as additional active agents in the present invention include, but are not limited to:

a. Ondansetron [1,2,3,9-tetrahydro-9-methyl-3-[(2-methyl-1H-imidazol-1-yl]methyl]-4H-carbazol-4-one (cf. Merck Index, twelfth edition, item 6979);

b. Granisetron [endo-1-methyl-N-(9-methyl-9-aza-bicyclo[3.3.1]non-3-yl)-1H-imidazole-3-carboxamide: (cf. Merck Index, twelfth edition, item 4557);

c. Dolasetron [1H-indole-3-carboxylic acid (2.alpha., 6.alpha., 8.alpha., 9.alpha.beta.)-octahydro-3-oxo-2, 6methano-2H-quinolizin-8-yl ester] (cf. Merck Index, twelfth edition, item 3471);

d. Indol-3-yl-carboxylic acid-endo-8-methyl-8-aza-bicyclo[3,2,1]-oct-3-yl-ester, also known as tropisetron. (cf. Merck Index, twelfth edition, item 9914);

e. 4,5,6,7-tetrahydro-5-[(1-methyl-indol-3yl)carbonyl] benzimidazole (see also ramosetron, U.S. Pat. No. 5,344,927);

f. (+)-10-methyl-7-(5-methyl-1H-imidazol-4-ylmethyl)-6,7,8,9-tetrahydropyrido [1,2-a]indol-6-one (see also fabesetron, European Patent No. 0 361 317);

g. [N-(1-ethyl-2-imidazolin-2-yl-methyl)-2-methoxy-4-amino-5-chlorobenzamide (see also lintopride-Chem.-Abstr.-No. 107429-63-0); and h. 2,3,4,5-tetrahydro-5-methyl-2-[(5-methyl-1H-imidazol-4-yl)methyl]-1H-pyrid o[4,3-b]indol-1-one (see also alosetron, European Patent No. 0 306 323).

5-HT$_4$ agonists that may be employed as additional active agents in the present invention include, but are not limited to 2-piperazinylbenzothiazole and 2-piperazinylbenzoxazole derivatives as disclosed in Monge et al. (1994) *J. Med. Chem.* 37: 1320–1325.

Formulations

Formulations of the present invention may include, but are not limited to, continuous, as needed, short-term, rapid-offset, controlled release, sustained release, delayed release, and pulsatile release formulations.

Compositions of the invention comprise sodium channel modulators, particularly tetrodotoxin-resistant (TTX-R) sodium channel modulators and/or activity-dependent sodium channel modulators. TTX-R sodium channel modulators for use in the present invention include but are not limited to compounds that interact with Nav1.8 and/or Nav1.9 channels. The compositions are administered in therapeutically effective amounts to a patient in need thereof for treating a GI tract disorder except for acid peptic disorders or structural gastroesophageal disorders. It is recognized that the compositions may be administered by any means of administration as long as an effective amount for treating a GI tract disorder except for acid peptic disorders or structural gastroesophageal disorders is delivered.

Any of the active agents may be administered in the form of a salt, ester, amide, prodrug, active metabolite, derivative, or the like, provided that the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For example, acid addition salts are prepared from the free base using conventional methodology, and involves reaction with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are salts prepared with organic acids. Conversely, preparation of basic salts of acid moieties which may be present on an active agent are prepared in a similar manner using a pharmaceutically acceptable base such as sodium hydroxide, potassium hydroxide, ammonium hydroxide, calcium hydroxide, trimethylamine, or the like.

Preparation of esters involves functionalization of hydroxyl and/or carboxyl groups that may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety, which results in a compound that is therapeutically inactive until modified by an individual's metabolic system.

Other salts, enantiomers, analogs, esters, amides, prodrugs, active metabolites, and derivatives of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

Pharmaceutical Compositions and Dosage Forms

Suitable compositions and dosage forms include tablets, capsules, caplets, pills, gel caps, troches, dispersions, suspensions, solutions, syrups, transdermal patches, gels, powders, magmas, lozenges, creams, pastes, plasters, lotions, discs, suppositories, liquid sprays for nasal or oral administration, dry powder or aerosolized formulations for inhalation, compositions and formulations for intravesical administration and the like. Further, those of ordinary skill in the art can readily deduce that suitable formulations involving these compositions and dosage forms, including those formulations as described elsewhere herein.

Oral Dosage Forms

Oral dosage forms include tablets, capsules, caplets, solutions, suspensions and/or syrups, and may also comprise a plurality of granules, beads, powders or pellets that may or may not be encapsulated. Such dosage forms are prepared using conventional methods known to those in the field of pharmaceutical formulation and described in the pertinent texts, e.g., in Remington: The Science and Practice of Pharmacy, supra). Tablets and capsules represent the most convenient oral dosage forms, in which case solid pharmaceutical carriers are employed.

Tablets may be manufactured using standard tablet processing procedures and equipment. One method for forming tablets is by direct compression of a powdered, crystalline or granular composition containing the active agent(s), alone or in combination with one or more carriers, additives, or the like. As an alternative to direct compression, tablets can be prepared using wet-granulation or dry-granulation processes. Tablets may also be molded rather than compressed, starting with a moist or otherwise tractable material; however, compression and granulation techniques are preferred.

In addition to the active agent(s), then, tablets prepared for oral administration using the method of the invention will generally contain other materials such as binders, diluents, lubricants, disintegrants, fillers, stabilizers, surfactants, preservatives, coloring agents, flavoring agents and the like. Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), and Veegum. Diluents are typically necessary to increase bulk so that a practical size tablet is ultimately provided. Suitable diluents include dicalcium phosphate, calcium sulfate, lactose, cellulose, kaolin, mannitol, sodium chloride, dry starch and powdered sugar. Lubricants are used to facilitate tablet manufacture; examples of suitable lubricants include, for example, vegetable oils such as peanut oil, cottonseed oil, sesame oil, olive oil, corn oil, and oil of theobroma, glycerin, magnesium stearate, calcium stearate, and stearic acid. Stearates, if present, preferably represent at no more than approximately 2 wt. % of the drug-containing core. Disintegrants are used to facilitate disintegration of the tablet, and are generally starches, clays, celluloses, algins, gums or crosslinked polymers. Fillers include, for example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. Stabilizers are used to inhibit or retard drug decomposition reactions that include, by way of example, oxidative reactions. Surfactants may be anionic, cationic, amphoteric or nonionic surface active agents.

The dosage form may also be a capsule, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. (See, for e.g., Remington: The Science and Practice of Pharmacy, supra), which describes materials and methods for preparing encapsulated pharmaceuticals. If the active agent-containing composition is present within the capsule in liquid form, a liquid carrier is necessary to dissolve the active agent(s). The carrier must be compatible with the capsule material and all components of the pharmaceutical composition, and must be suitable for ingestion.

Solid dosage forms, whether tablets, capsules, caplets, or particulates, may, if desired, be coated so as to provide for delayed release. Dosage forms with delayed release coatings may be manufactured using standard coating procedures and equipment. Such procedures are known to those skilled in the art and described in the pertinent texts (See, for e.g., Remington: The Science and Practice of Pharmacy, supra). Generally, after preparation of the solid dosage form, a delayed release coating composition is applied using a coating pan, an airless spray technique, fluidized bed coating equipment, or the like. Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof.

Sustained release dosage forms provide for drug release over an extended time period, and may or may not be delayed release. Generally, as will be appreciated by those of ordinary skill in the art, sustained release dosage forms are formulated by dispersing a drug within a matrix of a gradually bioerodible (hydrolyzable) material such as an insoluble plastic, a hydrophilic polymer, or a fatty compound, or by coating a solid, drug-containing dosage form with such a material. Insoluble plastic matrices may be comprised of, for example, polyvinyl chloride or polyethylene. Hydrophilic polymers useful for providing a sustained release coating or matrix cellulosic polymers include, without limitation: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylcellulose phthalate, cellulose hexahydrophthalate, cellulose acetate hexahydrophthalate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, with a terpolymer of ethyl acrylate, methyl methacrylate and trimethylammonioethyl methacrylate chloride (sold under the tradename Eudragit RS) preferred; vinyl polymers and copolymers such as polyvinyl pyrrolidone, polyvinyl acetate, polyvinylacetate phthalate, vinylacetate crotonic acid copolymer, and ethylene-vinyl acetate copolymers; zein; and shellac, ammoniated shellac, shellac-acetyl alcohol, and shellac n-butyl stearate. Fatty compounds for use as a sustained release matrix material include, but are not limited to, waxes generally (e.g., carnauba wax) and glyceryl tristearate.

Transmucosal Compositions and Dosage Forms

Although the present compositions may be administered orally, other modes of administration are suitable as well. For example, transmucosal administration may be advantageously employed. Transmucosal administration is carried out using any type of formulation or dosage unit suitable for application to mucosal tissue. For example, the selected active agent may be administered to the buccal mucosa in an adhesive tablet or patch, sublingually administered by placing a solid dosage form under the tongue, lingually administered by placing a solid dosage form on the tongue, administered nasally as droplets or a nasal spray, administered by inhalation of an aerosol formulation, a non-aerosol liquid formulation, or a dry powder, placed within or near the rectum ("transrectal" formulations), or administered to the urethra as a suppository, ointment, or the like.

Preferred buccal dosage forms will typically comprise a therapeutically effective amount of an active agent and a bioerodible (hydrolyzable) polymeric carrier that may also serve to adhere the dosage form to the buccal mucosa. The buccal dosage unit is fabricated so as to erode over a predetermined time period, wherein drug delivery is provided essentially throughout. The time period is typically in the range of from about 1 hour to about 72 hours. Preferred buccal delivery preferably occurs over a time period of from about 2 hours to about 24 hours. Buccal drug delivery for short term use should preferably occur over a time period of from about 2 hours to about 8 hours, more preferably over a time period of from about 3 hours to about 4 hours. As needed buccal drug delivery preferably will occur over a time period of from about 1 hour to about 12 hours, more preferably from about 2 hours to about 8 hours, most preferably from about 3 hours to about 6 hours. Sustained buccal drug delivery will preferably occur over a time period of from about 6 hours to about 72 hours, more preferably from about 12 hours to about 48 hours, most preferably from about 24 hours to about 48 hours. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver.

The "therapeutically effective amount" of the active agent in the buccal dosage unit will of course depend on the potency of the agent and the intended dosage, which, in turn, is dependent on the particular individual undergoing treatment, the specific indication, and the like. The buccal dosage unit will generally contain from about 1.0 wt. % to about 60 wt. % active agent, preferably on the order of from about 1 wt. % to about 30 wt. % active agent. With regard to the bioerodible (hydrolyzable) polymeric carrier, it will be appreciated that virtually any such carrier can be used, so long as the desired drug release profile is not compromised, and the carrier is compatible with the sodium channel modulator, particularly tetrodotoxin-resistant (TTX-R) sodium channel modulator and/or activity-dependent sodium channel modulator, to be administered and any other components of the buccal dosage unit. Generally, the polymeric carrier comprises a hydrophilic (water-soluble and water-swellable) polymer that adheres to the wet surface of the buccal mucosa. Examples of polymeric carriers useful herein include acrylic acid polymers and co, e.g., those known as "carbomers" (Carbopol®, which may be obtained from B. F. Goodrich, is one such polymer). Other suitable polymers include, but are not limited to: hydrolyzed polyvinylalcohol; polyethylene oxides (e.g., Sentry Polyox® water soluble resins, available from Union Carbide); polyacrylates (e.g., Gantrez®, which may be obtained from GAF); vinyl polymers and copolymers; polyvinylpyrrolidone; dextran; guar gum; pectins; starches; and cellulosic polymers such as hydroxypropyl methylcellulose, (e.g., Methocel®, which may be obtained from the Dow Chemical Company), hydroxypropyl cellulose (e.g., Klucel®, which may also be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methyl cellulose, ethyl cellulose, cellulose acetate phthalate, cellulose acetate butyrate, and the like.

Other components may also be incorporated into the buccal dosage forms described herein. The additional components include, but are not limited to, disintegrants, diluents, binders, lubricants, flavoring, colorants, preservatives, and the like. Examples of disintegrants that may be used include, but are not limited to, cross-linked polyvinylpyrrolidones, such as crospovidone (e.g., Polyplasdone® XL, which may be obtained from GAF), cross-linked carboxylic methylcelluloses, such as croscarmelose (e.g., Ac-di-sol®, which may be obtained from FMC), alginic acid, and sodium carboxymethyl starches (e.g., Explotab®, which may be obtained from Edward Medell Co., Inc.), methylcellulose, agar bentonite and alginic acid. Suitable diluents are those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pak®, which may be obtained from Amstar), calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Particularly preferred lubricants are stearates and stearic acid, and an optimal lubricant is magnesium stearate.

Sublingual and lingual dosage forms include tablets, creams, ointments, lozenges, pastes, and any other solid dosage form where the active ingredient is admixed into a disintegrable matrix. The tablet, cream, ointment or paste for sublingual or lingual delivery comprises a therapeutically effective amount of the selected active agent and one or more conventional nontoxic carriers suitable for sublingual or lingual drug administration. The sublingual and lingual dosage forms of the present invention can be manufactured using conventional processes. The sublingual and lingual dosage units are fabricated to disintegrate rapidly. The time period for complete disintegration of the dosage unit is typically in the range of from about 10 seconds to about 30 minutes, and optimally is less than 5 minutes.

Other components may also be incorporated into the sublingual and lingual dosage forms described herein. The additional components include, but are not limited to binders, disintegrants, wetting agents, lubricants, and the like. Examples of binders that may be used include water, ethanol, polyvinylpyrrolidone; starch solution gelatin solution, and the like. Suitable disintegrants include dry starch, calcium carbonate, polyoxyethylene sorbitan fatty acid esters, sodium lauryl sulfate, stearic monoglyceride, lactose, and the like. Wetting agents, if used, include glycerin, starches, and the like. Particularly preferred lubricants are stearates and polyethylene glycol. Additional components that may be incorporated into sublingual and lingual dosage forms are known, or will be apparent, to those skilled in this art (See, e.g., Remington: The Science and Practice of Pharmacy, supra).

For transurethral administration, the formulation comprises a urethral dosage form containing the active agent and one or more selected carriers or excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred.

Depending on the particular active agent administered, it may be desirable to incorporate a transurethral permeation enhancer in the urethral dosage form. Examples of suitable transurethral permeation enhancers include dimethylsulfoxide ("DMSO"), dimethyl formamide ("DMF"), N,N-dimethylacetamide ("DMA"), decylmethylsulfoxide ("$C_{10}$ MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), SEPA® (available from Macrochem Co., Lexington, Mass.), surfactants as discussed above, including, for example, Tergitol®, Nonoxynol-9® and TWEEN-80®, and lower alkanols such as ethanol.

Transurethral drug administration, as explained in U.S. Pat. Nos. 5,242,391, 5,474,535, 5,686,093 and 5,773,020, can be carried out in a number of different ways using a variety of urethral dosage forms. For example, the drug can be introduced into the urethra from a flexible tube, squeeze bottle, pump or aerosol spray. The drug may also be contained in coatings, pellets or suppositories that are absorbed, melted or bioeroded in the urethra. In certain embodiments, the drug is included in a coating on the exterior surface of a penile insert. It is preferred, although not essential, that the drug be delivered from at least about 3 cm into the urethra, and preferably from at least about 7 cm into the urethra. Generally, delivery from at least about 3 cm to about 8 cm into the urethra will provide effective results in conjunction with the present method.

Urethral suppository formulations containing PEG or a PEG derivative may be conveniently formulated using conventional techniques, e.g., compression molding, heat molding or the like, as will be appreciated by those skilled in the art and as described in the pertinent literature and pharmaceutical texts. (See, e.g., Remington: The Science and Practice of Pharmacy, supra), which discloses typical methods of preparing pharmaceutical compositions in the form of urethral suppositories. The PEG or PEG derivative preferably has a molecular weight in the range of from about 200 to about 2,500 g/mol, more preferably in the range of from about 1,000 to about 2,000 g/mol. Suitable polyethylene glycol derivatives include polyethylene glycol fatty acid esters, for example, polyethylene glycol monostearate, polyethylene glycol sorbitan esters, e.g., polysorbates, and the like. Depending on the particular active agent, it may also be preferred that urethral suppositories contain one or more solubilizing agents effective to increase the solubility of the active agent in the PEG or other transurethral vehicle.

It may be desirable to deliver the active agent in a urethral dosage form that provides for controlled or sustained release of the agent. In such a case, the dosage form comprises a biocompatible, biodegradable material, typically a biodegradable polymer. Examples of such polymers include polyesters, polyalkylcyanoacrylates, polyorthoesters, polyanhydrides, albumin, gelatin and starch. As explained, for example, in PCT Publication No. WO 96/40054, these and other polymers can be used to provide biodegradable microparticles that enable controlled and sustained drug release, in turn minimizing the required dosing frequency.

The urethral dosage form will preferably comprise a suppository that is on the order of from about 2 to about 20 mm in length, preferably from about 5 to about 10 mm in length, and less than about 5 mm in width, preferably less than about 2 mm in width. The weight of the suppository will typically be in the range of from about 1 mg to about 100 mg, preferably in the range of from about 1 mg to about 50 mg. However, it will be appreciated by those skilled in the art that the size of the suppository can and will vary, depending on the potency of the drug, the nature of the formulation, and other factors.

Transurethral drug delivery may involve an "active" delivery mechanism such as iontophoresis, electroporation or phonophoresis. Devices and methods for delivering drugs in this way are well known in the art. Iontophoretically assisted drug delivery is, for example, described in PCT Publication No. WO 96/40054, cited above. Briefly, the active agent is driven through the urethral wall by means of an electric current passed from an external electrode to a second electrode contained within or affixed to a urethral probe.

Preferred transrectal dosage forms include rectal suppositories, creams, ointments, and liquid formulations (enemas). The suppository, cream, ointment or liquid formulation for transrectal delivery comprises a therapeutically effective amount of the selected phosphodiesterase inhibitor and one or more conventional nontoxic carriers suitable for transrectal drug administration. The transrectal dosage forms of the present invention can be manufactured using conventional processes. The transrectal dosage unit can be fabricated to disintegrate rapidly or over a period of several hours. The time period for complete disintegration is preferably in the range of from about 10 minutes to about 6 hours, and optimally is less than about 3 hours.

Other components may also be incorporated into the transrectal dosage forms described herein. The additional components include, but are not limited to, stiffening agents, antioxidants, preservatives, and the like. Examples of stiffening agents that may be used include, for example, paraffin, white wax and yellow wax. Preferred antioxidants, if used, include sodium bisulfite and sodium metabisulfite.

Preferred vaginal or perivaginal dosage forms include vaginal suppositories, creams, ointments, liquid formulations, pessaries, tampons, gels, pastes, foams or sprays. The suppository, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention can be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit can be fabricated to disintegrate rapidly or over a period of several hours. The time period for complete disintegration is preferably in the range of from about 10 minutes to about 6 hours, and optimally is less than about 3 hours.

Other components may also be incorporated into the vaginal or perivaginal dosage forms described herein. The additional components include, but are not limited to, stiffening agents, antioxidants, preservatives, and the like. Examples of stiffening agents that may be used include, for example, paraffin, white wax and yellow wax. Preferred antioxidants, if used, include sodium bisulfite and sodium metabisulfite.

The active agents may also be administered intranasally or by inhalation. Compositions for intranasal administration are generally liquid formulations for administration as a spray or in the form of drops, although powder formulations for intranasal administration, e.g., insufflations, are also known, as are nasal gels, creams, pastes or ointments. For liquid formulations, the active agent can be formulated into a solution, e.g., water or isotonic saline, buffered or unbuffered, or as a suspension. Preferably, such solutions or suspensions are isotonic relative to nasal secretions and of about the same pH, ranging e.g., from about pH 4.0 to about pH 7.4 or, from about pH 6.0 to about pH 7.0. Buffers should be physiologically compatible and include, simply by way of example, phosphate buffers. Furthermore, various devices are available in the art for the generation of drops, droplets and sprays, including droppers, squeeze bottles, and manually and electrically powered intranasal pump dispensers. Active agent containing intranasal carriers may also include nasal gels, creams, pastes or ointments with a viscosity of, e.g., from about 10 to about 6500 cps, or greater, depending on the desired sustained contact with the nasal mucosal surfaces. Such carrier viscous formulations may be based upon, simply by way of example, alkylcelluloses and/or other biocompatible carriers of high viscosity well known to the art (see e.g., Remington: The Science and Practice of Pharmacy, supra). Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation.

Formulations for inhalation may be prepared as an aerosol, either a solution aerosol in which the active agent is solubilized in a carrier (e.g., propellant) or a dispersion aerosol in which the active agent is suspended or dispersed throughout a carrier and an optional solvent. Non-aerosol formulations for inhalation may take the form of a liquid, typically an aqueous suspension, although aqueous solutions may be used as well. In such a case, the carrier is typically a sodium chloride solution having a concentration such that the formulation is isotonic relative to normal body fluid. In addition to the carrier, the liquid formulations may contain water and/or excipients including an antimicrobial preservative (e.g., benzalkonium chloride, benzethonium chloride, chlorobutanol, phenylethyl alcohol, thimerosal and combinations thereof), a buffering agent (e.g., citric acid, potassium metaphosphate, potassium phosphate, sodium acetate, sodium citrate, and combinations thereof), a surfactant (e.g., polysorbate 80, sodium lauryl sulfate, sorbitan monopalmitate and combinations thereof), and/or a suspending agent (e.g., agar, bentonite, microcrystalline cellulose, sodium carboxymethylcellulose, hydroxypropyl methylcellulose, tragacanth, veegum and combinations thereof). Non-aerosol formulations for inhalation may also comprise dry powder formulations, particularly insufflations in which the powder has an average particle size of from about 0.1 μm to about 50 μm, preferably from about 1 μm to about 25 μm.

Topical Formulations

Topical formulations may be in any form suitable for application to the body surface, and may comprise, for example, an ointment, cream, gel, lotion, solution, paste or the like, and/or may be prepared so as to contain liposomes, micelles, and/or microspheres. Preferred topical formulations herein are ointments, creams and gels.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, supra, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight (See, e.g., Remington: The Science and Practice of Pharmacy, supra).

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels-are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

Various additives, known to those skilled in the art, may be included in the topical formulations. For example, solubilizers may be used to solubilize certain active agents. For those drugs having an unusually low rate of permeation through the skin or mucosal tissue, it may be desirable to include a permeation enhancer in the formulation; suitable enhancers are as described elsewhere herein.

Transdermal Administration

The compounds of the invention may also be administered through the skin or mucosal tissue using conventional transdermal drug delivery systems, wherein the agent is contained within a laminated structure (typically referred to as a transdermal "patch") that serves as a drug delivery device to be affixed to the skin. Transdermal drug delivery may involve passive diffusion or it may be facilitated using electrotransport, e.g., iontophoresis. In a typical transdermal "patch," the drug composition is contained in a layer, or "reservoir," underlying an upper backing layer. The laminated structure may contain a single reservoir, or it may contain multiple reservoirs. In one type of patch, referred to as a "monolithic" system, the reservoir is comprised of a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active agent and any other materials that are present, the backing is preferably made of a sheet or film of a flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Transdermal drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well known in the art and include, for example, those enhancers listed above in transmucosal compositions.

Parenteral Administration

Parenteral administration, if used, is generally characterized by injection, including intramuscular, intraperitoneal, intravenous (IV) and subcutaneous injection. Injectable formulations can be prepared in conventional forms, either as liquid solutions or suspensions; solid forms suitable for solution or suspension in liquid prior to injection, or as emulsions. Preferably, sterile injectable suspensions are formulated according to techniques known in the art using suitable dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. A more recently revised approach for parenteral administration involves use of a slow release or sustained release system (See, e.g., U.S. Pat. No. 3,710,795).

Intrathecal Administration

Intrathecal administration, if used, is generally characterized by administration directly into the intrathecal space (where fluid flows around the spinal cord).

One common system utilized for intrathecal administration is the APT Intrathecal treatment system available from Medtronic, Inc. APT Intrathecal uses a small pump that is surgically placed under the skin of the abdomen to deliver medication directly into the intrathecal space. The medication is delivered through a small tube called a catheter that is also surgically placed. The medication can then be administered directly to cells in the spinal cord involved in conveying sensory and motor signals associated with GI tract disorders.

Another system available from Medtronic that is commonly utilized for intrathecal administration is the is the fully implantable, programmable SynchroMed® Infusion System. The SynchroMed® Infusion System has two parts that are both placed in the body during a surgical procedure: the catheter and the pump. The catheter is a small, soft tube. One end is connected to the catheter port of the pump, and the other end is placed in the intrathecal space. The pump is a round metal device about one inch (2.5 cm) thick, three inches (8.5 cm) in diameter, and weighs about six ounces (205 g) that stores and releases prescribed amounts of medication directly into the intrathecal space. It is made of titanium, a lightweight, medical-grade metal. The reservoir is the space inside the pump that holds the medication. The fill port is a raised center portion of the pump through which the pump is refilled. The doctor or a nurse inserts a needle through the patient's skin and through the fill port to fill the pump. Some pumps have a side catheter access port that allows the doctor to inject other medications or sterile solutions directly into the catheter, bypassing the pump.

The SynchroMed® pump automatically delivers a controlled amount of medication through the catheter to the intrathecal space around the spinal cord, where it is most effective. The exact dosage, rate and timing prescribed by the doctor are entered in the pump using a programmer, an external computer-like device that controls the pump's memory. Information about the patient's prescription is stored in the pump's memory. The doctor can easily review this information by using the programmer. The programmer communicates with the pump by radio signals that allow the doctor to tell how the pump is operating at any given time. The doctor also can use the programmer to change your medication dosage.

Methods of intrathecal administration may include those described above available from Medtronic, as well as other methods that are known to one of skill in the art.

Additional Dosage Formulations and Drug Delivery Systems

As compared with traditional drug delivery approaches, some controlled release technologies rely upon the modification of both macromolecules and synthetic small molecules to allow them to be actively instead of passively absorbed into the body. For example, XenoPort Inc. utilizes technology that takes existing molecules and re-engineers them to create new chemical entities (unique molecules) that have improved pharmacologic properties to either: 1) lengthen the short half-life of a drug; 2) overcome poor absorption; and/or 3) deal with poor drug distribution to target tissues. Techniques to lengthen the short half-life of a drug include the use of prodrugs with slow cleavage rates to release drugs over time or that engage transporters in small and large intestines to allow the use of oral sustained delivery systems, as well as drugs that engage active transport systems. Examples of such controlled release formulations, tablets, dosage forms, and drug delivery systems, and that are suitable for use with the present invention, are described in the following published US and PCT patent applications assigned to Xenoport Inc.: US 20030158254; US 20030158089; US 20030017964; US 2003130246; WO02100172; WO02100392; WO02100347; WO02100344; WO0242414; WO0228881; WO0228882; WO0244324; WO0232376; WO0228883; and WO0228411. Some other controlled release technologies rely upon methods that promote or enhance gastric retention, such as those developed by Depomed Inc. Because many drugs are best absorbed in the stomach and upper portions of the small intestine, Depomed has developed tablets that swell in the stomach during the postprandial or fed mode so that they are treated like undigested food. These tablets therefore sit safely and neutrally in the stomach for 6, 8, or more hours and deliver drug at a desired rate and time to upper gastrointestinal sites. Specific technologies in this area include: 1) tablets that slowly erode in gastric fluids to deliver drugs at almost a constant rate (particularly useful for highly insoluble drugs); 2) bi-layer tablets that combine drugs with different characteristics into a single table (such as a highly insoluble drug in an erosion layer and a soluble drug in a diffusion layer for sustained release of both); and 3) combination tablets that can either deliver drugs simultaneously or in sequence over a desired period of time (including an initial burst of a fast acting drug followed by slow and sustained delivery of another drug). Examples of such controlled release formulations that are suitable for use with the present invention and that rely upon gastric retention during the postprandial or fed mode, include tablets, dosage forms, and drug delivery systems in the following US patents assigned to Depomed Inc.: U.S. Pat. Nos. 6,488,962; 6,451,808; 6,340,475; 5,972,389; 5,582,837; and 5,007,790. Examples of such controlled release formulations that are suitable for use with the present invention and that rely upon gastric retention during the postprandial or fed mode, include tablets, dosage forms, and drug delivery systems in the following published US and PCT patent applications assigned to Depomed Inc.: US 20030147952; US 20030104062; US 20030104053; US 20030104052; US 20030091630; US 20030044466; US 20030039688; US 20020051820; WO0335040; WO0335039; WO0156544; WO0132217; WO9855107; WO9747285; and WO9318755.

Other controlled release systems include those developed by ALZA Corporation based upon: 1) osmotic technology for oral delivery; 2) transdermal delivery via patches; 3) liposomal delivery via intravenous injection; 4) osmotic technology for long-term delivery via implants; and 5) depot technology designed to deliver agents for periods of days to a month. ALZA oral delivery systems include those that employ osmosis to provide precise, controlled drug delivery for up to 24 hours for both poorly soluble and highly soluble drugs, as well as those that deliver high drug doses meeting high drug loading requirements. ALZA controlled transdermal delivery systems provide drug delivery through intact skin for as long as one week with a single application to improve drug absorption and deliver constant amounts of drug into the bloodstream over time. ALZA liposomal delivery systems involve lipid nanoparticles that evade recognition by the immune system because of their unique polyethylene glycol (PEG) coating, allowing the precise delivery of drugs to disease-specific areas of the body. ALZA also has developed osmotically driven systems to enable the continuous delivery of small drugs, peptides, proteins, DNA and other bioactive macromolecules for up to one year for systemic or tissue-specific therapy. Finally, ALZA depot injection therapy is designed to deliver biopharmaceutical agents and small molecules for periods of days to a month using a nonaqueous polymer solution for the stabilization of macromolecules and a unique delivery profile.

Examples of controlled release formulations, tablets, dosage forms, and drug delivery systems that are suitable for use with the present invention are described in the following US patents assigned to ALZA Corporation: U.S. Pat. Nos. 4,367,741; 4,402,695; 4,418,038; 4,434,153; 4,439,199; 4,450,198; 4,455,142; 4,55,144; 4,484,923; 4,486,193; 4,489,197; 4,511,353; 4,519,801; 4,526,578; 4,526,933; 4,534,757; 4,553,973; 4,559,222; 4,564,364; 4,578,075; 4,588,580; 4,610,686; 4,618,487; 4,627,851; 4,629,449; 4,642,233; 4,649,043; 4,650,484; 4,659,558; 4,661,105; 4,662,880; 4,675,174; 4,681,583; 4,684,524; 4,692,336; 4,693,895; 4,704,119; 4,705,515; 4,717,566; 4,721,613; 4,723,957; 4,725,272; 4,728,498; 4,743,248; 4,747,847; 4,751,071; 4,753,802; 4,755,180; 4,756,314; 4,764,380; 4,773,907; 4,777,049; 4,781,924; 4,786,503; 4,788,062; 4,810,502; 4,812,313; 4,816,258; 4,824,675; 4,834,979; 4,837,027; 4,842,867; 4,846,826; 4,847,093; 4,849,226; 4,851,229; 4,851,231; 4,851,232; 4,853,229; 4,857,330; 4,859,470; 4,863,456; 4,863,744; 4,865,598; 4,867,969; 4,871,548; 4,872,873; 4,874,388; 4,876,093; 4,892,778; 4,902,514; 4,904,474; 4,913,903; 4,915,949; 4,915,952; 4,917,895; 4,931,285; 4,946,685; 4,948,592; 4,954,344; 4,957,494; 4,960,416; 4,961,931; 4,961,932; 4,963,141; 4,966,769; 4,971,790; 4,976,966; 4,986,987; 5,006,346; 5,017,381; 5,019,397; 5,023,076; 5,023,088; 5,024,842; 5,028,434; 5,030,454; 5,071,656; 5,077,054; 5,082,668; 5,104,390; 5,110,597; 5,122,128; 5,125,894; 5,141,750; 5,141,752; 5,156,850; 5,160,743; 5,160,744; 5,169,382; 5,171,576; 5,176,665; 5,185,158; 5,190,765; 5,198,223; 5,198,229; 5,200,195; 5,200,196; 5,204,116; 5,208,037; 5,209,746; 5,221,254; 5,221,278; 5,229,133; 5,232,438; 5,232,705; 5,236,689; 5,236,714; 5,240,713; 5,246,710; 5,246,711; 5,252,338; 5,254,349; 5,266,332; 5,273,752; 5,284,660; 5,286,491; 5,308,348; 5,318,558; 5,320,850; 5,322,502; 5,326,571; 5,330,762; 5,338,550; 5,340,590; 5,342,623; 5,344,656; 5,348,746; 5,358,721; 5,364,630; 5,376,377; 5,391,381; 5,402,777; 5,403,275; 5,411,740; 5,417,675; 5,417,676; 5,417,682; 5,423,739; 5,424,289; 5,431,919; 5,443,442; 5,443,459; 5,443,461; 5,456,679; 5,460,826; 5,462,741; 5,462,745; 5,489,281; 5,499,979; 5,500,222; 5,512,293; 5,512,299; 5,529,787; 5,531,736; 5,532,003; 5,533,971; 5,534,263; 5,540,912; 5,543,156; 5,571,525; 5,573,503; 5,591,124; 5,593,695; 5,595,759; 5,603,954; 5,607,696; 5,609,885; 5,614,211; 5,614,578; 5,620,705; 5,620,708; 5,622,530; 5,622,944; 5,633,011; 5,639,477; 5,660,861; 5,667,804; 5,667,805; 5,674,895; 5,688,518; 5,698,224; 5,702,725; 5,702,727; 5,707,663; 5,713,852; 5,718,700; 5,736,580; 5,770,227; 5,780,058; 5,783,213; 5,785,994; 5,795,591; 5,811,465; 5,817,624; 5,824,340; 5,830,501; 5,830,502; 5,840,754; 5,858,407; 5,861,439; 5,863,558; 5,876,750; 5,883,135; 5,897,878; 5,904,934; 5,904,935; 5,906,832; 5,912,268; 5,914,131; 5,916,582; 5,932,547; 5,938,654; 5,941,844; 5,955,103; 5,972,369; 5,972,370; 5,972,379; 5,980,943; 5,981,489; 5,983,130; 5,989,590; 5,995,869; 5,997,902; 6,001,390; 6,004,309; 6,004,578; 6,008,187; 6,020,000; 6,034,101; 6,036,973; 6,039,977; 6,057,374; 6,066,619; 6,068,850; 6,077,538; 6,083,190; 6,096,339; 6,106,845; 6,110,499; 6,120,798; 6,120,803; 6,124,261; 6,130,200; 6,146,662; 6,153,678; 6,174,547; 6,183,466; 6,203,817; 6,210,712; 6,210,713; 6,224,907; 6,235,712; 6,245,357; 6,262,115; 6,264,990; 6,267,984; 6,287,598; 6,289,241; 6,331,311; 6,333,050; 6,342,249; 6,346,270; 6,365,183; 6,368,626; 6,387,403; 6,419,952; 6,440,457; 6,468,961; 6,491,683; 6,512,010; 6,514,530; 6,534,089; 6,544,252; 6,551,613; 6,572,879; and 6,596,314.

Other examples of controlled release formulations, tablets, dosage forms, and drug delivery systems that are suitable for use with the present invention are described in the following published US patent application and PCT applications assigned to ALZA Corporation: US 20010051183; WO0004886; WO0013663; WO0013674; WO0025753; WO0025790; WO0035419; WO0038650; WO0040218; WO0045790; WO0066126; WO0074650; WO0119337; WO019352; WO0121211; WO0137815; WO0141742; WO0143721; WO0156543; WO3041684; WO03041685; WO03041757; WO03045352; WO03051341; WO03053400; WO03053401; WO9000416; WO9004965; WO9113613; WO9116884; WO9204011; WO9211843; WO9212692; WO9213521; WO9217239; WO9218102; WO9300071; WO9305843; WO9306819; WO9314813; WO9319739; WO9320127; WO9320134; WO9407562; WO9408572; WO9416699; WO9421262; WO9427587; WO9427589; WO9503823; WO9519174; WO9529665; WO9600065; WO9613248; WO9625922; WO9637202; WO9640049; WO9640050; WO9640139; WO9640364; WO9640365; WO9703634; WO9800158; WO9802169; WO9814168; WO9816250; WO9817315; WO9827962; WO9827963; WO9843611; WO9907342; WO9912526; WO9912527; WO9918159; WO9929297;

WO9929348; WO9932096; WO9932153; WO9948494; WO9956730; WO9958115; and WO9962496.

Andrx Corporation has also developed drug delivery technology suitable for use in the present invention that includes: 1) a pelletized pulsatile delivery system ("PPDS"); 2) a single composition osmotic tablet system ("SCOT"); 3) a solubility modulating hydrogel system ("SMHS"); 4) a delayed pulsatile hydrogel system ("DPHS"); 5) a stabilized pellet delivery system ("SPDS"); 6) a granulated modulating hydrogel system ("GMHS"); 7) a pelletized tablet system ("PELTAB"); 8) a porous tablet system ("PORTAB"); and 9) a stabilized tablet delivery system ("STDS"). PPDS uses pellets that are coated with specific polymers and agents to control the release rate of the microencapsulated drug and is designed for use with drugs that require a pulsed release. SCOT utilizes various osmotic modulating agents as well as polymer coatings to provide a zero-order drug release. SMHS utilizes a hydrogel-based dosage system that avoids the "initial burst effect" commonly observed with other sustained-release hydrogel formulations and that provides for sustained release without the need to use special coatings or structures that add to the cost of manufacturing. DPHS is designed for use with hydrogel matrix products characterized by an initial zero-order drug release followed by a rapid release that is achieved by the blending of selected hydrogel polymers to achieve a delayed pulse. SPDS incorporates a pellet core of drug and protective polymer outer layer, and is designed specifically for unstable drugs, while GMHS incorporates hydrogel and binding polymers with the drug and forms granules that are pressed into tablet form. PELTAB provides controlled release by using a water insoluble polymer to coat discrete drug crystals or pellets to enable them to resist the action of fluids in the gastrointestinal tract, and these coated pellets are then compressed into tablets. PORTAB provides controlled release by incorporating an osmotic core with a continuous polymer coating and a water soluble component that expands the core and creates microporous channels through which drug is released. Finally, STDS includes a dual layer coating technique that avoids the need to use a coating layer to separate the enteric coating layer from the omeprazole core.

Examples of controlled release formulations, tablets, dosage forms, and drug delivery systems that are suitable for use with the present invention are described in the following US patents assigned to Andrx Corporation: U.S. Pat. Nos. 5,397,574; 5,419,917; 5,458,887; 5,458,888; 5,472,708; 5,508,040; 5,558,879; 5,567,441; 5,654,005; 5,728,402; 5,736,159; 5,830,503; 5,834,023; 5,837,379; 5,916,595; 5,922,352; 6,099,859; 6,099,862; 6,103,263; 6,106,862; 6,156,342; 6,177,102; 6,197,347; 6,210,716; 6,238,703; 6,270,805; 6,284,275; 6,485,748; 6,495,162; 6,524,620; 6,544,556; 6,589,553; 6,602,522; and 6,610,326.

Examples of controlled release formulations, tablets, dosage forms, and drug delivery systems that are suitable for use with the present invention are described in the following published US and PCT patent applications assigned to Andrx Corporation: US 20010024659; US 20020115718; US 20020156066; WO0004883; WO0009091; WO0012097; WO0027370; WO0050010; WO0132161; WO0134123; WO0236077; WO0236100; WO02062299; WO02062824; WO02065991; WO02069888; WO02074285; WO03000177; WO9521607; WO9629992; WO9633700; WO9640080; WO9748386; WO9833488; WO9833489; WO9930692; WO9947125; and WO9961005.

Some other examples of drug delivery approaches focus on non-oral drug delivery, providing parenteral, transmucosal, and topical delivery of proteins, peptides, and small molecules. For example, the Atrigel® drug delivery system marketed by Atrix Laboratories Inc. comprises biodegradable polymers, similar to those used in biodegradable sutures, dissolved in biocompatible carriers. These pharmaceuticals may be blended into a liquid delivery system at the time of manufacturing or, depending upon the product, may be added later by a physician at the time of use. Injection of the liquid product subcutaneously or intramuscularly through a small gauge needle, or placement into accessible tissue sites through a cannula, causes displacement of the carrier with water in the tissue fluids, and a subsequent precipitate to form from the polymer into a solid film or implant. The drug encapsulated within the implant is then released in a controlled manner as the polymer matrix biodegrades over a period ranging from days to months. Examples of such drug delivery systems include Atrix's Eligard®, Atridox®/Doxirobe®, Atrisorb® FreeFlow™/Atrisorb®-D FreeFlow, bone growth products, and others as described in the following published US and PCT patent applications assigned to Atrix Laboratories Inc.: U.S. Pat. Nos. RE 37950; 6,630,155; 6,566,144; 6,610,252; 6,565,874; 6,528,080; 6,461,631; 6,395,293; 6,261,583; 6,143,314; 6,120,789; 6,071,530; 5,990,194; 5,945,115; 5,888,533; 5,792,469; 5,780,044; 5,759,563; 5,744,153; 5,739,176; 5,736,152; 5,733,950; 5,702,716; 5,681,873; 5,660,849; 5,599,552; 5,487,897; 5,368,859; 5,340,849; 5,324,519; 5,278,202; 5,278,201; US 20020114737, US 20030195489; US 20030133964; US 20010042317; US 20020090398; US 20020001608; and US 2001042317.

Atrix Laboratories Inc. also markets technology for the non-oral transmucosal delivery of drugs over a time period from minutes to hours. For example, Atrix's BEMA™ (Bioerodible Muco-Adhesive Disc) drug delivery system comprises pre-formed bioerodible discs for local or systemic delivery. Examples of such drug delivery systems include those as described in U.S. Pat. No. 6,245,345.

Other drug delivery systems marketed by Atrix Laboratories Inc. focus on topical drug delivery. For example, SMP™ (Solvent Particle System) allows the topical delivery of highly water-insoluble drugs. This product allows for a controlled amount of a dissolved drug to permeate the epidermal layer of the skin by combining the dissolved drug with a microparticle suspension of the drug. The SMP™ system works in stages whereby: 1) the product is applied to the skin surface; 2) the product near follicles concentrates at the skin pore; 3) the drug readily partitions into skin oils; and 4) the drug diffuses throughout the area. By contrast, MCA® (Mucocutaneous Absorption System) is a water-resistant topical gel providing sustained drug delivery. MCA® forms a tenacious film for either wet or dry surfaces where: 1) the product is applied to the skin or mucosal surface; 2) the product forms a tenacious moisture-resistant film; and 3) the adhered film provides sustained release of drug for a period from hours to days. Yet another product, BCP™ (Biocompatible Polymer System) provides a non-cytotoxic gel or liquid that is applied as a protective film for wound healing. Examples of these systems include Orajel®-Ultra Mouth Sore Medicine as well as those as described in the following published US patents and applications assigned to Atrix Laboratories Inc.: U.S. Pat. Nos. 6,537,565; 6,432,415; 6,355,657; 5,962,006; 5,725,491; 5,722,950; 5,717,030; 5,707,647; 5,632,727; and US 20010033853.

Dosage and Administration

The concentration of the active agent in any of the aforementioned dosage forms and compositions can vary a great deal, and will depend on a variety of factors, including the type of composition or dosage form, the corresponding mode of administration, the nature and activity of the specific active agent, and the intended drug release profile. Preferred dosage forms contain a unit dose of active agent, i.e., a single therapeutically effective dose. For creams, ointments, etc., a "unit dose" requires an active agent concentration that provides a unit dose in a specified quantity of the formulation to be applied. The unit dose of any particular active agent will depend, of course, on the active agent and on the mode of administration. For a sodium channel modulator, particularly a TTX-R sodium channel modulator and/or activity-dependent sodium channel modulator, the unit dose for oral administration will be in the range of from about 1 mg to about 10,000 mg, typically in the range of from about 100 mg to about 5,000 mg; for local administration, suitable unit doses may be lower. Alternatively, for a sodium channel modulator, particularly a TTX-R sodium channel modulator and/or activity-dependent sodium channel modulator, the unit dose for oral administration will be greater than about 1 mg, about 5 mg, about 10 mg, about 20 mg, about 30 mg, about 40 mg, about 50 mg, about 100 mg, about 200 mg, about 300 mg, about 400 mg, about 500 mg, about 1,000 mg, about 1,500 mg, about 2,000 mg, about 2,500 mg, about 3,000 mg, about 3,500 mg, about 4,000 mg, about 4,500 mg, about 5,000 mg, about 5,500 mg, about 6,000 mg, about 6,500 mg, about 7,000 mg, about 7,500 mg, about 8,000 mg, about 8,500 mg, about 9,000 mg, or about 9,500 mg. Those of ordinary skill in the art of pharmaceutical formulation can readily deduce suitable unit doses for sodium channel modulators, particularly TTX-R sodium channel modulators and/or activity-dependent sodium channel modulators, as well as suitable unit doses for other types of agents that may be incorporated into a dosage form of the invention.

For sodium channel modulators, particularly TTX-R sodium channel modulators and/or activity-dependent sodium channel modulators, the unit dose for transmucosal, topical, transdermal, intravesical, and parenteral administration will be in the range of from about 1 ng to about 10,000 mg, typically in the range of from about 100 ng to about 5,000 mg. Alternatively, for sodium channel modulators, particularly TTX-R sodium channel modulators and/or activity-dependent sodium channel modulators, the unit dose for transmucosal, topical, transdermal, intravesical, and parenteral administration will be greater than about 1 ng, about 5 ng, about 10 ng, about 20 ng, about 30 ng, about 40 ng, about 50 ng, about 100 ng, about 200 ng, about 300 ng, about 400 ng, about 500 ng, about 1 µg, about 5 µg, about 10 µg, about 20 µg, about 30 µg, about 40 µg, about 50 µg, about 100 µg, about 200 µg, about 300 µg, about 400 µg, about 500 µg, about 1 mg, about 5 mg, about 10 mg, about 20 mg, about 30 mg, about 40 mg, about 50 mg, about 100 mg, about 200 mg, about 300 mg, about 400 mg, about 500 mg, about 1,000 mg, about 1,500 mg, about 2,000 mg, about 2,500 mg, about 3,000 mg, about 3,500 mg, about 4,000 mg, about 4,500 mg, about 5,000 mg, about 5,500 mg, about 6,000 mg, about 6,500 mg, about 7,000 mg, about 7,500 mg, about 8,000 mg, about 8,500 mg, about 9,000 mg, or about 9,500 mg. Those of ordinary skill in the art of pharmaceutical formulation can readily deduce suitable unit doses for sodium channel modulators, particularly TTX-R sodium channel modulators and/or activity-dependent sodium channel modulator, as well as suitable unit doses for other types of agents that may be incorporated into a dosage form of the invention.

For sodium channel modulators, particularly TTX-R sodium channel modulators and/or activity-dependent sodium channel modulators, the unit dose for intrathecal administration will be in the range of from about 1 fg to about 1 mg, typically in the range of from about 100 fg to about 1 ng. Alternatively, for sodium channel modulators, particularly TTX-R sodium channel modulators and/or activity-dependent sodium channel modulators, the unit dose for intrathecal administration will be greater than about 1 fg, about 5 fg, about 10 fg, about 20 fg, about 30 fg, about 40 fg, about 50 fg, about 100 fg, about 200 fg, about 300 fg, about 400 fg, about 500 fg, about 1 pg, about 5 pg, about 10 pg, about 20 pg, about 30 pg, about 40 pg, about 50 pg, about 100 pg, about 200 pg, about 300 pg, about 400 pg, about 500 pg, about 1 ng, about 5 ng, about 10 ng, about 20 ng, about 30 ng, about 40 ng, about 50 ng, about 100 ng, about 200 ng, about 300 ng, about 400 ng, about 500 ng, about 1 µg, about 5 µg, about 10 µg, about 20 µg, about 30 µg, about 40 µg, about 50 µg, about 100 µg, about 200 µg, about 300 µg, about 400 µg, or about 500 µg. Those of ordinary skill in the art of pharmaceutical formulation can readily deduce suitable unit doses for sodium channel modulators, particularly TTX-R sodium channel modulators and/or activity-dependent sodium channel modulators, as well as suitable unit doses for other types of agents that may be incorporated into a dosage form of the invention.

A therapeutically effective amount of a particular active agent administered to a given individual will, of course, be dependent on a number of factors, including the concentration of the specific active agent, composition or dosage form, the selected mode of administration, the age and general condition of the individual being treated, the severity of the individual's condition, and other factors known to the prescribing physician.

In a preferred embodiment, drug administration is on an as-needed basis, and does not involve chronic drug administration. With an immediate release dosage form, as-needed administration may involve drug administration immediately prior to commencement of an activity wherein suppression of the symptoms of a GI tract disorder except for acid peptic disorders or structural gastroesophageal disorders would be desirable, but will generally be in the range of from about 0 minutes to about 10 hours prior to such an activity, preferably in the range of from about 0 minutes to about 5 hours prior to such an activity, most preferably in the range of from about 0 minutes to about 3 hours prior to such an activity. With a sustained release dosage form, a single dose can provide therapeutic efficacy over an extended time period in the range of from about 1 hour to about 72 hours, typically in the range of from about 8 hours to about 48 hours, depending on the formulation. That is, the release period may be varied by the selection and relative quantity of particular sustained release polymers. If necessary, however, drug administration may be carried out within the context of an ongoing dosage regimen, i.e., on a weekly basis, twice weekly, daily, etc.

Packaged Kits

In another embodiment, a packaged kit is provided that contains the pharmaceutical formulation to be administered, i.e., a pharmaceutical formulation containing a therapeutically effective amount of a selected active agent for the treatment of a GI tract disorder except for acid peptic disorders or structural gastroesophageal disorders, a container, preferably sealed, for housing the formulation during storage and prior to use, and instructions for carrying out drug administration in a manner effective to treat a GI tract disorder except for acid peptic disorders or structural gastroesophageal disorders. The instructions will typically be written instructions on a package insert and/or on a label. Depending on the type of formulation and the intended mode of administration, the kit may also include a device for administering the formulation. The formulation may be any suitable formulation as described herein. For example, the formulation may be an oral dosage form containing a unit dosage of a selected active agent. The kit may contain multiple formulations of different dosages of the same agent. The kit may also contain multiple formulations of different active agents.

Insurance claims

In general, the processing of an insurance claim for the coverage of a given medical treatment or drug therapy involves notification of the insurance company, or any other entity, that has issued the insurance policy against which the claim is being filed, that the medical treatment or drug therapy will be performed. A determination is then made as to whether the medical treatment or drug therapy that will be performed is covered under the terms of the policy. If covered, the claim is then processed, which can include payment, reimbursement, or application against a deductable.

The present invention encompasses a method for processing an insurance claim under an insurance policy for a sodium channel modulator, particularly a TTX-R sodium channel modulator and/or activity-dependent sodium channel modulator, or pharmaceutically acceptable salts, esters, amides, prodrugs, or active metabolites thereof used in the treatment of GI tract disorders except for acid peptic disorders or structural gastroesophageal disorders. This method comprises: 1) receiving notification that treatment of GI tract disorders except for acid peptic disorders or structural gastroesophageal disorders using said sodium channel modulator, particularly a TTX-R sodium channel modulator and/or activity-dependent sodium channel modulator, or pharmaceutically acceptable salts, esters, amides, prodrugs or active metabolites thereof will be performed or receiving notification of a prescription for said sodium channel modulator to treat GI tract disorders except for acid peptic disorders or structural gastroesophageal disorders; 2) determining whether said treatment using said sodium channel modulator, particularly a TTX-R sodium channel modulator and/or activity-dependent sodium channel modulator, or pharmaceutically acceptable salts, esters, amides, prodrugs or active metabolites is covered under said insurance policy; and 3) processing said claim for treatment using said sodium channel modulator, particularly a TTX-R sodium channel modulator and/or activity-dependent sodium channel modulator or pharmaceutically acceptable salts, esters, amides, prodrugs, or active metabolites thereof, including payment, reimbursement, or application against a deductable.

The present invention also encompasses the method for processing an insurance claim described above, wherein a sodium channel modulator, particularly a TTX-R sodium channel modulator and/or activity-dependent sodium channel modulator and a secondary agent are used in the treatment of GI tract disorders except for acid peptic disorders or structural gastroesophageal disorders. Secondary agents can include an antispasmodic, a tricyclic antidepressant, duloxetine, venlafaxine, a monoamine reuptake inhibitor, a spasmolytic, an anticholinergic, gabapentin, pregabalin, a substituted aminomethyl-phenyl-cyclohexane derivative, a 5-$HT_3$ antagonist, a 5-$HT_4$ antagonist, a β3 adrenergic agonist, a neurokinin receptor antagonist, a bradykinin receptor antagonist, a nitric oxide donor, or pharmaceutically acceptable salts, esters, amides, prodrugs, or active metabolites thereof. Furthermore, the method for processing an insurance claim according to the present invention encompasses wherein said sodium channel modulator, particularly a TTX-R sodium channel modulator and/or activity-dependent sodium channel modulator and said secondary agent, or pharmaceutically acceptable salts, esters, amides, prodrugs, or active metabolites thereof, are administered sequentially, concurrently in the same composition, or concurrently in different compositions. The method for processing an insurance claim according to the present invention also encompasses the processing of claims for a sodium channel modulator, particularly a TTX-R sodium channel modulator and/or activity-dependent sodium channel modulator and one of the secondary agents described above, or pharmaceutically acceptable salts, esters, amides, prodrugs, or active metabolites thereof, when either has been prescribed separately or concurrently for the treatment of GI tract disorders except for acid peptic disorders or structural gastroesophageal disorders.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended embodiments. Although specific terms are employed herein, they are used in a generic and descriptive sense only and not for purposes of limitation.

All patents, patent applications, and publications mentioned herein are hereby incorporated by reference in their entireties.

EXAMPLE

Methods for Treating Gastrointestinal Tract Disorders By Administering Sodium Channel Modulators The invention will be further described in the following examples, which do not limit the scope of the invention described in the claims. The following examples illustrate the effects of administration of sodium channel modulators on well-accepted models for gastrointestinal tract disorders. It is expected that these results will demonstrate the efficacy of sodium channel modulators for treatment of gastrointestinal tract disorders, except for acid peptic disorders or structural gastroesophageal disorders.

Objective and Rationale

The objective of the current study was to determine the effect of TTX-R sodium channel modulators or use dependent sodium channel modulators on the ability to modulate sodium currents in GI tract primary afferent neurons, a commonly used model of GI tract disorders.

Methods

Labeling of GI tract afferent neurons: Adult female Sprague-Dawley rats (150–300 g) were deeply anesthetized with pentobarbital anesthesia and placed on isoflurane maintenance anesthesia. A ventral midline incision was made through the abdominal skin and musculature, exposing the GI tract. Five injections of the fluorescent dyes Di-I (5 □l each of 25 mg/ml Di-I in DMSO) or Fast Blue (4% w/v) were made into the wall of the colon to label primary afferent fibers innervating the GI tract. The areas were rinsed with sterile saline to eliminate nonspecific spread of dye, and the incision was closed. Rats recovered for 5–12 days to allow for transport of fluorescent dye from distal terminals to the cell somata of dorsal root ganglion (DRG) neurons. Labeled neurons were identified in vitro using fluorescence optics.

Neuronal cultures: Fluorescent dye-injected rats were euthanized with pentobarbital anesthesia. For GI tract neurons, sacral (SI) DRG were dissected from the vertebral column. Ganglia were placed separately in Dulbecco's modified Eagles medium (DMEM) containing 0.3% collagenase B for 60 min at 37° C. The cell solution was exchanged for a 0.25% trypsin in calcium/magnesium-free Dulbecco's phosphate-buffered saline solution, and further digested for 30 min at 37° C. Following a wash in fresh DMEM, ganglia were dissociated by a series of triturations using fire-polished Pasteur pipettes. DRG cells were plated on polylysine-treated glass coverslips. Cells were plated at a density of 0.5 ganglion per coverslip in 1 ml DMEM supplemented with 10% FBS, NGF, and 100 U/ml penicillin/streptomycin. All experimental procedures involving rats were conducted under a protocol approved by an Institutional Animal Care and Use Committee. Small variations in the concentrations of reagents, incubation times, etc. may occur and are expected to give similar results.

In most experiments, neurons were incubated in culture medium containing the FITC-labeled lectin BSI-B4 (IB4, 10 mg/ml) at 37° C. for 5 min before recording. The coverslip was washed with extracellular recording solution for 1 min before being placed in a recording chamber mounted on the stage of an inverted microscope equipped with fluorescence optics. Neuronal images were captured using a digital camera system.

Electrophysiology: Electrophysiologic evaluation of neurons occured within 4–48 h of plating. Whole cell patch-clamp recordings were obtained from fluorescent dye-labeled DRG neurons. Recordings were obtained in an extracellular recording solution (pH 7.4, 295–320 mosM) consisting of (in mM) 140 NaCl, 3 KCl, 1 CaCl2, 1 MgCl2, 0.1 CdCl2, 10 HEPES, and 10 glucose. Patch-clamp electrodes were pulled from borosilicate glass and fire polished to 2–6 MOhm tip resistance. The internal pipette recording solution (pH 7.3, 290–300 mosM) consisted of (in mM) 140 CsCl, 10 NaCl, 1 EGTA, and 10 HEPES. Tetrodotoxin (TTX, 0.3 uM) was included in the extracellular solution to block TTX-sensitive sodium currents. Variations in the concentrations and types of reagents used for solutions may occur and are expected to give similar results.

Sodium currents were recorded from DRG neurons using standard electrophysiologic protocols. Neurons were typically voltage-clamped at −50 mV. Currents were recorded using a patch-clamp amplifier and digitized at 3–10 kHz for acquisition. Neuronal input resistance and membrane capacitance were determined from the amplitude and kinetics of the current response to a voltage pulse from a holding potential of −50 mV. Series resistance was compensated 75–95% for all recordings. Leak currents were cancelled online using a standard P/4 protocol. A series of 50 msec voltage steps from −60 to +40 mV in 5 mV increments were delivered every 5 sec for sodium current-voltage relationships. To study tonic modulation of sodium currents by drugs, depolarizing test pulses from either −50 mV or −90 mV to 0 mV were delivered every 5 sec during drug application. To study activity-dependent modulation of sodium currents by drugs (Li et al., (1999) *Molecular Pharmacology* 55:134–141), a high-frequency stimulus train (40 depolarizing pulses at 17 Hz) was delivered immediately prior to the depolarizing test pulse. For all cell types, baseline responses were recorded for a period of time to ensure that the response was stable. A wash out or recovery period usually followed the drug application period. All data acquisition and analysis was performed using standard cell electrophysiology software. Variations in the details of electrophysiologic protocols may occur and are expected to give similar results.

For the condition involving Lamotrigine, cells were constantly perfused with extracellular solution at a rate of approximately 1 ml/min in the recording chamber. Lamotrigine was applied through the bath to individual cells until a steady-state drug effect was achieved.

For the condition involving Ambroxol, cells were constantly perfused with extracellular solution at a rate of 0.5–2 ml/min in the recording chamber and Ambroxol was applied through the bath to individual cells. These agents were typically applied for 2–10 minutes, or until a steady-state drug effect was achieved. Cumulative concentration-response curves were obtained from consecutive increases in drug concentration to each cell.

All data are expressed as mean±SEM.

Results and Conclusions

GI tract afferent neurons were identified as fluorescent-dye positive neurons in in vitro DRG cultures.

FIG. 1 demonstrates the use-dependent effects of lamotrigine (100 □M) on peak activity dependent sodium currents recorded in colon DRG neurons. Slow activation of sodium currents consisted of step depolarizations from −50 to 0 mV delivered at a frequency of 0.2 Hz. Slow activation of sodium currents consisted of step depolarizations from −50 to 0 mV delivered at a frequency of 0.2 Hz. Fast activation consisted of the same step depolarizations delivered at a frequency of 17 Hz. FIG. 1A shows a typical response to lamotrigine under both slow and fast stimulation protocols. Peak current amplitude was decreased to a greater extent under fast stimulation conditions, consistent with use-dependent modulation of colon DRG sodium currents. FIG. 1B shows summary data obtained from three neurons. Data were obtained under control conditions and during application of 100 □M lamotrigine. The mean peak sodium current amplitude (expressed as mean % control amplitude±SEM) is decreased to a greater extent under fast stimulation conditions, consistent with modulation of colon DRG sodium currents in a use-dependent manner. Asterisk indicates significant difference vs slow stimulation (P<0.05, t-test).

Figure 2:
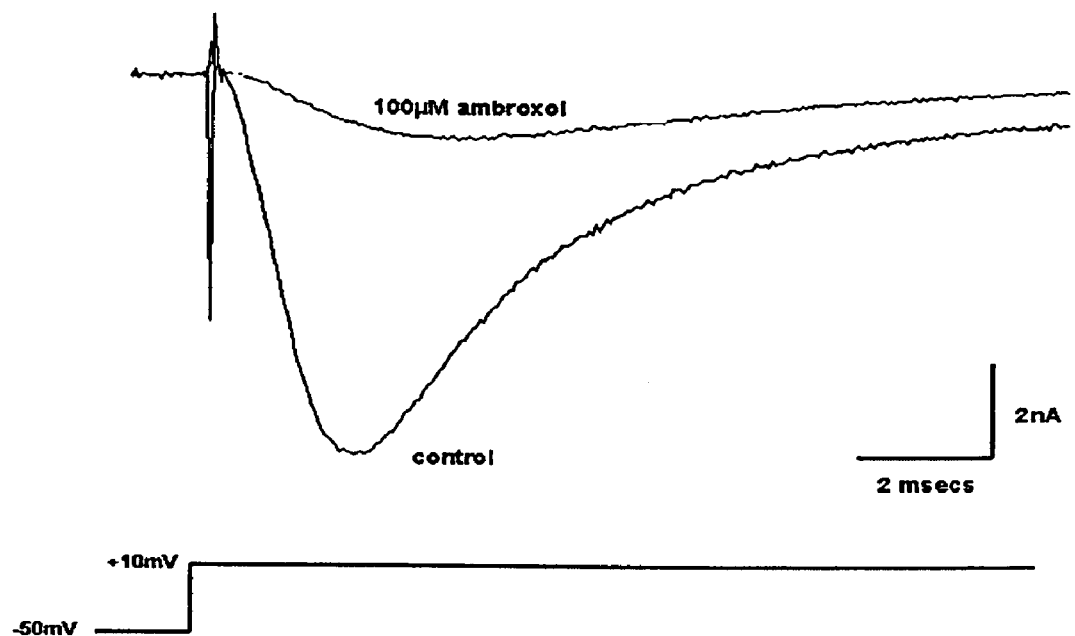
FIG. 2.
Figure 2:
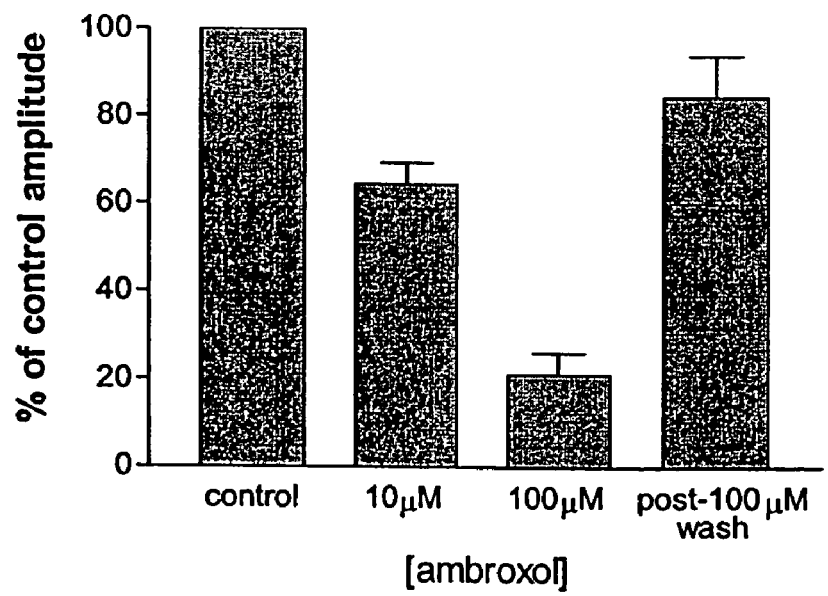

FIG. 2A shows a typical inward TTX-R sodium current recorded before (control) and during (100 µM) bath application of Ambroxol. The kinetics of this and other responses recorded in similar GI tract afferent neurons resembled the Nav1.8 subtype of current. This is the "slow (Nav1.8)" as opposed to the "persistent (Nav1.9)" sodium current as described in Renganathan et al. (2002) *J. Neurophysiol.*, 87:76.1–775.

FIG. 2B shows that Ambroxol produced a concentration-dependent reversible block of TTX-R sodium currents in four GI tract afferent neurons. The block occurred at an estimated IC50 concentration between 10 and 100 µM, consistent with selective block of TTX-R current by Ambroxol (Weiser and Wilson (2002) *Mol. Pharmacol.* 62:433–438).

This example demonstrates the efficacy of sodium channel modulators in mammalian forms of GI tract disorders.

What is claimed is:

1. A method for treating a functional gastrointestinal tract disorder, which comprises administering to an individual in need thereof a therapeutically effective amount of ambroxol or a pharmaceutically acceptable salt, enantiomer, analog, ester, amide, prodrug, metabolite, or derivative thereof wherein said functional gastrointestinal tract disorder is selected from the group consisting of irritable bowel syndrome, slow-transit constipation, non-ulcer dyspepsia, an evacuation disorder and functional dysphasia.

2. The method of claim 1, wherein said functional gastrointestinal tract disorder is irritable bowel syndrome.

3. The method of claim 1, wherein said functional gastrointestinal tract disorder is slow-transit constipation.

4. The method of claim 1, wherein said functional gastrointestinal tract disorder is non-ulcer dyspepsia.

5. The method of claim 1, wherein said functional gastrointestinal tract disorder is an evacuation disorder.

6. The method of claim 1, wherein said functional gastrointestinal tract disorder is functional dysphagia.

7. The method of claim 1, wherein said ambroxol or a pharmaceutically acceptable salt, enantiomer, analog, ester, amide, prodrug, metabolite, or derivative thereof is administered orally, transmucosally, sublingually, buccally, intranasally, transurethrally, rectally, by inhalation, topically, transdermally, parenterally, or intrathecally.

8. The method of claim 1, wherein said ambroxol or a pharmaceutically acceptable salt, enantiomer, analog, ester, amide, prodrug, metabolite, or derivative thereof is administered concurrently with an additional active agent.

9. The method of claim 8, wherein the additional active agent is selected from the group consisting of an antispasmodic, a tricyclic antidepressant, duloxetine, venlafaxine, a monoamine reuptake inhibitor, a spasmolytic, an anticholinergic, gabapentin, pregabalin, a substituted aminomethyl-phenyl-cyclohexane derivative, a 5-$HT_3$ antagonist, a 5-$HT_4$ antagonist, a β3 adrenergic agonist, a neurokinin receptor antagonist, a bradykinin receptor antagonist, a nitric oxide donor, and derivatives thereof.

* * * * *

UNITED STATES PATENT AND TRADEMARK OFFICE
CERTIFICATE OF CORRECTION

PATENT NO. : 7,041,704 B2  Page 1 of 1
APPLICATION NO. : 11/057024
DATED : May 9, 2006
INVENTOR(S) : Burgard et al.

It is certified that error appears in the above-identified patent and that said Letters Patent is hereby corrected as shown below:

Column 24:

Line 66, "Phenyloin" should read --Phenytoin--;

Line 67, "Phenyloin" should read --Phenytoin--;

Column 25:

Line 17, "Fosphenyloin" should read --Fosphenytoin--;

Line 18, "phosphenyloin" should read --phosphenytoin--;

Column 49:

Line 34, "$R_1$" should read --$R_{11}$--;

Line 66, "$CR_2$," should read --$CR_{21}$--;

Column 50

Line 7, "$R_2$," should read --$R_{21}$--;

Signed and Sealed this

Nineteenth Day of September, 2006

JON W. DUDAS
*Director of the United States Patent and Trademark Office*